US005723436A

United States Patent [19]

Huang et al.

[11] Patent Number: 5,723,436
[45] Date of Patent: Mar. 3, 1998

[54] CALCINEURIN INTERACTING PROTEIN COMPOSITIONS AND METHODS

[75] Inventors: Laiqiang Huang, Mountain View; Martha S. Cyert, Palo Alto, both of Calif.

[73] Assignee: The Board of Trustees of the Leland Stanford Junior University, Palo Alto, Calif.

[21] Appl. No.: 328,322

[22] Filed: Oct. 24, 1994

[51] Int. Cl.$^6$ .......................... A61K 38/04; A61K 38/16; C07K 14/395

[52] U.S. Cl. ..................... 514/2; 514/12; 514/13; 514/14; 530/300; 530/350; 530/371

[58] Field of Search ................... 530/350, 371, 530/324-326, 300; 435/69.1; 514/2, 12-14

[56] References Cited

PUBLICATIONS

Reeck et al., *Cell*, vol. 50, p. 667, 1987.
Chien, C.-T., et al., "The Two-Hybrid System: a Method to Identify and Clone Genes for Proteins that Interact with a Protein of Interest," *Proc. Natl. Acad. Sci. U.S.A.* 88:9578–9582 (1991).
Clipstone, N.A., and Crabtree, G.R., "Identification of Calcineurin as a Key Signalling Enzyme in T-Lymphocyte Activation," *Nature* 357:695–697 (1992).
Cyert, M.S., "Immunosuppressants Hit the Target," *Current Biology* 2(1):18 (1992).
Dujon, B., et al., "Complete DNA Sequence of Yeast Chromosome XI," *Nature* 369:371–378 (1994).
Durfee, T., et al., "The Retinoblastoma Protein Associates with the Protein Phosphatase Type 1 Catalytic Subunit," *Genes & Development* 7:555–569 (1993).
Fields, S., and Song, O.-k., "A Novel Genetic System to Detect Protein–Protein Interactions," *Nature* 340:245–246 (1989).
Foor, F., et al., "Calcineurin Mediates Inhibition by FK506 and Cyclosporin of Recovery from α–Factor Arrest in Yeast," *Nature* 360:682–684 (1992).
Pflügl, G., et al., "X-Ray Structure of a Decameric Cyclophilin–Cyclosporin Crystal Complex," *Nature* 361:91–94 (1993).
Rogers, S., et al., "Amino Acid Sequences Common to Rapidly Degraded Proteins: The PEST Hypothesis," *Science* 234;364–368 (1986).
Steiner, J.P., et al., "High Brain Densities of the Immunophilin FKBP Colocalized with Calcineurin," *Nature* 358:584–587 (1992).
Yang, X., et al., "A Protein Kinase Substrate Identified by the Two–Hybrid System," *Science* 257:680–682 (1992).

*Primary Examiner*—Marian C. Knode
*Assistant Examiner*—Stephen Gucker
*Attorney, Agent, or Firm*—Dehlinger & Associates

[57] ABSTRACT

An identification and characterization of a calcineurin interacting protein effective to enhance immunosuppressive effects of calcineurin-targeted immunosuppressants by potentiating an interaction of an immunophilin with calcineurin is described herein. One embodiment of the invention is the CNI polypeptide encoded by the CNI gene of *Saccharomyces cerevisiae*. Polynucleotides encoding a CNI protein are also described. Also described are yeast cells carrying mutations in the CNI gene. Further, a method of identifying a small molecule immunosuppressant compound is described. The methods include the use of a cell-based two hybrid protein-protein interaction assay, wherein one of two fusion hybrid proteins in a cell contains a subunit of calcineurin, and the other of two fusion hybrid proteins contains an immunophilin.

2 Claims, 11 Drawing Sheets

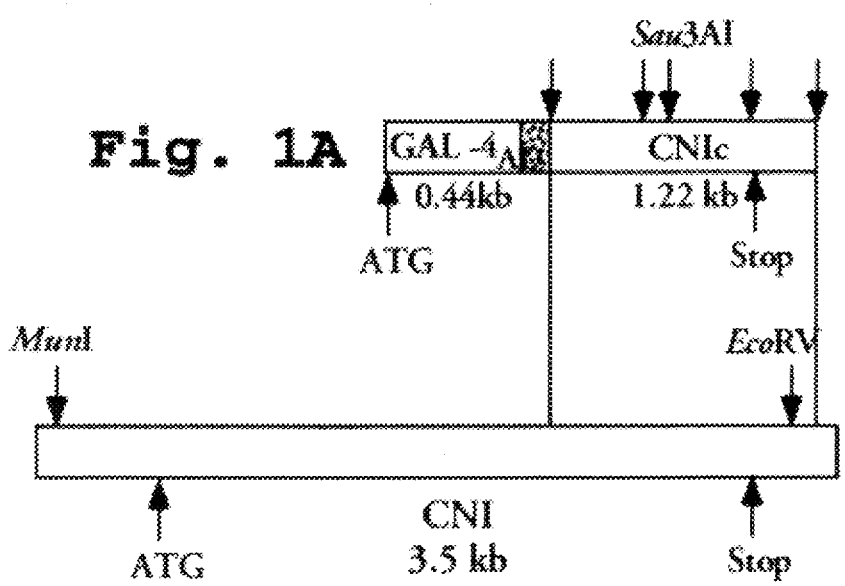
Fig. 1A
Fig. 1B
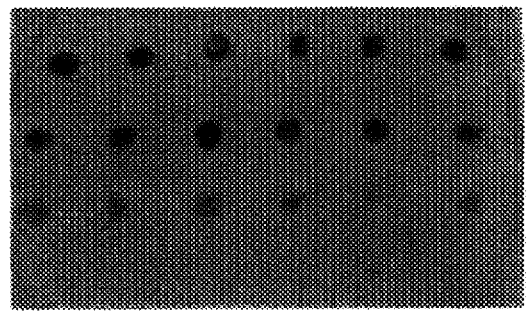
Fig. 2A
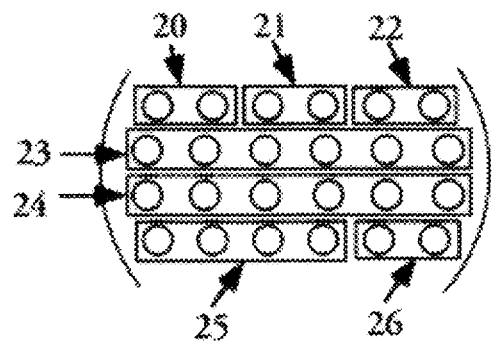
Fig. 2B

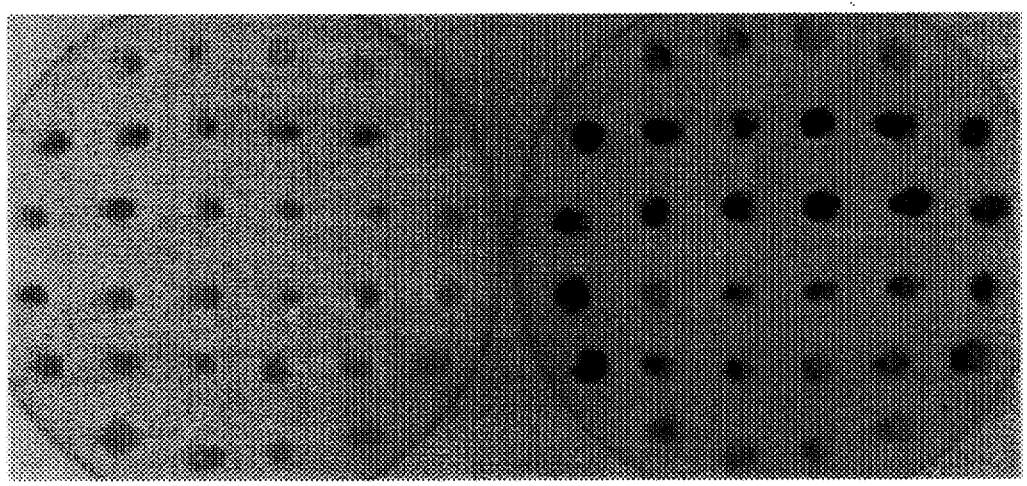
Fig. 7A          Fig. 7C
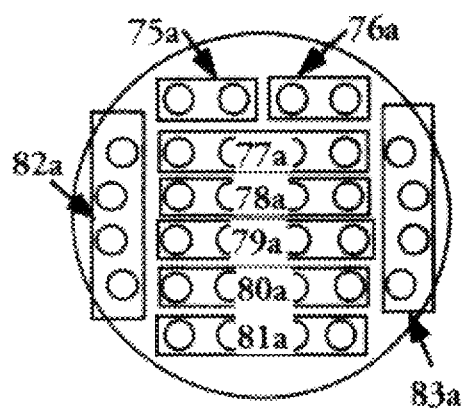 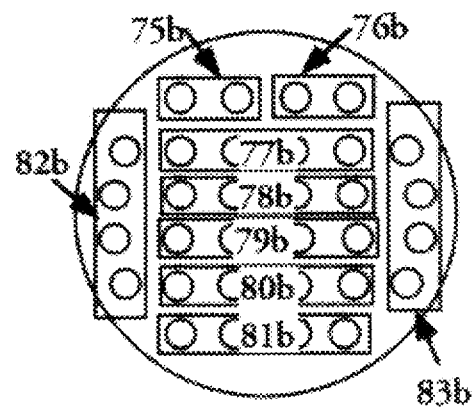
Fig. 7B          Fig. 7D

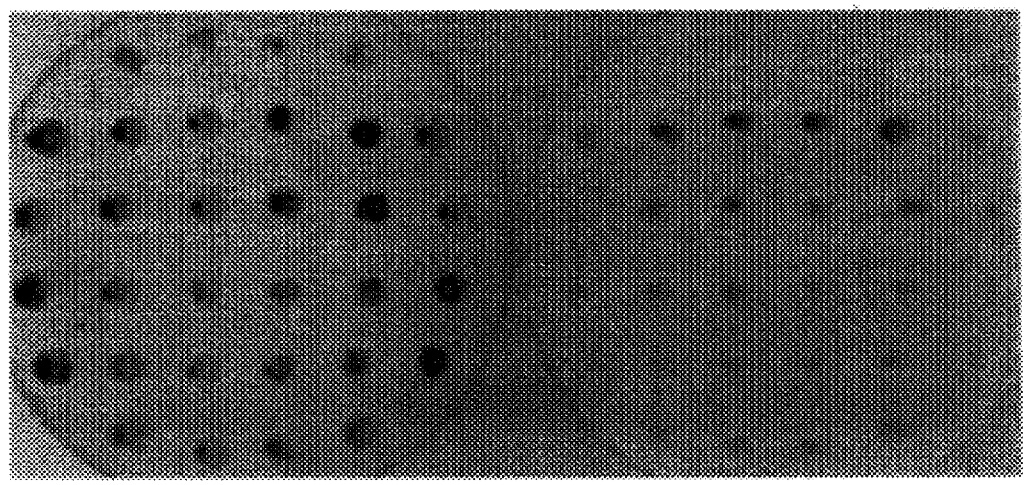
Fig. 7E    Fig. 7G
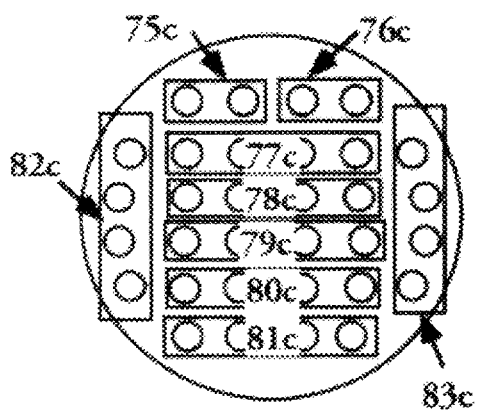  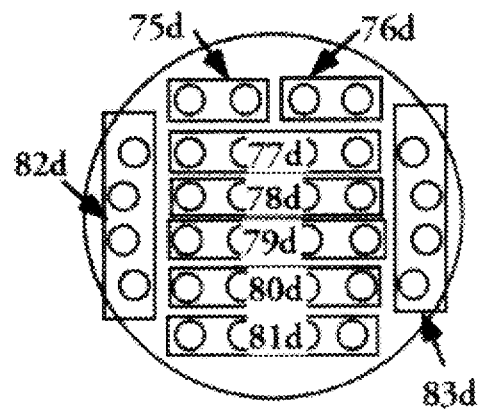
Fig. 7F    Fig. 7H

```
ccgaacacttccttcgagagagtgcattttactatgtgaaccaattttcctcttttcggtttgcaagt
tcacctgaaaaactgcttaacactactagcaattgccctattgtcgtacgaggactttgccaaatgtatt
cccggctgtttgtagtatatatacgcagatatataatagcgccgtcttttacctctttgagcgaattgc
caaatattgactcttttgtcttatttcgctatccccatcttatcaaaaatgggaacaactcgttgaaata
agagacaagcaacaagaaagacaaccaacagaaagttccattccgcacaaatacgctggaatcccataga
atattgcttgttcctctatgactacatgctccaattcaatacagaaaatgatactgtagctccagtgttt
cccatggagcaagatataaatgcagcacctgatgccgtcccactggtgcagacaacaacactacaagtct
ttgtaaagcttgccgaacccatagtgtttttaaaaggatttgaaactaacggactgtctgaaatagcccc
cagtatcttacgaggatctcttatcgtcagggtgttgaaaccgaataaattaaaaagtatatcgataacc
ttcaaaggaatatccagaacagagtggccggaaggtataccaccgaagagagaagaattttcagatgttg
aaactgttgtcaatcacacatggccatttatcaggcggatgacggcatgaattctttcaccttagaaca
tcacagctcaaataattcgtccaatcgcccatctatgagcgatgaagattatctacttgaaaaaagcggt
gcttcagtatatatcccaccaaccgctgaaccccctaaagataatagcaatctaagtctggatgcctatg
agcgcaactcattgtcatccgataatttgagtaacaagccagtatcaagtgatgtttcccatgacgacag
taaactgttggctattcaaaagacaccattaccatcatctagtcgaagaggatcggtaccggcaaatttt
cacggtaactctttgtcacctcataccttcatatctgatttgttcacaaaaacattcagtaatagtggcg
ctactccaagtcctgagcaagaggataactatcttacaccatccaaagattctaaagaagtttttatttt
tcgaccgggcgattatatttacactttgaacagccaatatcgcaatcttatccagaaagtataaaagcc
aatttggttccgtggagtataaactgtcaatagacatagagaggtttggcgcattcaaatcaactatac
atactcaattacccatcaaagtcgtaaggcttccttctgatggatccgtagaagagactgaagctattgc
aatttccaaggactggaaagatcttcttcattatgacgtggtaattttctcgaaagagatcgttttgaat
gcatttttacccatcgatttccatttcgctcctctagataaagttactctgcatcgtattagaatttatc
taacagagtctatggaatacacttgtaatagtaatggaaatcacgagaaggctcgtagattagagccaac
taaaaagtttctgttggctgaacataacggtcctaaactgcctcatataccagctggttcgaatcctttg
aaggctaaaaatagagggaacatcctcttggatgaaaaatccggcgatctagttaacaaagattttcagt
tcgaggtgtttgtcccaagcaagtttacaaacagtatacggttacaccctgatacaaattatgataaaat
caaagcccaccattggataaaaatttgccttcgtctttccaagaagtacggggacaatagaaaacatttc
gaaataagtattgattctccaatccatattttaaatcaactatgctcacacgcgaatactttgctaccga
gctacgagagtcatttccagtattgtgatgaagatggtaatttcgcaccagcagcagatcaacaaaatta
cgcaagtcatcatgattccaatattttcttcccaaaagaagttctttcgtctcccgttctttcacctaac
gtgcagaagatgaacattagaataccgtctgatcttccagtagtgcgtaatagagctgaaagcgtaaaga
aaagcaagtcagataatacctccaagaagaatgatcaaagtagcaatgtcttcgcatccaaacagctggt
cgcaaacatttataagcccaatcagattccaagagaattaacttctcctcaggcgttaccattatcgccc
atcacctcaccaattctcaattaccaaccattatcaaactccccgcctccagattttgattttgatctag
ctaagcgcggcgcagccgattctcatgctattcctgtggatcctccatcatatttgatgtattaaaggc
cgatgggattgaattgccatactacgatacaagttcatctaaaattcctgaactaaaactaaacaaatct
agagagacattggccagcattgaggaggactcattcaatggttggtctcaaattgatgacttatccgacg
aagatgacaatgatggcgatatagcatctggtttcaacttcaagctgtcaaccagtgctccgagtgagaa
cgttaattcacacactcctattttgcagtctttaaacatgagtcttgatgggagaaaaaaaatcgtgcc
agtctacacgcaacatcagtgttacctagtacaataagacagaacaatcagcatttcaatgacataaacc
agatgctaggcagtagtgacgaagatgcctttcccaaaagccaatcattaaatttcaataagaaactacc
aatacttaaaattaatgataacgtcatacaatcaaacagcaatagtaataacagagttgataatccagaa
gatacagtggattcttcagtcgatattacagcattttatgatccaagaatgtcatcagattccaaatttg
attgggaggtaagcaagaaccatgttgacccagcagcctactcggttaacgttgctagtgaaaaccgtgt
actggacgactttaagaaagcatttcgcgaaaagagaaaataagtacattattttcattctccgacagaa
ttgctaccattttactttgtgtcctgtgattcaatagtgtacaatatattggacattttatagtatacaa
atatacaccatcaatctatacatccatatcacttgtcgtaaagatatcccttttttaatagtacagcgatt
aaaaaaataacatgattaacgttcagttaccaatgagcttatttattaggcttgctttagattttccaa
gtcaattttgtttttctaacgcttgcaacctcatctcaaccttcttcctttgcaagcagatcttcgaa
accatctcgtttattctctcaatgctgttcccactttcatcatcgtctgggaaaagtaccggtaagggcg
```

Fig. 12

MLQFNTENDTVAPVFPMEQDINAAPDAVPLVQTTTLQVFVKLAEPIVFLKGFETNGLSEIAPSILRGSLIVR

VLKPNKLKSISITFKGISRTEWPEGIPPKREEFSDVETVVNHTWPFYQADDGMNSFTLEHHSSNNSSNRPSM

SDEDYLLEKSGASVYIPPTAEPPKDNSNLSLDAYERNSLSSDNLSNKPVSSDVSHDDSKLLAIQKTPLPSSS

RRGSVPANFHGNSLSPHTFISDLFTKTFSNSGATPSPEQEDNYLTPSKDSKEVFIFRPGDYIYTFEQPISQS

YPESIKANFGSVEYKLSIDIERFGAFKSTIHTQLPIKVVRLPSDGSVEETEAIAISKDWKDLLHYDVVIFSK

EIVLNAFLPIDFHFAPLDKVTLHRIRIYLTESMEYTCNSNGNHEKARRLEPTKKFLLAEHNGPKLPHIPAGS

NPLKAKNRGNILLDEKSGDLVNKDFQFEVFVPSKFTNSIRLHPDTNYDKIKAHHWIKICLRLSKKYGDNRKH

FEISIDSPIHILNQLCSHANTLLPSYESHFQYCDEDGNFAPAADQQNYASHHDSNIFFPKEVLSSPVLSPNV
⌐▶ CNIc
QKMNIRIPSDLPVVRNRAESVKKSKSDNTSKKNDQSSNVFASKQLVANIYKPNQIPRELTSPQALPLSPITS

PILNYQPLSNSPPPDFDFDLAKRGAADSHAIPVDPPSYFDVLKADGIELPYYDTSSSKIPELKLNKSRETLA

SIEEDSFNGWSQIDDLSDEDDNDGDIASGFNFKLSTSAPSENVNSHTPILQSLNMSLDGRKKNRASLHATSV

LPSTIRQNNQHFNDINQMLGSSDEDAFPKSQSLNFNKKLPILKINDNVIQSNSNSNNRVDNPEDTVDSSVDI

TAFYDPRMSSDSKFDWEVSKNHVDPAAYSVNVASENRVLDDFKKAFREKRK

Fig. 13

CALCINEURIN INTERACTING PROTEIN COMPOSITIONS AND METHODS

This invention was made with Government support under grants GM 48729 from the National Institutes of Health and MCB 9357017 from the National Science Foundation. Accordingly, the United States Government has certain rights in this invention.

FIELD OF THE INVENTION

The present invention relates to compounds affecting the function of calcineurin, particularly interactions of calcineurin with immunosuppressant drugs.

REFERENCES

Ausubel, F. M., et al., *Current Protocols in Molecular Biology* (John Wiley and Sons, Inc., Media, Pa.).

Bartel, P., et al., *BioTechniques* 14:920–924 (1993).

Beach, D., et al., *Mol. Gen. Genet.* 187:326–329 (1982).

Better, M., et al., *Science* 240:1041–1043 (1988).

Breeden, J., et al., *Cold Spring Harbor Symp. Quant. Biol.* 50:643 (1985).

Brent, R., et al., *Cell,* 43:729–736 (1985).

Briggs J. D., *Immunology Letters,* 29 (1–2):89–94 (1991).

Cabilly, S., et al., European Patent Application No. 84/302368.0, Publication No. 0 125 023, published 14 Nov. 1984.

Chien, C.-t, et al., *Proc. Natl. Acad. Sci. U.S.A.,* 88:9578 (1991).

Clipstone, N. A., et al., *Nature* 357:695 (1992).

Cyert, M. S., *Current Biology* 2:18 (1992).

Cyert, M. S., et al., *PNAS* 88:7376 (1991).

Cyert, M. S., et al., *Mol. Cell. Biol.* 12:3460 (1992).

Dayhoff, M. O., in *Atlas of Protein Sequence and Structure,* National Biomedical Research Foundation 5:101–110, and Supplement 2 to this volume, pp. 1–10.

Dice, J. F., *FASEB J.* 1:349–357 (1987).

Durfee, T., et al., *Genes & Development* 2:555 (1993).

Fields, S., et al., *Nature* 340:245 (1989).

Foor, F., et al., *Nature* 360:682 (1992).

Guerini, D., et al., *Adv. Prot. Phosphatases* 6:391 (1991).

Guthrie, C., et al., *Meth. Enzymol.* 194:1–774 (1992).

Gyuris J., et al., *Cell,* 75:791–803 (1993).

Harlow, E., et al., *Antibodies: A Laboratory Manual,* Cold Spring Harbor Press, Cold Spring Harbor, N.Y. (1988).

Heitman, J., et al., *PNAS* 88:1948–52 (1991).

Hill, J. E., et al., *Yeast* 2:163–67 (1986).

Kennedy, M. S., et al., *Am. J. Med.* 78:978 (1983).

Klee, C. B., et al., "The calmodulin-regulated protein phosphatase" In *Calmodulin,* Klee, C. P., ed. (Elsevier, Amsterdam) (1988).

Kunkle, T. A., *PNAS* 82:488–92 (1985).

Laemmli, U., *Nature* 227:680–85 (1970).

Liu, J., et al., *Cell* 66:807 (1991).

Ma, J., et al., *Cell* 55:443–446 (1988).

Platt, J. L., et al., *Immunology Today,* 11 (12):450 (1990).

Reneke, J. E., et al., *Cell* 55:221 (1988).

Roberts, J. P., et al., *Ann. Rev. Med.,* 40:287 (1989).

Rogers, et al., *Science* 234:364 (1986).

Rose, M. D., et al., *Methods in Yeast Genetics* (Cold Spring Harbor, N.Y., 1990).

Sambrook, J., et al., *Molecular Cloning: A Laboratory Manual* (Cold Spring Harbor, N.Y., 1972).

Sanger, F., et al., *PNAS* 74:5463–67 (1977).

Schiestl, R. H., et al., *Curr. Genet.* 16:339 (1989).

Schreiber, S. L., *Science* 251:283 (1991).

Schreiber, S. L., et al., *Immunol. Today* 13:136 (1992).

Sherman, F., et al., *Methods in Yeast Genetics* (Cold Spring Harbor Laboratory Press, Cold Spring Harbor, N.Y.) (1979).

Sikorski, R. S., et al., *Genetics* 122:19–27 (1989).

Skerra, A., et al., *Science* 240:1038–1041 (1988).

Storb, R., *Blood* 66:698 (1985).

Storb, R., et al., *N. Engl. J. Med.* 314:729 (1986).

Triezenberg, S. J., et al., *Genes & Development,* 718–29 (1988).

Weiss, A., et al., *Cell* 76:263 (1994).

Wilson, I., et al., *Cell* 37:767 (1984).

Yang, X., et al., *Science* 257:680 (1992).

BACKGROUND OF THE INVENTION

The immune system functions as the body's major defense against diseases caused by invading organisms. This complex system fights disease by killing invaders such as bacteria, viruses, parasites or cancerous cells while leaving the body's normal tissues unharmed. The immune system's ability to distinguish the body's normal tissues, or self, from foreign or cancerous tissue, or non-self, is an essential feature of normal immune system function. A second essential feature is memory, the ability to remember a particular foreign invader and to mount an enhanced defensive response when the previously encountered invader returns. The loss of recognition of a particular tissue as self and the subsequent immune response directed against that tissue produce serious illness.

An autoimmune disease results from the immune system attacking the body's own organs or tissues, producing a clinical condition associated with the destruction of that tissue. An autoimmune attack directed against the joint lining tissue results in rheumatoid arthritis; an attack against the conducting fibers of the nervous system results in multiple sclerosis. The autoimmune diseases most likely share a common pathogenesis and the need for safe and effective therapy. One type of therapy that has been employed in combating autoimmune disease is treatment with immunosuppressant drugs, such as cyclosporin A, FK506 and rapamycin. While the treatments are often effective, the drugs typically have undesirable side effects, including neurotoxicity, nephrotoxicity, hypertension, and metabolic disorder. Many of these side effects are due to the drugs' action on cells other than those of the immune system.

In addition to their use in treating autoimmune conditions, immunosuppressive agents have also been used in treating or preventing transplantation rejection. Organ transplantation involving human organ donors and human recipients (allogeneic grafts), and non-human primate donors and human recipients (xenogeneic grafts), has received considerable medical and scientific attention (e.g., Roberts, 1989; Platt, 1990). To a great extent, this effort has been aimed at eliminating, or at least reducing, the problem of rejection of the transplanted organ. In the absence of adequate immunosuppressive therapy, the transplanted organ is destroyed by the host immune system.

Presently, the most commonly used agents for preventing transplant rejection include corticosteroids, cytotoxic drugs that specifically inhibit T cell activation such as azathioprine, immunosuppressive drugs such as cyclosporin A, and specific antibodies directed against T lymphocytes or surface receptors that mediate their activation (Briggs, 1991; Kennedy, 1983; Storb, 1985; Storb, 1986). All of these drug therapies are limited in effectiveness, in part because the doses needed for effective treatment of transplant rejection may increase the patient's susceptibility to infection by a variety of opportunistic invaders, and in part because of direct toxicity and other side effects.

Cyclosporin A, currently the most effective and most commonly used agent, is significantly toxic to the kidney. This nephrotoxicity limits the quantity of drug that can be safely given. The physician is frequently forced to administer sub-optimal doses of the drug because of this toxicity. A preparation capable of potentiating the action of immunosuppressive agents such as cyclosporin A on the immune system, thus allowing the administration of lower doses of drug, would be of considerable value in reducing the morbidity and mortality associated with transplantation.

SUMMARY OF THE INVENTION

In one embodiment, the present invention includes polypeptide compositions effective to enhance immunosuppressive effects of calcineurin-targeted immunosuppressants by potentiating an interaction of an immunophilin with calcineurin. The present invention includes the isolation and characterization of a calcineurin interacting protein, CNI, having these properties. Also disclosed herein are methods for the isolation and characterization of further CNI-related sequences and sequences of CNI-variants. The amino acid sequences presented as SEQ ID NO:2 and SEQ ID NO:5 are exemplary of the polypeptides of the present invention.

The present invention also includes a CNI polypeptide fragment that interacts specifically with the "A" subunits of calcineurin (CNA1 and CNA2), but not with calcineurin "B" subunit (CNB1). In one embodiment, this fragment has an amino acid sequence of between 15 and 915 amino acids in length, for example, the c-terminal 306 amino acids of the CNI protein (CNIc).

Included aspects of the invention are an CNI polypeptide; a recombinant CNI polypeptide; and a fusion polypeptide comprised of an CNI polypeptide. Exemplary fusion proteins include fusions to β-galactosidase.

The invention further includes isolated nucleic acid sequences encoding the above described polypeptides and polypeptide fragments. Exemplary nucleic acid sequences include the sequences presented as SEQ ID NO:1, SEQ ID NO:3, SEQ ID NO:4 and SEQ ID NO:6. The present invention includes CNI-encoding genomic polynucleotides, cDNAs thereto and complements thereof. With respect to polynucleotides, some aspects of the invention include: a purified CNI-encoding genomic polynucleotide; CNI polypeptide-encoding RNA and DNA polynucleotides; recombinant CNI polypeptide-encoding polynucleotides; a recombinant vector including any of the above recombinant polynucleotides, and a host cell transformed with any of these vectors. Another aspect of the invention is a polynucleotide probe for CNI polypeptide-encoding sequences.

Portions of a CNI-polypeptide coding sequences are effective as probes to isolate variants coding sequences which occur naturally, or to determine the presence of such coding sequences in nucleic acid samples. Such probes include hybridization screening probes and polymerase chain reaction amplification primers specific for CNI-polypeptide coding sequences. Homologues of CNI may be isolated from a number of sources, such as other types of yeast cells (e.g., Schizosaccharomyces) or mammalian cells (e.g., human).

Other aspects of the invention include: a recombinant expression system which incorporates an open reading frame (ORF) derived from CNI polypeptide-encoding sequences, wherein the ORF is linked operably to a control sequence which is compatible with a desired host, a cell transformed with the recombinant expression system, and a polypeptide produced by the transformed cell. Typically the expression system includes a vector having (a) a nucleic acid containing an open reading frame that encodes a CNI-polypeptide; and (b) regulatory sequences effective to express said open reading frame in a host cell. The regulatory sequence may include sequences useful for targeting or secretion of the CNI-polypeptide: such as a secretory signal recognized in yeast or bacterial expression systems.

The invention includes a method of recombinantly producing CNI-polypeptides. In the method, a recombinant expression system containing an open reading frame (ORF) having a polynucleotide sequence which encodes a CNI-polypeptide, where the vector is designed to express the ORF in the host, is introduced into suitable host cells. The host is then cultured under conditions resulting in the expression of the ORF sequence. The CNI-polypeptide sequences discussed above are examples of suitable CNI-polypeptides. Numerous vectors and their corresponding hosts are useful in the practice of this method of the invention, including, but not limited, to the vectors described herein for expression in yeast cells, and lambda gt11 phage vector and *E. coli* cells. Other host cells include insect and mammalian cell expression systems.

The invention also includes purified antibodies that are immunoreactive with a CNI-polypeptide. The antibodies may be polyclonal or monoclonal. Antibodies that are specifically immunoreactive with CNI-polypeptides may be useful for the isolation of CNI-polypeptide homologues from other cell type sources (e.g., mammalian).

The present invention also includes, a method of identifying a small molecule immunosuppressant compound. In the method, a cell-based two hybrid protein-protein interaction assay is constructed where one of two fusion hybrid proteins in the cell contains a subunit of calcineurin, and the other of two fusion hybrid proteins contains an immunophilin. The cell is then contacted with the small molecule being tested. A small molecule is identified as an immunosuppressant if the molecule potentiates an interaction between the two hybrid proteins. In one embodiment, the method is carried out using yeast cells, where one of the two fusion hybrid proteins contains a GAL4 activation domain and the other of two fusion hybrid proteins contains a GAL4 binding domain. The method can be carried out where subunits of calcineurin are from any cell source, in particular, yeast or mammalian cells (including human cells). The subunit may, for example, be yeast calcineurin subunit CNA1 or CNA2, or human calcineurin subunit "A". The immunophilin can, for example, be cyclophilins or FK506-binding proteins (e.g., FKBP12) typically from a homologous cell source.

Also included in the present invention is another method of identifying a small molecule immunosuppressant compound. In the method, a cell-based two hybrid protein-protein interaction assay is constructed, wherein one of two fusion hybrid proteins in a cell contains an "A" subunit of calcineurin, and the other of two fusion hybrid proteins contains a CNI polypeptide. The cell preferably, but not necessarily, also contains a vector construct causing overexpression, or increased expression, of a "B" subunit of calcineurin. The cell is then contacted with the small molecule being tested. A small molecule is identified as an immunosuppressant if the molecule potentiates an interaction between the two hybrid proteins. This method is used to identify compounds (like FK506) that potentiate the interaction between CNI and CNA1. In one embodiment, the method is carried out using yeast cells, where one of the two fusion hybrid proteins contains a GAL4 activation domain and the other of two fusion hybrid proteins contains a GAL4 binding domain. The method can be carried out where subunits of calcineurin are from any cell source, in particular, yeast or mammalian cells (including human cells). The subunits may, for example, be calcineurin subunit A1 or A2. The CNI polypeptide may also be from any source (e.g., yeast or human), and may be only a fragment of a complete CNI polypeptide (such as a c-terminal fragment). An exemplary c-terminal fragment of CNI is CNIc.

Further, included in the present invention, is a yeast cell carrying a mutation in the naturally-occurring copy of CNI, where the mutation prevents expression of a functional CNI protein from the genomic copy. Embodiments of this aspect of the present invention include deletion mutations within the coding region of the CNI gene, deletion of regulation regions of the CNI gene, and non-sense or mis-sense mutations in the CNI gene. Yeast cells having such mutations are useful, for example, in a method of identifying proteins of similar function to CNI. In one embodiment, a hybrid interaction screen is set up in a cell with a CNI deletion and a GAL4 protein binding domain-CNA fusion and a GAL4 activation domain-immunophilin fusion. Expression libraries are then screened to identify clones encoding proteins that potentiate an interaction of an immunophilin with calcineurin. This screen will identify CNI-coding sequences as well as other proteins with a similar function.

In a related embodiment, a yeast cell with a CNI deletion is used to identify CNI homologues (e.g., from other organisms, such as human) using a complementation assay or screen. Expression libraries (e.g., human lymphocyte expression libraries) are transformed into cells with a CNI deletion, and transformants are selected on their ability to complement the function of yeast CNI. An exemplary assay for selecting such transformants is exposure to hygromycin B. Cells which become more sensitive to hygromycin B following transformation are further analyzed to determine if the plasmid with which they were transformed contains an insert homologous to yeast CNI, or encoding a polypeptide with similar function to CNI.

These and other objects and features of the invention will be more fully appreciated when the following detailed description of the invention is read in conjunction with the accompanying drawings.

BRIEF DESCRIPTION OF THE FIGURES

FIGS. 1A and 1B present schematic diagrams of sequences encoding the c-terminal portion of CNI (CNIc) fused to GAL-4 activation domain (GAL-4AD) (FIG. 1A), and sequences encoding CNI (FIG. 1B).

FIG. 2A presents data from a $\beta$-galactosidase ($\beta$-gal) assay to detect the interaction of CNIc with the A1 subunit of calcineurin (CNA1), A2 subunit of calcineurin (CNA2), GAL-4 binding domain (G4BD) and lamin C. A labeled schematic diagram corresponding to the data shown in FIG. 2A is presented in FIG. 2B to facilitate reference to individual groups of colonies.

FIGS. 7A, 7C, 7E and 7G present data from $\beta$-gal assays to evaluate the effects of FK506, cyclosporin A (CsA), rapamycin and the overexpression of CNB1 on the interaction of CNIc with CNA and CNAΔC. Labeled schematic diagrams corresponding to the data shown in FIGS. 7A, 7C, 7E and 7G are presented in FIGS. 7B, 7D, 7F and 7H, respectively.

FIG. 12 presents the DNA sequence of a 3.5 kb fragment of yeast chromosome 11 containing the coding sequence for a yeast CNI protein.

FIG. 13 presents the amino acid sequence of a yeast CNI protein.

BRIEF DESCRIPTION OF THE SEQUENCES

Figure 3A:
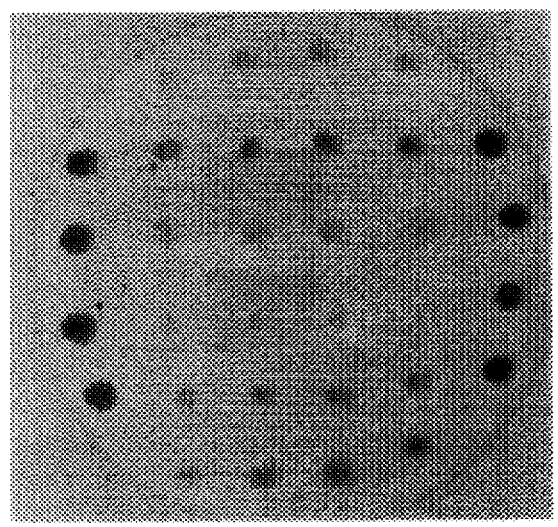
FIG. 3A presents data from a $\beta$-gal assay to detect the interaction of CNIc with CNA1ΔC, CNA2ΔC and CNB1. A labeled schematic diagram corresponding to the data shown in FIG. 3A is presented in FIG. 3B.

SEQ ID NO:1 presents the nucleotide sequence of a Sau3AI fragment containing the coding sequence for CNIc.

SEQ ID NO:2 presents the amino acid sequence of CNIc encoded by SEQ ID NO:1.

SEQ ID NO:3 presents the coding sequence presented in SEQ ID NO:1.

SEQ ID NO:4 presents the nucleotide sequence of a gene encoding a complete CNI protein.

SEQ ID NO:5 presents the amino acid sequence encoded by SEQ ID NO:4.

SEQ ID NO:6 presents the coding sequence presented in SEQ ID NO:4.

SEQ ID NO:7 presents the nucleotide sequence of PCR primer CNI-PCR-A.

SEQ ID NO:8 presents the nucleotide sequence of PCR primer CNI-PCR-B.

SEQ ID NO:9 presents the nucleotide sequence of a gene encoding the yeast CNA1 subunit of calcineurin.

SEQ ID NO:10 presents the amino acid sequence encoded by SEQ ID NO:9.

SEQ ID NO:11 presents the nucleotide sequence of a gene encoding the yeast CNA2 subunit of calcineurin.

SEQ ID NO:12 presents the amino acid sequence encoded by SEQ ID NO:11.

SEQ ID NO:13 presents the nucleotide sequence of a gene encoding the yeast CNB1 subunit of calcineurin.

SEQ ID NO:14 presents an amino acid sequence encoded by SEQ ID NO:13.

SEQ ID NO:15 presents an amino acid sequence encoded by SEQ ID NO:13.

SEQ ID NO:16 presents the coding sequence presented in SEQ ID NO:13.

SEQ ID NO:17 presents the amino acid sequence encoded by SEQ ID NO:16.

SEQ ID NO:18 presents a nucleotide sequence encoding CNA1Δc.

SEQ ID NO:19 presents the amino acid sequence encoded by SEQ ID NO:18.

SEQ ID NO:20 presents a nucleotide sequence encoding CNA2Δc.

SEQ ID NO:21 presents the amino acid sequence encoded by SEQ ID NO:20.

SEQ ID NO:22 presents the nucleotide sequence of PCR primer G4-PCR-A.

SEQ ID NO:23 presents the nucleotide sequence of PCR primer G4-PCR-B.

DETAILED DESCRIPTION OF THE INVENTION

I. DEFINITIONS

A "calcineurin-targeted immunosuppressant" is a compound that possesses in vivo immunosuppressive activity, and that interacts with an immunophilin to form a complex which is capable of inhibiting calcineurin.

"Interacting proteins" are proteins capable of specifically binding to one another, or associating with one another, in a cell or in vitro.

A calcineurin interacting (CNI) protein or polypeptide is a protein or polypeptide that is effective to enhance immunosuppressive effects of a calcineurin-targeted immunosuppressant by potentiating an interaction of an immunophilin with calcineurin. Preferably, a CNI protein or polypeptide is a protein or polypeptide having an amino acid sequence that is homologous to the sequence presented herein as SEQ ID NO:5.

"Substantially isolated" is used in several contexts and typically refers to the at least partial purification of a CNI protein or polypeptide fragment away from unrelated or contaminating components (e.g., cytoplasmic contaminants and heterologous proteins). Methods and procedures for the isolation or purification of compounds or components of interest are described below (e.g., affinity purification of fusion proteins and recombinant production of CNI polypeptides).

In the context of the present invention, the phrase "nucleic acid sequences," when referring to sequences which encode a protein, polypeptide, or peptide, is meant to include degenerative nucleic acid sequences which encode homologous protein, polypeptide or peptide sequences as well as the disclosed sequence.

Two nucleic acid fragments are considered to have "homologous" sequences if they are capable of hybridizing to one another (i) under typical hybridization and wash conditions, as described, for example, in Sambrook, et al., pages 320–328, and 382–389, or (ii) using reduced stringency wash conditions that allow at most about 25–30% basepair mismatches, for example: 2 x SSC, 0.1% SDS, room temperature twice, 30 minutes each; then 2 x SSC, 0.1% SDS, 37° C. once, 30 minutes; then 2 x SSC, room temperature twice, 10 minutes each. Preferably, homologous nucleic acid strands contain 15–25% basepair mismatches, even more preferably 5–15% basepair mismatches. These degrees of homology can be selected by using wash conditions of appropriate stringency for identification of clones from gene libraries (or other sources of genetic material), as is well known in the art.

Two amino acid sequences or two nucleotide sequences (in an alternative definition for homology between two nucleotide sequences) are considered homologous (as this term is preferably used in this specification) if they have an alignment score of >5 (in standard deviation units) using the program ALIGN, typically default mutation gap matrix and gap penalty (Dayhoff). The two sequences (or parts thereof) are more preferably homologous if their amino acids are greater than or equal to 40% identical using the ALIGN program mentioned above.

II. OVERVIEW OF INVENTION

Experiments performed in support of the present invention demonstrate the identification and isolation of the nucleic acid sequence encoding a calcineurin interacting (CNI) protein. Further experiments performed in support of the present invention characterize the CNI protein, as well as a polypeptide containing only the c-terminal 306 amino acids of the CNI protein (CNIc). The experiments demonstrate that CNIc interacts specifically with the "A" subunits of calcineurin (CNA1 and CNA2), but not with calcineurin "B" subunit (CNB1). The experiments also demonstrate that CNIc does not interact directly with FK506 binding protein (FKBP; Schreiber, et al.; with or without FK506), GAL4 binding domain ($G4_{BD}$) or lamin C. The experiments also demonstrate that CNIc interacts with C-terminally truncated forms of CNA (CNAΔC), which have lost their autoinhibitory domains, though the interaction is somewhat weaker that with full length CNA proteins.

Additional experiments show that the interaction between CNIc and CNA is enhanced when CNB1 is deleted, and diminished when CNB1 is overexpressed, that the interaction between CNIc and CNA or CNAΔC is markedly enhanced by FK506 and by Cyclosporin A (CsA), but not rapamycin, and that overexpression of a full-length CNI protein enhances the interaction between CNA and FKBP (detectable only in the presence of FK506).

Additional experiments conducted in support of the present invention demonstrate that overexpression of the full-length CNI has no detectable effect on the interaction between CNB1 and CNA, and that in the presence of FK506 or CsA, overexpression of CNB1 no longer inhibits the interaction of CNIc with CNA.

It was also found that CNI deletion mutants are viable, both in wild-type and CN-deletion backgrounds, and that CNI deletion mutants in a CN-deletion background are more resistant to hygromycin B than normal CN-deletion mutants.

Co-immunoprecipitation experiments demonstrate that CNIc and CNA co-immunoprecipitate in the presence of FK506, and protein blot experiments show that CNI is expressed at low levels in vivo. RNA blot experiments show that CNI is encoded by a single message approximately 2.9 kb in length.

A comparison of the yeast CNI sequence with sequences present in nucleic acid and amino acid databases reveals no obvious homologous sequences have been identified in other organisms.

III. CALCINEURIN

Experiments performed in support of the present invention were designed to identify polypeptides capable of interacting with calcineurin. Calcineurin (also called phosphoprotein phosphatase 2B or PP2B), has been characterized from many different tissues and organisms (Klee, et al.). It is a heterodimer of two subunits, of which the "A" subunit is about 61 kD in weight, possesses catalytic activity and also contains the association site for calmodulin. The "B" subunit contains four Ca2+ binding sites and activates the A subunit. Calcineurin has little enzymatic activity, even in the presence of Ca2+ and only becomes fully active when associated with calmodulin (Cyert).

Two A subunits (CNA1 and CNA2; Cyert, et al., 1991) and one B subunit (CNB1, Cyert, et al., 1992) have been cloned in yeast. Either CNA1 or CNA2 may associate with CNB1 to form a functional calcineurin heterodimer. Multiple isotypes of the A subunit have been cloned from a variety of organisms and are highly conserved (Klee, et al.). In particular, calcineurin subunits have been cloned from human tissue (see reviews by, for example, Klee, et al., and Guerini, et al.).

IV. IMMUNOSUPPRESSANT DRUGS

FK506, cyclosporin A (CsA) and rapamycin, derived from fungi, inhibit the activation of T-cells by antigens. The compounds have proven highly effective at suppressing mammalian immune systems in vivo. In particular, CsA therapy in clinical settings has dramatically increased the success rate of transplantation therapy.

It is now known that FK506 and CsA exert their immunosuppressive effects, in part, by inhibiting the transcriptional activation of the interleukin-2 (IL-2) gene, whereas rapamycin appears to function by inhibiting the response of T-cells to IL-2, presumably by inhibiting a transduction pathway mediated by the IL-2 receptor.

The molecular mechanism of FK506 and CsA immunosuppressive action involves a group of small, abundant intracellular proteins termed immunophilins, which bind with a high affinity to the immunosuppressants (Schreiber). At least two classes of immunophilins are known to exist. One class, termed cyclophilins, binds to CsA, while another class, the FK506-binding proteins (FKBPs) binds FK506 and rapamycin. Many immunophilin genes, from a variety of organisms, have been cloned, and appear to be highly conserved from simple eukaryotes to mammals.

It is believed that FK506 and CsA-induced immunosuppression is due to the binding of complexes, formed by binding of immunosuppressants FK506 and CsA bound to one of their respective immunophilins, to the catalytic subunit of calcineurin (Schreiber, et al., Liu, et al., Foor, et al., Weiss, et al.). The binding of such a complex to an (A) subunit inhibits activation of calcineurin by increased intracellular calcium, which in turn prevents calcineurin from activating transcription factor NF-AT. Since IL-2 is one of the genes controlled by NF-AT in T-cells, inhibition of the transcription factor inhibits the production of IL-2, resulting in immunosuppression (Clipstone, et al.).

FK506 and CsA are widely used in organ transplantation to prevent host rejection. However, both drugs are known to have many undesired side-effects such as neurotoxicity, nephrotoxicity, hypertension, and metabolic disorder. Accordingly formulations effective to increase a target cell's sensitivity to these drugs may be useful in alleviating some of the aforementioned side-effects. Specifically, CNI and its homologues or derivatives, administered at appropriate levels, may be able to increase the sensitivity of CN to FK506/CsA and reduce the necessary dosage thus reducing or eliminating the side-effects of these drugs.

V. TWO HYBRID PROTEIN INTERACTION ASSAYS

Two hybrid protein interaction assay methods (two hybrid protein-protein interaction screens) provide a simple and sensitive means to detect the interaction between two proteins in living cells. The assays are based on the finding that most eukaryotic transcription activators are modular (e.g., Brent, et al.), i.e., that the activators typically contain activation domains that activate transcription, and DNA binding domains that localize the activator to the appropriate region of a DNA molecule.

The development of two hybrid protein interaction assays was made possible by the observation that the DNA binding domain does not need to be physically located on the same polypeptide as the activation domain (Ma, et al., Triezenberg, et al.), raising the possibility that transcription of reporter genes could be used as an assay to detect protein interactions.

The utility of two hybrid systems for detecting interactions between two interacting proteins was fully realized by the observation that protein interactions could be detected if two potentially-interacting proteins were expressed as fusions, or chimeras (Fields, et al.). A first fusion protein contains one of a pair of interacting proteins fused to a DNA binding domain, and a second fusion protein contains the other of a pair of interacting proteins fused to a transcription activation domain. The two fusion proteins are independently expressed in the same cell, and interaction between the "interacting protein" portions of the fusions reconstitute the function of the transcription activation factor, which is detected by activation of transcription of a reporter gene.

At least two different cell-based two hybrid protein-protein interaction assay systems have been used to assess binding interactions and/or to identify interacting proteins. Both employ a pair of fusion hybrid proteins, where one of the pair contains a first of two "interacting" proteins fused to a transcription activation domain of a transcription activating factor, and the other of the pair contains a second of two "interacting" proteins fused to a DNA binding domain of a transcription activating factor.

The yeast GAL4 two hybrid system (Fields, et al., Chien, et al., Durfee, et al., Bartel, et al.), utilized for experiments performed in support of the present invention, was developed to detect protein-protein interaction based on the reconstitution of function of GAL4, a transcriptional activator from yeast, by activation of a GAL1-lacZ reporter gene.

Like several other transcription activating factors, GAL4 contains two distinct domains, a DNA binding domain and a transcription activation domain. Each domain can be independently expressed as a portion of a fusion protein composed of the domain, and a second, "bait" interacting protein. The two fusion proteins are then independently expressed together in a cell. When the two GAL4 domains are brought together by a binding interaction between the two "interacting" proteins, transcription of a reporter gene under the transcriptional control of GAL4 is initiated. The reporter gene typically has a promoter containing GAL4 protein binding sites (GAL upstream activating sequences, UAS$_G$). Exemplary reporter genes are the GAL1-lacZ, and GAL1-HIS3 reporter genes used in experiments described herein.

A second two hybrid system, described in detail in Ausubel, et al., utilizes a native E. coli LexA repressor protein, which binds tightly to appropriate operators. A plasmid is used to express one of a pair of interacting proteins (the "bait" protein) as a fusion to LexA. The plasmid expressing the LexA-fused bait protein is used to transform a reporter strain of yeast, such as EGY48, that contains pSH18-34.

In this strain, binding sites for LexA are located upstream of two reporter genes. In the first reporter system, the upstream activation sequences of the chromosomal LEU2 gene—required in the biosynthetic pathway for leucine (Leu)—are replaced in EGY48 with lexA operators, permitting selection for viability when cells are plated on medium lacking Leu. In the second reporter system, EGY48 harbors a plasmid, pSH18-34, that contains a lexA operator-lacZ fusion gene, permitting discrimination based on color when the yeast is grown on medium containing Xgal (Ausubel, et al.).

To screen a library with the LexA system, the library uses the inducible yeast GAL1 promoter to express proteins as fusions to an acidic domain ("acid blob") that functions as a portable transcriptional activation motif ("act"), and to other useful moieties. Expression of library-encoded proteins is induced by plating transformants on medium containing galactose (Gal), so yeast cells containing library proteins that do not interact specifically with the bait protein fail to grow in the absence of Leu. Yeast cells containing library proteins that interact with the bait protein form colonies within 2 to 5 days, and the colonies turn blue when the cells are streaked on medium containing Xgal. The plasmids are isolated and characterized by a series of tests to confirm specificity of the interaction with the initial bait protein. Those found to be specific are ready for further analysis (e.g., sequencing).

LexA and GAL4 each have different properties that should be considered when selecting a system. LexA is derived from a heterologous organism, has no known effect on the growth of yeast, possesses no residual transcriptional activity, can be used in GAL4$^+$ yeast, and can be used with a Gal-inducible promoter. Because GAL4 is an important yeast transcriptional activator, experiments must be performed in gal4$^-$ yeast strains to avoid background from endogenous GAL4 activating the reporter system.

Both two hybrid systems have been successfully used for isolating genes encoding proteins that bind a target protein and as simple protein binding assays (e.g., Yang, et al., Gyuris, et al.), and both can be applied to methods of the present invention.

Both gene isolation and protein binding assay applications of the GAL4 system are described in Examples below.

VI. SPECIFIC EMBODIMENTS

Example 1 demonstrates application of an exemplary two hybrid protein-protein interaction screen (Materials and Methods, section D) to the screening of three pGAD yeast fusion libraries, carrying fusions between the transcription activating domain of yeast protein GAL4 (G4AD) and yeast genomic DNA Sau3A1 fragments, in all three reading frames. The libraries are screened to identify polypeptides, encoded by the Sau3A1 fragments, capable of interacting with catalytic (A) subunits of calcineurin, expressed as fusions with the GAL4 protein binding domain (GBT-CNA fusions).

Three sets of yeast cells harboring pGBT-CNA1 TRP1 (GBT-A1) hybrid plasmid and a GAL4-activated LacZ reporter gene are each transformed with one of the three reading-frame libraries. Construction of the plasmids used is described in Materials and Methods, sections B and C. Cells transformed with a plasmid encoding a protein fusion capable of interacting with the CNA subunit fusion are selected using a β-galactosidase (β-gal) assay on plates containing the chromogenic substrate X-gal (Materials and Methods, section E). Results of the β-gal assay are confirmed using a growth assay (Materials and Methods, section F). False positives are eliminated by colony purification (re-streaking for single colonies), PCR experiments using GAL4 primers, and testing against a number of test fusions by β-gal assays on transformed haploid or mated diploid reporter strains.

A yeast clone encoding a polypeptide capable of specifically interacting with CNA polypeptide fusions is identified and sequenced. The sequence of the Sau3AI fragment is presented as SEQ ID NO:1. The coding sequence forming the open reading frame is presented as SEQ ID NO:3. The polypeptide encoded by the open reading frame is presented as SEQ ID NO:2. The open reading frame encodes 306 amino acids followed by a stop codon in frame with the coding sequence of GAL4, but does not contain an in-frame ATG start site upstream of the stop codon. This is consistent with the fragment encoding a c-terminal portion of a complete gene product. The clone is termed CNIc, with the lowercase "c" representing "c-terminal".

FIG. 1A shows a schematic representation of the nucleic acid sequence encoding the GAL4AD-CNIc fusion protein. The stippled portion between GAL4AD and CNIc represents a linker discussed in the Materials and Methods section, as well as in Example 1. Also indicated in the Figure are the approximate locations of in-frame start (ATG) and stop codons, and Sau3AI restriction sites.

Example 1 further describes the identification of a λ clone encoding a full length sequence version of CNIc, termed CNI. The polypeptide encoded by the sequence is termed CNI protein. The clone is identified by hybridization screening of a panel of λ clones spanning the yeast genome using a 1.22 kb $^{32}$P-labeled probe generated from CNIc.

Phage lysates of the λ clone are amplified, purified, restriction-mapped and used as a DNA source for subsequent cloning experiments. A 3.16 kb MunI/EcoRV fragment from the λ clone insert contains the coding sequence of CNI. The sequence of the 3.16 kb MunI/EcoRV fragment is encompassed by the 3.5 kb sequence presented as SEQ ID NO:4, and a schematic diagram of the sequence is shown in FIG. 1B. This sequence contains the entire 2.75 kb coding sequence of CNI (SEQ ID NO:6; graphically indicated in FIG. 1B by the locations of the "ATG" and "Stop" codons).

A search of known DNA and protein sequences turns up no obvious matches or homologies to genes in other organisms. Accordingly, CNI may represent a new type of calcineurin interacting protein.

The methods referred to above may also be applied to the screening of, for example, a human cDNA library using an appropriate two-hybrid protein interaction screen. The "bait" protein in the interaction screen (e.g., the protein analogous to CNA1 in Example 1) may be of yeast origin (e.g., CNA1), but is preferably of human origin (e.g., a human calcineurin "A" subunit; Klee, et al.). The bait protein is expressed in the cell (e.g., a yeast cell) used for the two hybrid interaction screen as a fusion to a domain of a transcription activating factor (e.g., the DNA binding domain of GAL4). The library may be a human DNA library in a vector (e.g., pGAD) effective to express library sequences as fusions to a complimentary domain of the transcription activating factor (e.g., the activation domain of GAL4). Libraries of human sequences can be derived from a number of sources including genomic DNA, such as yeast artificial chromosome (YAC) constructs carrying genomic human DNA, or cDNA generated from a variety of cell types (e.g., activated T-cells).

Example 2 details a β-gal assay to determine the specificity of binding of CNIc to subunits of calcineurin. Exemplary results are shown in FIG. 2A. The legend for FIG. 2A is shown in FIG. 2B. Numbers in the legend refer to locations of yeast colonies expressing particular combinations of plasmid constructs (indicated in Example 2).

A comparison of the intensities of the blue β-gal reaction product indicates that CNIc interacts strongly with CNA1 (21, 22 and 23), and somewhat less strongly with CNA2 (24). Neither cells containing AS-lamin with GAD-CNIc (25), nor cells containing only GBT with GAD-CNIc (26) show a detectable signal above background. Two subunits of calcineurin (CNA1, CNB1) known to interact with each other are used as a positive control for the assay (20). The data presented in FIG. 2A show that CNIc interacts specifically with CNA1 and CNA2, but not with G4BD or lamin C.

Figure 3B:
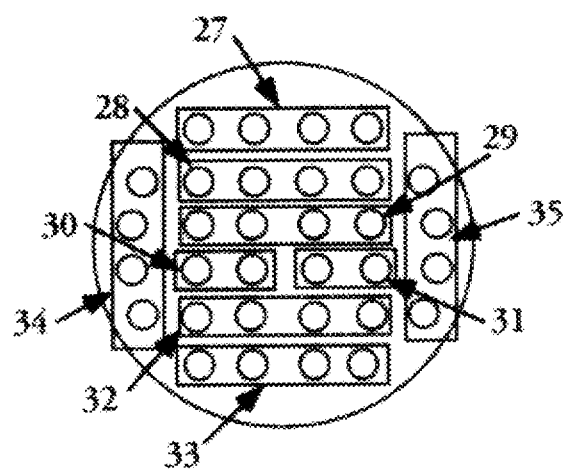

A similar set of experiments, illustrated in FIG. 3A, is conducted using constitutively-active CNA subunits, as well as calcineurin subunit CNB1. As described in the Materials and Methods section below, CNA1ΔC and CNA2ΔC are each missing a C-terminal portion of the protein containing an autoinhibitory domain. Exemplary results from these experiments are shown in FIG. 3A. The legend for FIG. 3A is shown in FIG. 3B.

The data show that GBT-A1ΔC and GAD-CNIc (28) gives a definite positive signal, while GBT-A2ΔC and GAD-CNIc (29) is weaker, though still detectable above its background (i.e. GBT-A2ΔC and GAD; 31). The signal from GBT-B1 and GAD-CNIc (32) is not detectable above vector background (GBT-B1 and GAD; 33). Positive controls GBT-A1ΔC and GAD-B1 (34) and GBT-A2ΔC and GAD-B1 (35) give strong signals. The data presented in FIG. 3A show that CNIc interacts specifically with CNA1ΔC and CNA2ΔC, but not with CNB1.

Example 3 details the effects of immunosuppressant drugs on binding of CNIc to calcineurin in B1$^{wt}$, B1 Deletion and B1 Overproducing Yeast Strains. The yeast strains are assayed for β-gal activity as above to determine if the immunosuppressant drugs FK506, cyclosporin A (CsA) and rapamycin affect the binding of CNIc to subunits of calcineurin. The experiments are performed in yeast strains wild-type for the CNB1 subunit, null for the CNB1 subunit, and in yeast transformed with a high efficiency expression vector containing DNA encoding the CNB1 subunit.

Figure 4A:
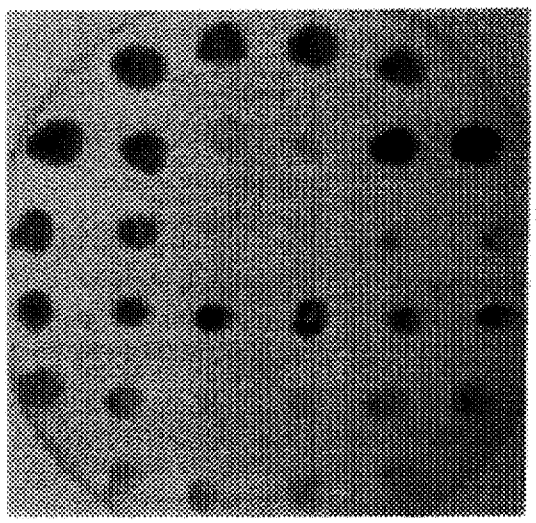
FIGS. 4A and 4C present data from $\beta$-gal assays to evaluate the effects of FK506 and the deletion of CNB1 on the interactions of CNIc with CNA and CNAΔC. Labeled schematic diagrams corresponding to the data shown in FIGS. 4A and 4C are presented in FIGS. 4B and 4D, respectively.
Figure 4C:
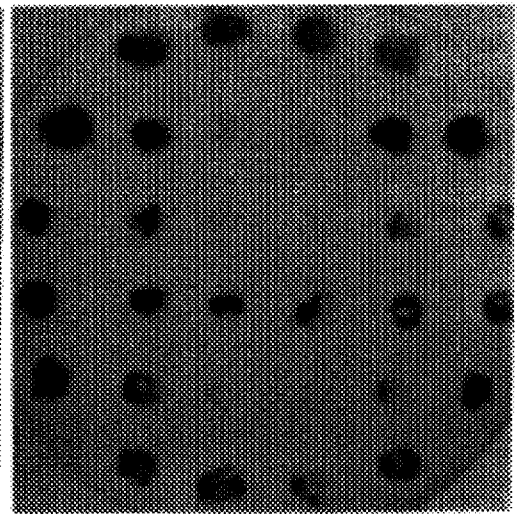
Figure 4B:
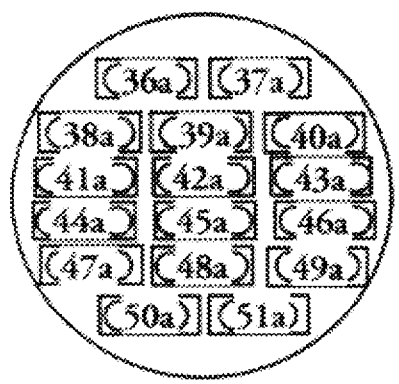
Figure 4D:
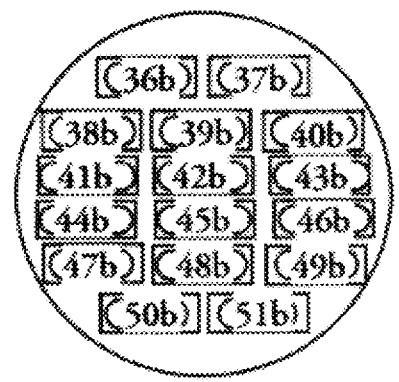
Figure 5A:
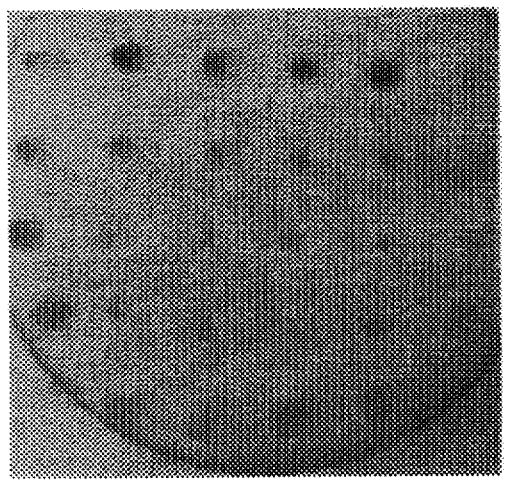
FIGS. 5A and 5C present data from $\beta$-gal assays to evaluate the effects of FK506 and the overexpression of CNB1 on the interactions of CNIc with CNA and CNAΔC. Labeled schematic diagrams corresponding to the data shown in FIGS. 5A and 5C are presented in FIGS. 5B and 5D, respectively.

Exemplary data are shown in FIGS. 4A, 4C, 5A and 5C. The legends for FIGS. 4A and 4C are shown in FIGS. 4B and 4D, respectively. FIGS. 4A and 5A illustrate experiment performed without FK506, while experiments shown in FIGS. 4C and 5C were performed with FK506.

The interactions of various combinations of proteins expressed by constructs indicated in Example 3 was studied in three yeast strains, one of which is null for the CNB1 subunit of calcineurin (Y153b; at 36–40), while the others (Y190; at 41–46 and Y526 at 47–51) are wild-type for CNA1, CNA2 and CNB1.

The data, shown in FIG. 4A (no added drugs), illustrate that deleting the endogenous host CNB1 gene potentiates, or enhances, interactions between CNIc and calcineurin subunits CNA1, CNA2, CNA1ΔC and CNA2ΔC. Comparison of corresponding colonies in FIGS. 4A and 4C shows the effects of FK506 on CNIc-CNA/CNAΔC interactions. The drug enhances interactions under all except control conditions. The effect is most striking in yeast strains wild-type for the CNB1 subunit (e.g., compare 50a with 50b, and 51a with 51b).

The drug also markedly enhances, or potentiates CNIc-CNA/CNAΔC interactions under conditions where the CNB1 subunit is overexpressed. FIG. 5A shows the effect of overexpressing CNB1 on CNIc-CNA/CNAΔC interactions in the absence of drug. Colonies expressing B1/YEp352 (53a, 55a–58a) have reduced signal as compared with controls expressing only YEp352 (52a, 54a). Inclusion of FK506 in the plating medium (FIG. 5C), however, enhances, or potentiates interactions in all colonies, except the negative controls (56).

The data presented in FIGS. 4A, 4C, 5A and 5C demonstrate that the interaction of CNIc with CNA and CNAΔC is markedly enhanced by FK506. The interaction is also enhanced by deletion of CNB1 and diminished by overexpression of CNB1, and the inhibitory effect of CNB1 overproduction is overcome by the stimulatory effect of FK506.

Stated another way, inclusion of a small molecule immunosuppressant (FK506) potentiates an interaction between two fusion hybrid proteins, where one of the two proteins contains an (A) subunit of calcineurin, and the other protein contains a CNI polypeptide. The potentiation is particularly strong when the cell is further modified to cause overexpression of a "B" subunit of calcineurin by said cell (e.g., the expresses B1/YEp352).

In the present case, a yeast cell is modified to cause overexpression of a "B" subunit of calcineurin (CNB1) by transforming the cell with B1/YEp352 (construction described below). A cell may be modified to cause overexpression of a "B" subunit of calcineurin in other ways as well, such as, for example, transformation with other types of expression vectors encoding a "B" subunit of calcineurin, or treatment with a substance that upregulates a promoter controlling expression of an endogenous (B) subunit of calcineurin.

In light of the effects of FK506 on CNIc-CNA/CNAΔC interactions, two other immunosuppressants, cyclosporin A and rapamycin, were examined in similar experiments. The results of these experiments are shown in FIGS. 6A–6F and 7A–7H.

Figure 6A:
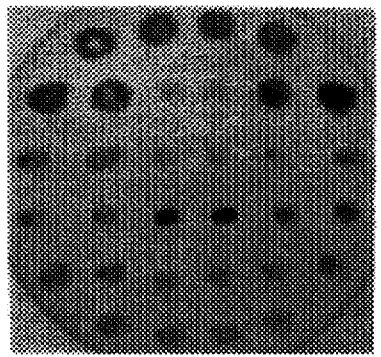
FIGS. 6A, 6C and 6E present data from $\beta$-gal assays to evaluate the effects of FK506, cyclosporin A (CsA), and the deletion of CNB1 on the interaction of CNIc with CNA and CNAΔC. Labeled schematic diagrams corresponding to the data shown in FIGS. 6A, 6C and 6E are presented in FIGS. 6B, 6D and 6F, respectively.
Figure 6C:
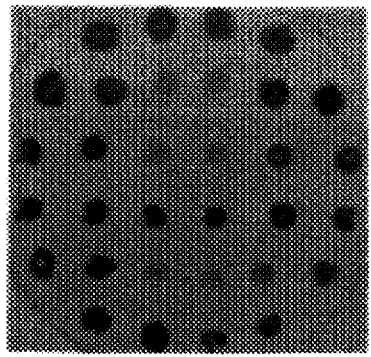
Figure 6E:
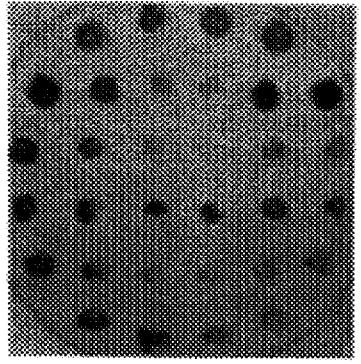

The data presented in FIGS. 6A and 6C are essentially equivalent to those presented in FIGS. 4A and 4C, respectively. Data shown in FIG. 6E demonstrate that like FK506, the immunosuppressant cyclosporin A is also effective to enhance interaction of CNIc with CNA and CNAΔC. Both FK506 and cyclosporin A are known to exert their immunosuppressive effects through calcineurin (Cyert).

Figure 5C:
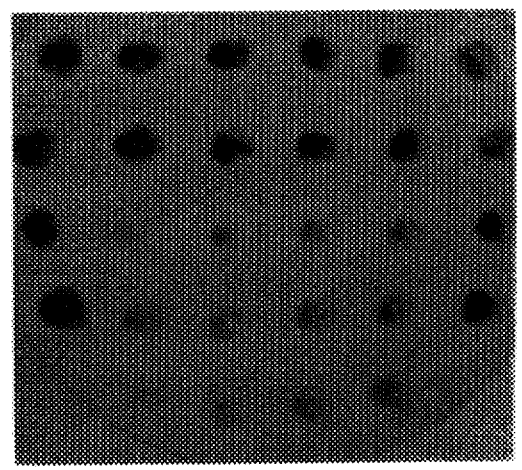

Similarly, data shown in FIGS. 7A and 7C support data in FIGS. 5A and 5C, and further, demonstrate that there is no detectable interaction between FK506 binding protein (FKBP) and CNIc. Results shown in FIG. 7E demonstrate that cyclosporin A has a similar effect to FK506 in cells overexpressing CNB1–that is, it enhances the interactions between CNIc and CNA/CNAΔC.

In contrast, data presented in FIG. 7G show that the immunosuppressant rapamycin has no detectable effect on CNIc-CNA/CNAΔC interactions (compare FIG. 7G with FIG. 7A).

Taken together, the data presented in FIGS. 6A, 6C, 6E 7A, 7C, 7E and 7G show that like FK506, cyclosporin A (CsA), but not rapamycin, enhances the interaction of CNIc with CNA and CNAΔC, and that CNIc doesn't interact with FKBP with or without FK506.

Figure 8A:
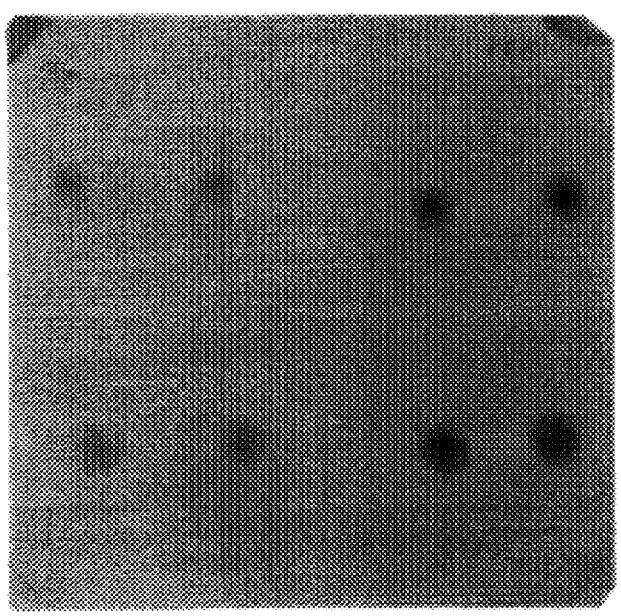
FIG. 8A presents data from a $\beta$-gal assay to evaluate the effects of overexpression of full-length CNI on FK506-dependent interaction of FKBP with CNA. A labeled schematic diagram corresponding to the data shown in FIG. 8A is presented in FIG. 8B.
Figure 8B:
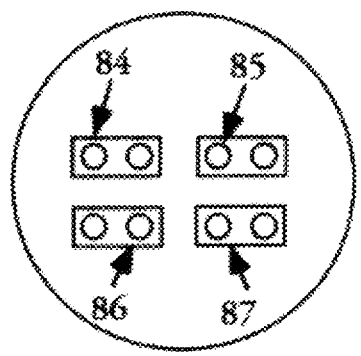

Example 4 describes experiments to assess effects of CNIc on FKBP/FK506 binding to calcineurin. FIG. 8A presents exemplary data from studies to assess the effect of CNI on FKBP-mediated FK506 interactions with CNA2. The legend for FIG. 8A is shown in FIG. 8B. Data in FIG. 8A demonstrate that, in the absence of FK506, FKBP and CNA2 show no detectable interaction (84). In the presence of FK506, however, the proteins interact (85), presumably because FK506 forms a complex with FKBP, which then binds CNA2 (Cyert).

Data in FIG. 8A further show that, in the absence of FK506, CNI has no effect on the lack of interaction between FKBP and CNA2 (86). In the presence of FK506 (87), however, CNI potentiates, or enhances the binding between FKBP and CNA2 (compare the intensity at 87 with that at 85). This effect suggests that CNI and similar compounds may be employed to increase the sensitivity of calcineurin to immunosuppressant drugs that act on it, and in this way, decrease the amount of the immunosuppressant required for a particular level of immunosuppression.

Figure 9A:
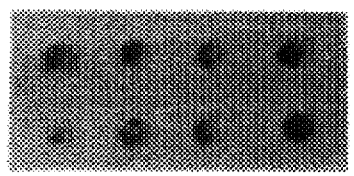
FIGS. 9A and 9C present data from $\beta$-gal assays to evaluate the effects of overexpression of full-length CNI on FK506-dependent interaction of FKBP with CNB1. Labeled schematic diagrams corresponding to the data shown in FIGS. 9A and 9C are presented in FIGS. 9B and 9D, respectively.
Figure 9B:
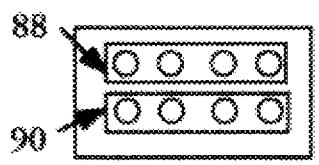
Figure 9C:
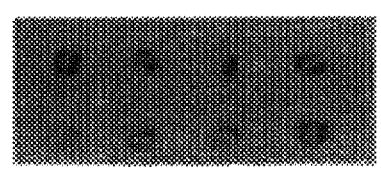
Figure 9D:
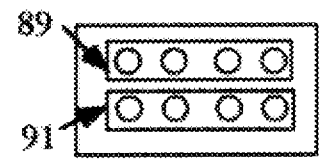

Experiments illustrated in FIGS. 9A and 9B demonstrate that FK506 has little or no effect on the binding of CNA to CNB1. The legends for FIG. 9A and 9B are shown in FIGS. 9B and 9D, respectively. The data in FIG. 9A show that overexpression of the full-length CNI clone markedly enhances the FK506-dependent interaction of FKBP with CNA, although it doesn't affect the interaction between CNA and CNB1.

Figure 10:
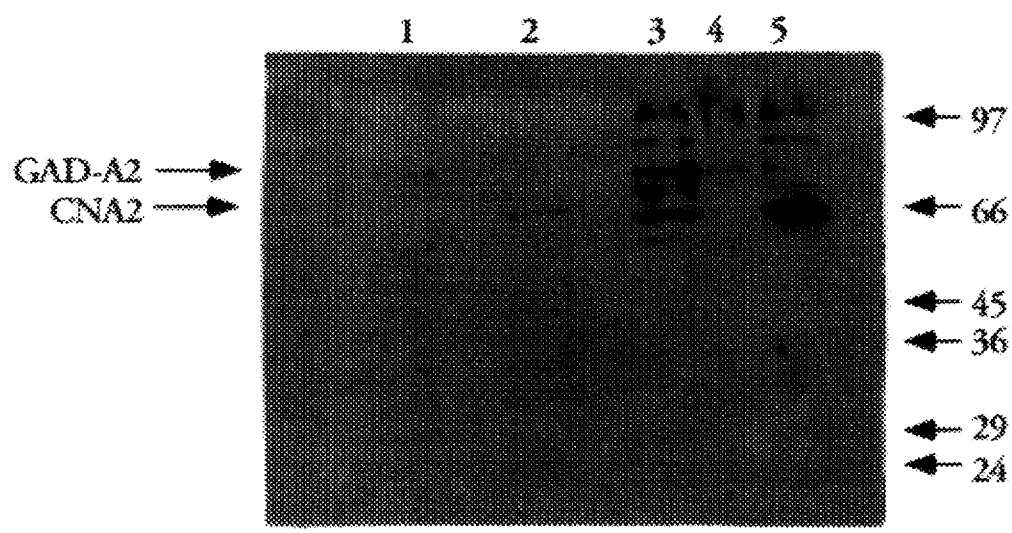
FIG. 10 presents an image of a protein blot of CNIc and CNA co-immunoprecipitate probed with anti-CNA2 antibody.

Example 5 presents co-immunoprecipitation of CNIc (carrying an HA epitope tag) and CNA. Immunoprecipitation is carried out with anti- HA monoclonal antibody and the immune complex, resolved by SDS-PAGE, is detected with anti-CNA2 polyclonal antibody and visualized with goat anti-rabbit antibody using the "ECL" method (Amersham, Arlington Heights, Ill.). The results, shown in FIG. 10, demonstrate that CNIc is capable of binding to CNA2 tightly enough for the complex to be co-immunoprecipitated. Similar methods may be employed to isolate a CNI analog from other cell sources, including mammalian (specifically human).

Figure 11:
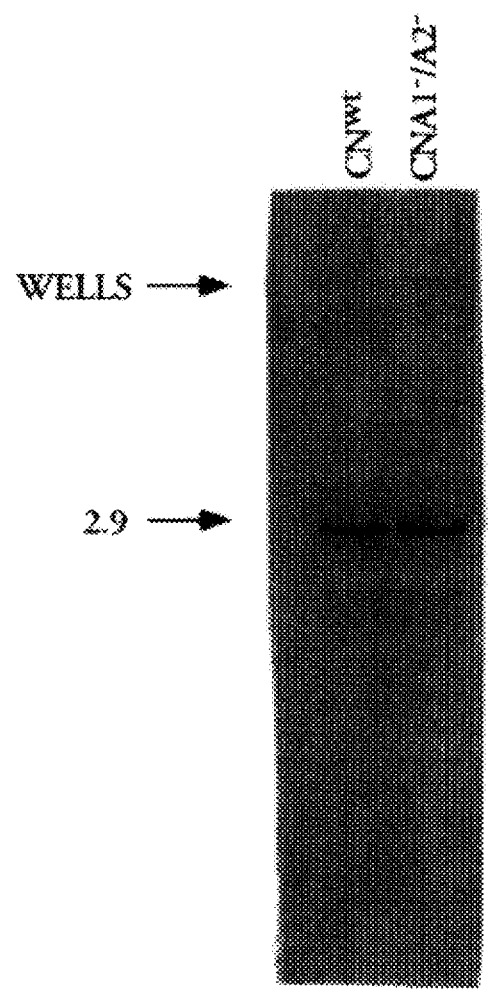
FIG. 11 presents an image of a yeast RNA blot hybridized with a CNIc probe.

Example 6 describes yeast RNA blots hybridized with a CNIc probe. Exemplary data are shown in FIG. 11. A single message of approximately 2.9 kb is detected. The data indicate that CNI is an expressed gene encoding a 2.9 kb message in yeast.

Example 8 details the construction of cni null mutants. The null mutants are employed to assess if CNI is required for viability in yeast, and to test hygromycin B sensitivity. The experiments indicate that CNI is not essential for viability, since CNI deletion mutant strains can survive, but that CNI deletions render a host more resistant to hygromycin B. The effect is particularly pronounced in both MCY300-1 (cna1⁻cna2⁻) and DD12 (cnb1⁻), suggesting that CNI functions as a suppressor of CN mutant's sensitivity to hygromycin B.

It will be understood that all of the above methods and experimental manipulations are amenable to being done with interacting polypeptides from organisms other than yeast. In particular, calcineurin subunits, CNI polypeptides, immunophilins and the like may be of mammalian origin, e.g., human origin.

VII. UTILITY

Methods and compositions of the present invention may be applied in a number of different ways. Following the guidance presented herein, one of skill in the art may isolate nucleic acids encoding additional CNI polypeptides, for example, a human CNI polypeptide.

In one approach, a yeast strain carrying a mutation of the CNI gene, e.g., a deletion, is used to clone heterologous sequences (e.g., human sequences) by complementation. A library of genomic DNA or, preferably, cDNA from an organism (e.g., human) and tissue (e.g., lymphocyte cells) of choice is cloned into a vector that can be maintained in yeast. Preferably, the vector contains a yeast promoter effective to express the heterologous sequences in yeast cells. Several heterologous libraries suitable for expression in *Saccharomyces cerevisiae* containing DNA from *S. pombe* (Beach, et al.) and Drosophila have been constructed.

The library is transformed into a suitable yeast strain carrying a cni mutation, and transformants are selected using a suitable complementation assay. For example, transformants may be screened for increased hygromycin sensitivity, as experiments described herein indicate that cni deletion mutants possess a decreased sensitivity to hygromycin B (Example 8). The screen may be made more effective by using a yeast strain that is hypersensitive to hygromycin B, such as a strain deficient for a subunit of calcineurin (Example 8).

Alternatively, human CNI DNA sequences may be isolated by directly screening a library, e.g., a lymphocyte cDNA library, for clones hybridizing with a yeast CNI nucleic acid probe. The generation of an exemplary yeast CNI nucleic acid probe is described in Example 1.

In another approach, particularly advantageous for isolating sequences expressed at low levels, a CNI nucleic acid probe may be used to screen a genomic library, e.g., a human genomic library, to isolate a sequence that may be used to design probes or primers that may match the target sequence better that the yeast sequence. Such primers may be used with, for example, PCR, to isolate longer fragments from a tissue-specific library.

In yet another approach, an antibody generated against CNI polypeptide is used to immunoprecipitate a CNI polypeptide from an organism and/or tissue of choice. The protein may then be micro-sequenced, and the sequence utilized to design degenerate primers useful for isolating a cDNA.

CNI polypeptides of the present invention, particularly CNI fragments that retain a desired binding activity, may be used as lead compounds useful for the development of small molecules having cellular functions similar to those of the CNI-polypeptides, that is, molecules effective to enhance immunosuppressive effects of calcineurin-targeted immunosuppressants by potentiating an interaction of an immunophilin with calcineurin.

CNI-polypeptides of the present invention may also be employed in a method of increasing sensitivity of cells to calcineurin-affecting immunosuppressant drugs. In this method, a CNI-polypeptide is introduced into the cell typically prior to or at the same time as contacting the cell with an immunosuppressant drug, such as FK506. The polypeptide may be delivered by any suitable means effective to deliver polypeptides to selected cells.

Alternatively, nucleic acids encoding CNI polypeptides may be used in appropriate expression vectors as a genetic therapy tool to potentiate the immunosuppressive effects of calcineurin-targeting immunosuppressant drugs. The vectors may be targeted to selected cells, such as T-cells, to increase their sensitivity to a given systemic dose of an immunosuppressant.

Another utility of the present invention includes methods of screening for substances that up-regulate expression of CNI polypeptides, i.e., substances that affect transcription. Such substances are useful for sensitizing cells to immunosuppressant drugs. In this method, the CNI promoter can be attached to a gene that functions as a selectable marker (for use in genetic selections to screen test substances) or to a reporter gene (for use in evaluating the effect on CNI transcription by test substances).

In another aspect of the present invention, the CNI-polypeptides, for example, mammalian homologue polypeptides of CNI, have potential use as therapeutic agents for both human and veterinary use. For example, CNI-polypeptides may be used in a method of enhancing immunosuppression in a test subject. In this method, the CNI-polypeptide is administered to the subject in a pharmaceutically-acceptable formulation and at a concentration effective to potentiate the interaction of an immunosuppressant/immunophilin complex with a subunit of calcineurin. The method may also include contacting the CNI-polypeptide with a cell under conditions effective to permit uptake of the protein into the cell in order to increase sensitivity of the cell to immunosuppressants. A CNI polypeptide used in such methods may be modified to be more suitable for administration or to be more effective in a cell. For example, a CNI polypeptide may be modified to eliminate PEST motifs, which are typically found in proteins with short half-lives, to extend the effective lifetime of the polypeptide in the target cell.

The following examples illustrate, but in no way are intended to limit the present invention.

MATERIALS AND METHODS

Unless indicated otherwise, chemicals and reagents were obtained from Sigma Chemical Company (St. Louis, Mo.) or Mallinckrodt Specialty Chemicals (Chesterfield, Mo.), restriction endonucleases were obtained from New England Biolabs (Beverly, Mass.), and other modifying enzymes and biochemicals were obtained from Pharmacia Biotech (Piscataway, N.J.) or Boehringer Mannheim (Indianapolis, Ind.). FK506 was obtained from Fujisawa USA, Inc. (Deerfield, Ill.), cyclosporin A was obtained from Sandoz (Basel, Switzerland), and rapamycin was obtained from Wyeth-Ayerst (Princeton, N.J.). Materials for media for yeast growth and culture were obtained from DIFCO (Detroit, Mich.). Unless otherwise indicated, manipulations of yeast, bacteria, nucleic acids, proteins and antibodies were performed using standard methods and protocols (e.g., Guthrie, et al., Sambrook, et al., Ausubel, et al., Harlow, et al., and Rose, et al.).

A. Buffers

Z buffer: 60 mM $Na_2HPO_4$—$7H_2O$, 40 mM $Na_2PO_4$—$H_2O$, 10 mM KCl, 1 mM $MgSO_4$—$7H_2O$ and 50 mM β-mercaptoethanol (pH 7.0).

B. Plasmids, Libraries and Yeast Strains

Plasmids pGBT9 (GBT), carrying GAL4 DNA-binding domain (amino acid residues 1–147; G4BD) and TRP1, and pGAD (GAD), carrying GAL4 activation domain (amino acid residues 768–881; G4AD) and LEU2; three pGAD libraries carrying fusions between G4AD and yeast genomic Sau3AI partial-digest fragments in each frame; and the yeast GAL1-lacZ reporter strain SFY526 (Y526; MATa ura3-52 ade2-101 lys2-801 his3-200 trp1-901 leu2-3,112 can1 gal4-542 gal80-538 URA3::GAL1-lacZ) were obtained from Stanley Fields (State University of New York at Stony Brook, Stony Brook, N.Y.; Chien, et al., Bartel, et al.). The libraries were constructed with linkers between the GAL4 activation domain and the Sau3AI fragments. The sequences of the linkers were 5'-ATCG-3' for the first library, 5'-ATCCG-3' for the second library, and 5'-ATCCCG-3' for the third library. In this way, the yeast genomic Sau3AI fragments were cloned in all three reading frames relative to G4AD.

Plasmids pAS2 (AS) carrying G4BD and TRP1, and pAS-lamin (AS-lamin) containing a sequence encoding a G4BD-lamin C fusion; and yeast reporter strains Y190 (MATa ura3-52 ade2-101 his3-Δ200 trp1-901 leu2-3,112 cyh2Δ, gal4Δ gal80Δ URA3::GAL-lacZ LYS2::GAL-HIS3), a derivative of Y153 carrying dual indicator genes (GAL-lacZ and GAL-HIS3), and Y187 (MATα ura3-52 ade2-101 lys2-801 his3-200 trp1-901 leu2-3,112 gal4Δgal80ΔURA3::GAL-lacZ) carrying GAL-lacZ reporter were obtained from Stephen Elledge (Baylor College of Medicine, Houston, Tex.; Durfee, et al.). Yeast strain Y153b1 (cnb1::ADE2) was derived from Y153.

E. coli strain JBe181 (leuB600 trpC9830) was obtained from Ira Herskowitz (University of California at San Francisco, San Francisco, Calif.). Protease-deficient yeast strain BJ2407 (Guthrie, et al.) was obtained from the Yeast Genetic Center (University of California at Berkeley, Berkeley, Calif.).

C. GAL4-Calcineurin Fusions

GAL4-calcineurin (GAL4-CN) fusions, GBT-A1 (G4BD-CNA1), GBT-A2 (G4BD-CNA2), GBT-B1 (G4BD-CNB1), GAD-A1 (G4AD-CNA1), GAD-A2 (G4AD-CNA2), and GAD-B1 (G4AD-CNB1) were constructed as follows. Plasmids containing inserts encoding CN subunits CNA1 (SEQ ID NO:9; Cyert, et al., 1991), CNA2 (SEQ ID NO:11; Cyert, et al., 1991) and CNB1(SEQ ID NO:13; Cyert, et al., 1992) were subjected to site-directed mutagenesis (Kunkle) to introduce a BamHI site just upstream of each subunit's initiation codon in the second reading frame. DNA prepared from the mutated plasmids was digested with BamHI and XhoI, and the resulting BamHI-XhoI fragments, each containing a full-length coding sequence, were cloned into GBT or GAD that had been cut with BamHI and Sal I. The resulting plasmids encoded in-frame fusions of the CN subunits with G4BD or G4AD.

Plasmids encoding CNA protein variants with truncated C-termini (GBT-A1ΔC, GBT-A2ΔC) were constructed by introducing stop codons after amino acid residues 509 (CNA1) and 502 (CNA2). The 44-residue deletion in GBT-A1ΔC removed the autoinhibitory domain of CNA1, while the 102-residue deletion in GBT-A2ΔC removed both the autoinhibitory and the calmodulin-binding domains of CNA2 (Cyert, et al., 1991).

Plasmid GBT-FKBP, containing an FK506 binding protein (FKBP) gene fused to the GAL4 binding domain, was constructed by introducing a BglII site upstream of the initiation codon and a BamHI site downstream of the stop codon of FKBP12 (Heitman, et al.) and ligating the BglII-BamHI fragment into GBT cut with BamHI.

Plasmid B1/YEp352 was constructed to contain the full coding sequence of CNB1 (SEQ ID NO:13, Cyert, et al., 1992) as a 1.4 kb BamHI-EcoRI fragment encompassing the sequence presented as SEQ ID NO:13 (812 bp; contains the coding sequence), in the multicopy plasmid YEp352(HIS), which is derived from YEp352 (URA) (Hill, et al.).

Plasmid CNI/YEp352(HIS) (also referred to as CNIH) was constructed by ligating a 3.16 kb MunI-EcoRV fragment, containing the full coding sequence of CNI, from plasmid CNI7.1 (construction described below) into YEp352(HIS) cut with EcoRI and SmaI. Plasmids CNI/YEp352(TRP) (also referred to as CNIT) and CNI/YEp352 (URA) (also referred to as CNIU) were similarly constructed using the 3.16 kb fragment and YEp352(TRP) or YEp352 (URA), respectively (Hill, et al.).

Plasmids A1/YEp351 and A2/YEp352 were constructed to contain the full coding sequences of CNA1 (SEQ ID NO:9, Cyert, et al., 1991) in YEp351 (Hill, et al.) and CNA2 (SEQ ID NO:11, Cyert, et al., 1991) in YEp351 and YEp352, respectively. A1/YEp351 was constructed by ligating a 2.9 kb SacI-HindIII fragment from clone CNA1 (Cyert, et al., 1991) into YEp351 (HIS) cut with SacI and HindIII. A2/YEp352 was similarly constructed by ligating a 3 kb SpeI-HindIII fragment from clone CNA2 (Cyert, et al., 1991) into YEp352(HIS) cut with XbaI and HindIII.

All GAL4-CN fusions were verified by DNA sequencing (Sanger, et al.) using "SEQUENASE 2.0" sequencing kits (United States Biochemical, Cleveland, Ohio), and were subjected to the following tests. The functionality of the fusion proteins was assayed by determining whether they could complement the appropriate cn⁻ mutant phenotypes, using assays to measure the sensitivity to pheromone and $Mn^{2+}$ (Reneke, et al., Cyert, et al., 1991). All of the GAL4-CN fusions were functional in this assay.

The fusion proteins were also tested for their ability to activate the reporter gene in the absence of the complementary GAL-4 domain fusion (i.e., in the presence of the complementary GAL4 domain not fused to a second protein, for example, G4BD-A1 vs G4AD) using the two-hybrid interaction assay described below. Only GBT-B1 and GAD-A1 were able to activate the reporter gene at low levels without the complimentary GAL-4 domain fusion—assays with the other fusion proteins in the absence of the complimentary GAL-4 domain fusion showed no detectable levels of expression.

The two-hybrid interaction assay was also used to test the ability of the fusions to interact specifically with another fusion containing complimentary GAL4 and CN domains (e.g., G4BD-A1 interacting with G4AD-B1). All CN hybrids were able to react specifically and result in an activation of the reporter gene that was clearly detectable above background. The high specificity witnessed in these experiments indicates that the GAL4 two-hybrid system can reliably be used to assay interactions between CN and other proteins.

D. Yeast GAL4 Two-Hybrid System for Detecting Protein-Protein Interaction

In the library screen, described in more detail in Example 1A, the yeast strain Y190, harboring the hybrid plasmid carrying the GAL4 binding domain fused to the A1 subunit of calcineurin (G4BD-CNA1) was transformed with fusion libraries carrying yeast genomic DNA Sau3AI fragments fused to the GAL4 activation domain. Transformants that were able to express the reporter genes, i.e., able to grow on -His+3-AT and to score blue in β-gal assay, were selected as candidate positives. These candidate positives potentially contain library DNA fragments encoding proteins that physically interact with CNA1.

In another application described herein, the two-hybrid system was used to test for interactions between CNA (fused to one of the GAL4 domains) and CNB1 (fused to the other GAL4 domain), and between CNA and FKBP. Additional experiments tested a clone, CN1c, isolated using the library screen, against a series of proteins fused to the complementary GAL4 domain under various conditions to test whether CN1c interacts with CNA subunits, and if so, how the interactions are affected by various conditions.

E. Color Development (β-gal) Assay

Yeast reporters harboring both G4BD and G4AD fusions (and a third non-fusion plasmid in some cases) were monitored for β-gal activity as follows. Purified yeast transformants were patched onto selective plates with or without other test reagents. After growing 3 days at 30° C., colonies were lifted onto nitrocellulose filters, permeabilized in liquid nitrogen as above, placed on Whatman No. 1 paper in petri dishes containing 0.1% X-Gal in Z buffer (see above), and incubated at 30° C. for 12 hours. Blue color begins to appear in positive colonies between about one half and ten hours into the incubation period.

Exemplary images obtained using the color development assay are presented in FIGS. 2A, 3A, 4A, 4C, 5A, 5C, 6A, 6C, 6F, 7A, 7C, 7E, 7G, 8A, 9A and 9C.

F. Growth Assay

A growth assay, applicable to yeast strains Y190 and Y153b1 which carry both GAL-HIS3 and GAL-lacZ reporters, was sometimes used as a complement to the color assay described above. Yeast transformants were streaked onto selective plates containing 40–50 mM 3-AT and no Histidine, and incubated at 30° C. for 3–7 days. Growth (corresponding to the level of HIS3 expression) was monitored as an indicator of the interaction between fusion proteins. In cases where both assays were used, the amount of cell growth typically correlated well with the color intensity in the β-gal assay.

G. Yeast Growth, Drug Treatment

Yeast were typically grown in YPD (rich non-selective) or synthetic complete (SC) medium with selected component drop-outs, depending on the plasmid introduced, following standard procedures (Sherman, et al., Ausubel, et al.).

Experiments utilizing treatment with drugs or additives were performed by including the drug or additive in the medium. For plating, the agar was autoclaved, allowed to cool to 50° C., and the drug or additive was added before pouring the plates. Unless otherwise indicated, drugs and additives were added to result in the following final medium concentrations: FK506: 1 µg/ml, cyclosporin A: 10 µg/ml, rapamycin: 10 ng/ml, and hygromycin B: 40 µg/ml.

H. Antibodies

Polyclonal and monoclonal antibodies, for use in the present invention, can be prepared by standard methods (Harlow, et al.) utilizing the CNI polypeptides of the present invention, for example, a substantially purified CNI/β-galactosidase fusion protein (Example 9). Antibodies can also be generated by recombinant techniques (Cabilly, et al.; Better, et al.; Skerra, et al.). In addition to whole antibody molecules, antibody fragments retaining the immunological specificity of the whole antibody may also be used in the practice of the present invention (e.g., Fab and F(ab')₂ fragments of IgG (Pierce Chemical, Rockford, Ill.)). The antibodies can be purified by standard methods to provide antibody preparations which are substantially free of serum proteins that may affect reactivity (e.g., affinity purification (Harlow et al.)).

EXAMPLE 1

Isolation of CNIc

A. Library Screening

Yeast strain Y190 was transformed with pGBT-CNA1 TRP1 (GBT-A1) hybrid plasmid using the transformation protocol described by Schiestl, et al. Transformants were selected, colony purified, and a single transformant was selected to make (Y190 GBT-A1)-competent cells, following the procedure described in Guthrie, et al.

The three pGAD yeast fusion libraries described above, carrying fusions between G4AD and yeast genomic DNA Sau3A1 fragments in each reading frame, were then used to transform (Schiestl, et al.) the Y190 GBT-A1containing cells. Transformants were plated onto SC-Trp-Leu-His plates containing 40 mM 3-aminotriazole (3-AT; Sigma Chemical Co., St. Louis, Mo.) and incubated at 30° C. for 6 days to screen for HIS+ colonies (Durfee, et al.).

His+ colonies were replica plated onto nitrocellulose filters (Schleicher & Schuell, Keene, N.H.), frozen in liquid nitrogen for approximately 30 seconds, and incubated at 30° C. for 12 hours with Z buffer (see above) containing the chromogenic substrate X-Gal (0.1%) to assay β-gal activity (Breeden, et al.).

Candidate positive (blue) colonies were re-streaked for single colonies. Single colonies were purified and retested using the above protocol. Colonies which reproducibly tested positive were screened using PCR with primers directed against the internal portion of GAL-4 (i.e. the portion between the DNA binding domain and the activation domain). The sequences of the primers, G4-PCR-A and G4-PCR-B, are given as SEQ ID NO:22 and SEQ ID NO:23, respectively. Colonies yielding a PCR product were identified as containing intact GAL4, and were eliminated.

The GBT-A1 TRP[35] plasmid was eliminated by growing in Trp+ liquid media for 2–3 days, plating on -Leu media and then replica-plating on -Leu and -Trp plates to identify and eliminate colonies that had lost the GBT-A1 plasmid, yet still gave a positive signal.

Plasmid DNA was extracted from the remaining Leu+ candidates. The plasmid DNA was transformed into *E. coli* JBe181 and plated on -Leu media to select for library plasmids. The library plasmids isolated by this method were introduced back to the yeast reporter strains either alone or with test G4BD fusions: GBT, GBT-A1, and AS-lamin.

A parallel specificity assay was conducted by mating. Candidate strains, as described above, were 3-AT growth positive and X-gal positive when both the library and GBT-A1 plasmids were present. After elimination of the GBT-A1 plasmid from these strains, strains that were Leu+ Trp− 3-AT growth− and β-gal− were mated to the following strains: Y187 (MATα) carrying GBT, GBT-A1, or AS-lamin, and the diploids were assayed.

Among the 3-AT positive, β-gal positive candidates identified by the secondary screening method just described, one clone (III-21S, later termed GAD-CNIc) was specifically positive in conjunction with GBT-A1 in both the transformation assay and the mating assay.

B. Sequence of CNIc

Clone III-21S was sequenced as above. The sequence is presented herein as SEQ ID NO:1, and a schematic representation of the clone is shown in FIG. 1A. The Sau3AI library insert encodes 306 amino acids followed by a stop codon in frame with the coding sequence of GAL4, but does not contain an in-frame ATG start site upstream of the stop codon. This is consistent with the fragment encoding a c-terminal portion of a complete gene product. Accordingly, the clone was termed CNIc, with the lowercase "c" representing "c-terminal".

The stippled portion between GAL-4AD and CNIc in FIG. 1A represents the linker discussed in Materials and Methods, above. Also indicated in the Figure are the approximate locations of in-frame start (ATG) and stop codons, and Sau3AI restriction sites.

C. Isolation of a Full Length Clone

A $^{32}$P-labeled CNIc probe was generated from the 1.22 kb CNIc insert of clone III-21S by polymerase chain reaction (PCR) using primers represented as SEQ ID NO:7 and SEQ ID NO:8. The probe was used to map the gene to the right arm of chromosome 11 by hybridization screening (Sambrook, et al.) a panel of λ clones (American Type Culture Collection (ATCC), Rockville, Md.) spanning the entire yeast genome. Two clones, 70500 and 70590, gave positive hybridization signals. A phage lysate of clone 70500 in λ MG3 was obtained from the ATCC, was amplified, purified, restriction-mapped and used as a DNA source for subsequent cloning experiments.

The phage DNA was digested with SacI, yielding a 7.1 kb fragment containing the entire CNI gene. This fragment was cloned into "BLUESCRIPT SK" (Stratagene, La Jolla, Calif.) cut with SacI, yielding plasmid CNI7.1. Plasmid CNI7.1 was digested with MunI and EcoRV, releasing a 3.16 kb fragment containing the entire coding sequence of CNI. The 3.16 kb fragment was then cloned into each of YEp352 (HIS), YEp352(TRP), YEp352(URA), and "BLUESCRIPT SK", each cut with EcoRI and SmaI, yielding plasmids CNIH, CNIT, CNIU and CNI3.2, respectively. The sequence of the 3.16 kb MunI/EcoRV fragment is encompassed by the 3.5 kb sequence presented as SEQ ID NO:4. The MunI site is at nucleotide 100 of SEQ ID NO:4, and the EcoRV site is at nucleotide 3263 of SEQ ID NO:4.

A schematic diagram of the sequence presented as SEQ ID NO:4 is shown in FIG. 1B. This sequence contains the 3.16 kb MunI/EcoRV fragment used in many of the experiments described herein (depicted in FIG. 1B as the portion between the MunI and EcoRV sites), which contains the entire 2.75 kb coding sequence of CNI (SEQ ID NO:6; graphically indicated in FIG. 1B by the locations of the "ATG" and "Stop" codons).

FIG. 13 also shows the location of certain features of the sequence. For example, "PEST" motifs (Rogers, et al., Dice) are indicated by bars over the corresponding sequence.

A search of known DNA and protein sequences turned up no obvious matches or homologies to genes in other organisms. Accordingly, CNI may represent a new type of calcineurin-binding protein.

EXAMPLE 2

Binding of CNIc to Calcineurin

Y190 yeast carrying the plasmids indicated below were assayed for β-gal activity by color development assay described above to determine the specificity of binding of CNIc to subunits of calcineurin.

Exemplary data, in the form of images of filters having yeast colony replicas that had undergone the β-gal color development assay are shown in FIG. 2A. The legend for FIG. 2A is shown in FIG. 2B. Numbers in the legend refer to locations of yeast colonies expressing particular combinations of plasmid constructs. The constructs are as follows:

20:GBT-A1 and GAD-B1, 21:GBT-A1 and GAD-CNIc, 22:GBT-A1 and GAD-CNIc, 23:GBT-A1 and GAD-CNIc 24:GBT-A2 and GAD-CNIc 25:AS-lamin and GAD-CNIc 26:GBT and GAD-CNIc.

Yeast colonies used in the assay were derived by several different methods. Those at location 22 were purified colonies from the original library screen, those at 21 were colonies transformed with mini-prep DNA of the isolated GAD-CNIc plasmid, and the remaining colonies (23, 24, 25 and 26) were transformed with maxi-prep (Qiagen, Chatsworth, Calif.) DNA of GAD-CNIc.

A comparison of the intensities of the blue β-gal reaction product indicates that CNIc interacted strongly with CNA1 regardless of the source of the CNIc plasmid DNA (20, 21, 22 and 23), and somewhat less strongly with CNA2 (24). Neither cells containing AS-lamin with GAD-CNIc (25), nor cells containing only GBT with GAD-CNIc (26) showed a detectable signal above background. Two subunits of calcineurin (CNA1, CNB1) known to interact were used as a positive control for the assay (20).

In summary, the data above show that CNIc interacted specifically with CNA1 and CNA2, but not with G4BD or lamin C.

A similar set of experiments was conducted using constitutively-active CNA subunits, as well as calcineurin subunit CNB1. As described in Materials and Methods, above, CNA1ΔC and CNA2ΔC were each missing a C-terminal portion of the protein containing an autoinhibitory domain. Exemplary results from these experiments are shown in FIG. 3A. The legend for FIG. 3A is shown in FIG. 3B. Locations of yeast colonies expressing specific constructs are as follows: 27:GBT and GAD-CNIc, 28:GBT-A1ΔC and GAD-CNIc, 29:GBT-A2ΔC and GAD-CNIc, 30:GBT-A1ΔC and GAD, 31:GBT-A2ΔC and GAD, 32:GBT-B1 and GAD-CNIc, 33:GBT-B1 and GAD, 34:GBT-A1ΔC and GAD-B1, and 35:GBT-A2ΔC and GAD-B1.

The data show that GBT-A1ΔC and GAD-CNIc (28) gave a definite positive signal, while GBT-A2ΔC and GAD-CNIc (29) was weaker, though still detectable above its background (i.e. GBT-A2ΔC and GAD; 31). The signal from GBT-B1 and GAD-CNIc (32) was not detectable above vector background (GBT-B1 and GAD; 33). Positive controls GBT-A1ΔC and GAD-B1 (34) and GBT-A2ΔC and GAD-B1 (35) gave strong signals.

These data show that CNIc interacted specifically with CNA1ΔC and CNA2ΔC, but not with CNB1.

EXAMPLE 3

Effects of Immunosuppressant Drugs on Binding of CNIc to Calcineurin in B1$^{wt}$, B1 Deletion and B1Overproducing Yeast Strains Three yeast strains carrying the plasmids indicated below were assayed for β-gal activity as above to determine if the immunosuppressant drugs FK506, cyclosporin A (CsA) and rapamycin affect the binding of CNIc to subunits of calcineurin. The experiments were performed in yeast strains wild-type for the CNB1 subunit, null for the CNB1 subunit, and in yeast transformed with a high efficiency expression vector containing DNA encoding the CNB1 subunit.

Exemplary data, in the form of filter images produced as above are shown in FIGS. 4A, 4C, 5A and 5C. Plates used to make the filters shown in FIGS. 4A and 4C were replicas from one master plate, while plates used to make the filters shown in FIGS. 5A and 5C were replicas from another plate.

The plates used to generate filters shown in FIGS. 4A and 5A were without FK506, while the plates used to generate filters shown in FIGS. 4C and 5C contained 1 μg/ml FK506.

The legends for FIGS. 4A and 4C are shown in FIGS. 4B and 4D, respectively. Since the imaged filters in FIGS. 4A and 4C were from replica plates, corresponding locations on each filter contain material from the same yeast colonies. Accordingly, the locations are referred to by the same "base" numbers in the legends. To facilitate reference to a specific location on a specific filter, the base numbers are followed by a lowercase letter that is different for each of the individual filters. For example, in the present figure, "a" follows the base numbers to identify locations on the filter shown in FIG. 4A, while a "b" follows the base numbers to identify locations on the plate in FIG. 4C. This labeling scheme is used in other experiments detailed herein where multiple filter lifts are shown.

The interactions of various combinations of proteins expressed by constructs indicated below was studied in three yeast strains. Strain Y153b$^-$, at 36–40, is null for the CNB1 subunit of calcineurin. Strains Y190 (41–46) and Y526 (47–51) are wild-type for CNA1, CNA2 and CNB1. Hybrid proteins expressed by colonies at specific locations are as follows: 36:GBT-A1 and GAD-CNIc, 37:GBT-A2 and GAD-CNIc, 38:GBT-A1ΔC and GAD-CNIc, 39:GBT and GAD-CNIc, 40:GBT-A2ΔC and GAD-CNIc, 41:GBT-A1 and GAD-CNIc, 42:GBT and GAD-CNIc, 43:GBT-A2 and GAD-CNIc, 44:GBT-A1ΔC and GAD-CNIc, 45:GBT-A1 and GAD-B1, 46:GBT-A2ΔC and GAD-CNIc, 47:GBT-A1 and GAD-CNIc, 48:GBT and GAD-CNIc, 49:GBT-A2 and GAD-CNIc, 50:GBT-A1ΔC and GAD-CNIc, and 51:GBT-A2ΔC and GAD-CNIc.

Yeast strain Y526 was used for all experiments shown in FIGS. 5A, 5B, 5C and 5D. The expression vector B1/YEp352(HIS) was not used in strains Y190 or Y153b1 because they are HIS$^+$ in the absence of 3-AT.

Figure 5B:
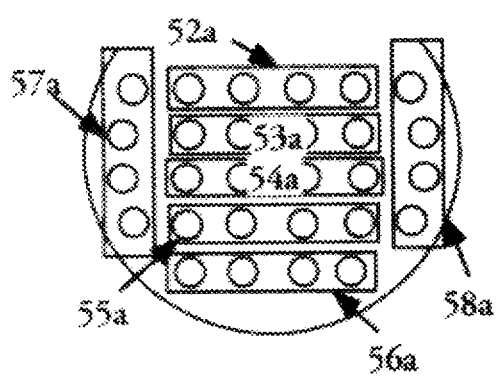
Figure 5D:
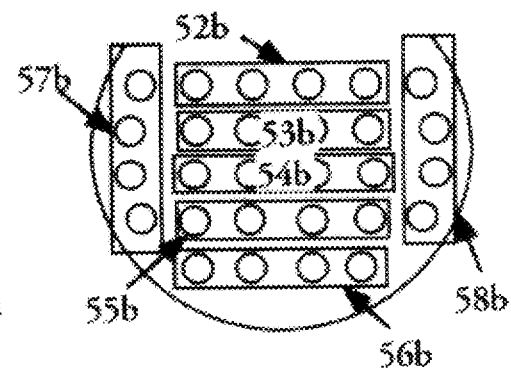

The base numbers in FIGS. 5B and 5D correspond to locations of colonies expressing the following constructs: 52:GBT-A1, GAD-CNIc and YEp352, 53:GBT-A1, GAD-CNIc and B1/YEp352, 54:GBT-A2, GAD-CNIc and YEp352, 55:GBT-A2, GAD-CNIc and B1/YEp352, 56:GBT, GAD-CNIc and B1/YEp352, 57:GBT-A1ΔC, GAD-CNIc and B1/YEp352, and 58:GBT-A2ΔC, GAD-CNIc and B1/YEp352.

A comparison of data shown in FIG. 4A (no added drugs) shows the effect of deleting the endogenous host CNB1 gene on interactions between CNIc and calcineurin subunits CNA1, CNA2, CNA1ΔC and CNA2ΔC. Note that interactions in panels 36a–40a (CNB1 null strain) were all stronger (with the exception of the negative control in 39) than interactions in corresponding panels 41a–51a (strains wild-type for CNB1). This result indicates that interaction between CNIc and CNA subunits were enhanced by the deletion of the CNB1 subunit.

Comparison of corresponding panels in FIGS. 4A and 4C shows the effects of FK506 on CNIc-CNA/CNAΔC interactions. The drug enhanced interactions under all except control (39, 42 and 48) conditions. The effect was most striking in yeast strains wild-type for the CNB1 subunit (e.g., compare 50a with 50b, and 51a with 51b).

The drug also markedly enhanced CNIc-CNA/CNAΔC interactions under conditions where the CNB1 subunit was overexpressed. FIG. 5A shows the effect of overexpressing CNB1 on CNIc-CNA/CNAΔC interactions in the absence of drug. Colonies expressing B1/YEp352 (53a, 55a–58a) had reduced signal as compared with controls expressing only YEp352 (52a, 54a). Inclusion of FK506 in the plating medium (FIG. 5C), however, enhanced interactions in all colonies, except the negative controls (56).

Taken together, the above data demonstrate that the interaction of CNIc with CNA and CNAΔC was markedly enhanced by FK506. The interaction was also enhanced by deletion of CNB1 and diminished by overexpression of CNB1, and the inhibitory effect of CNB1 overproduction was overcome by the stimulatory effect of FK506.

In light of the effects of FK506 on CNIc-CNA/CNAΔC interactions, two other immunosuppressants, cyclosporin A and rapamycin, were examined in similar experiments. The results of these experiments are shown in FIGS. 6A–6F and 7A–7H. Filters shown in FIGS. 6A–6F were from replica plates, as were those in FIGS. 7A–7H. Colonies shown in FIGS. 6A and 7A were plated without drugs; those in FIGS. 6C and 7C were plated with FK506 (1 μg/ml), those in FIGS. 6E and 7E with CsA (10 μg/ml), and those in FIG. 7G with rapamycin (10 ng/ml). Yeast strains used were as follows: In FIGS. 6A–6F, panels 59–63 were Y153b1⁻, 64–69 were Y190, and 70–74 were Y526. In Figs. 7A–7H, panels 77–83 were Y526, and panels 75 and 76 were Y190.

Figure 6B:
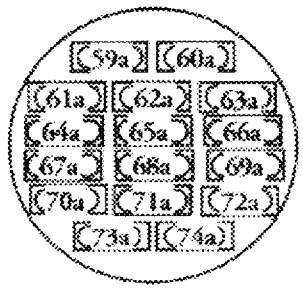
Figure 6D:
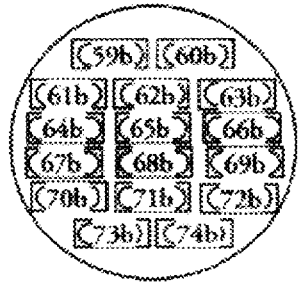
Figure 6F:
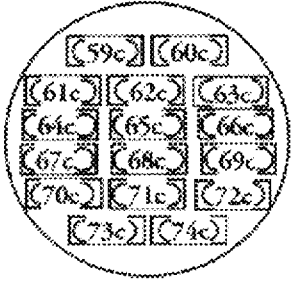

The base numbers in FIGS. 6B, 6D and 6F correspond to locations of colonies expressing the following constructs: 59:GBT-A1 and GAD-CNIc, 60:GBT-A2 and GAD-CNIc, 61:GBT-A1ΔC and GAD-CNIc, 62:GBT and GAD-CNIc, 63:GBT-A2ΔC and GAD-CNIc, 64:GBT-A1 and GAD-CNIc, 65:GBT and GAD-CNIc, 66:GBT-A2 and GAD-CNIc, 67:GBT-A1ΔC and GAD-CNIc, 68:GBT-A1 and GAD-B1, 69:GBT-A2ΔC and GAD-CNIc, 70:GBT-A1 and GAD-CNIc, 71:GBT and GAD-CNIc, 72:GBT-A2 and GAD-CNIc, 73:GBT-A1ΔC and GAD-CNIc, and 74:GBT-A2ΔC and GAD-CNIc.

The base numbers in FIGS. 7B, 7D, 7F and 7H correspond to locations of colonies expressing the following constructs: 75:GBT-FKBP and GAD, 76:GBT-FKBP and GAD-CNIc, 77:GBT-A1, GAD-CNIc and YEp352, 78:GBT-A1, GAD-CNIc and B1/YEp352, 79:GBT-A2, GAD-CNIc and YEp352, 80:GBT-A2, GAD-CNIc and B1/YEp352, 81:GBT, GAD-CNIc and B1/YEp352, 82:GBT-A1ΔC, GAD-CNIc and B1/YEp352, and 83:GBT-A2ΔC, GAD-CNIc and B1/YEp352.

The data presented in FIGS. 6A and 6C are essentially equivalent to those presented in FIGS. 4A and 4C, respectively. The constructs and yeast strains at corresponding locations were the same. As expected, the β-gal signal was also essentially equivalent between the two sets. Data shown in FIG. 6E demonstrate that like FK506, the immunosuppressant cyclosporin A was also effective in enhancing interaction of CNIc with CNA and CNAΔC. Both FK506 and cyclosporin A are known to exert their immunosuppressive effects through inhibition of calcineurin activity (Cyert).

Similarly, data shown in FIGS. 7A and 7C are essentially equivalent to those in FIGS. 5A and 5C, except that a top panel has been added in FIGS. 7A–H. As above, the corresponding panels show the same constructs and yeast strains. The added panels (75 and 76) assessed the interaction of an FK506 binding protein (FKBP) with CNIc, and indicate that there were no detectable interactions between these proteins. Results in FIG. 7E demonstrate that cyclosporin A had a similar effect to FK506 in cells overexpressing CNB1—that is, it enhanced the interactions between CNIc and CNA/CNAΔC.

In contrast, data presented in FIG. 7G show that the immunosuppressant rapamycin, which is known not to target calcineurin, had no detectable effect on CNIc-CNA/CNAΔC interactions (compare FIG. 7G with FIG. 7A).

Taken together, the above data show that like FK506, cyclosporin A (CsA), but not rapamycin, also enhanced the interaction of CNIc with CNA and CNAΔC. CNIc didn't interact with FKBP with or without FK506.

EXAMPLE 4

Effects of CNI on FKBP/FK506 binding to Calcineurin

Y526 cells, carrying the plasmids indicated below, were grown in -Trp-Leu-His liquid media with or without FK506 (1 μg/ml) until $OD_{600}$ reached about 1.0. Approximately the same number of cells, calculated based on $OD_{600}$ and equivalent to 1 ml of an $OD_{600}=1$ suspension, was harvested from each culture, washed once with $ddH_2O$, centrifuged briefly, and the pellet was resuspended in 30 μl $ddH_2O$ and transferred onto a nitrocellulose filter. The filters were frozen in liquid nitrogen as described above, placed in a 8.5 cm petri dish containing a sheet of Whatman No. 1 paper (Whatman International LTD, Maidstone, UK) in 1.6 ml Z buffer containing 0.1% X-Gal, and incubated at 30° C. for 8 hours.

FIG. 8A presents exemplary data from studies to assess the effect of CNI overexpression on FK506-mediated FKBP interactions with CNA2. The legend for FIG. 8A is shown in FIG. 8B. Locations of yeast colonies expressing specific constructs: 84:GBT-FKBP, GAD-A2 and YEp352, 85:GBT-FKBP, GAD-A2 and YEp352, 86:GBT-FKBP, GAD-A2 and CNI/YEp352, and 87:GBT-FKBP, GAD-A2 and CNI/YEp352. The cells at 85 and 87 were exposed to FK506, while those at 84 and 86 were not.

Data in FIG. 8A demonstrate that, in the absence of FK506, FKBP and CNA2 showed no detectable interaction (84). In the presence of FK506, however, the proteins interacted (85), presumably because FK506 formed a complex with FKBP, which then bound CNA2 (Cyert).

Data in FIG. 8A further show that, in the absence of FK506, CNI had no effect on the lack of interaction between FKBP and CNA2 (86). In the presence of FK506 (87), however, CNI potentiated, or enhanced the binding between FKBP and CNA2 (compare the intensity at 87 with that at 85). This effect suggests that CNI and similar compounds may be employed to increase the sensitivity of calcineurin to immunosuppressant drugs that act on it, and in this way, decrease the amount of the immunosuppressant required for a particular level of immunosuppression.

Experiments illustrated in FIGS. 9A and 9B demonstrate that CNI overproduction had little or no effect on the binding of CNA2 to CNB1, providing support for the specificity of the stimulatory effect that CNI overproduction had on the FK506-dependent binding of FKBP to calcineurin. The legends for FIG. 9A and 9B are shown in FIGS. 9B and 9D, respectively. Locations of yeast colonies expressing the following constructs: 88:GBT-A2, GAD-B1 and YEp352, 89:GBT-A2, GAD-B1 and YEp352, 90:GBT-A2, GAD-B1 and CNI/YEp352, and 91:GBT-A2, GAD-B1 and CNI/YEp352. The colonies at 89 and 91 were exposed to FK506, while colonies at 88 and 90 were not.

Taken together, the above data show that overexpression of the full-length CNI clone markedly enhanced the FK506-dependent interaction of FKBP with CNA, although it didn't affect the interaction between CNA and CNB1.

EXAMPLE 5

Co-Immunoprecipitation of CNIc and CNA

Yeast BJ2407 harboring AS-CNIc, which carries an influenza hemagglutinin (HA) epitope tag (Wilson, et al.), and GAD-A2 (lanes 1, 3) or A2/YEp352 (lanes 2, 5), and strain MCY300-1 (cna1⁻cna2⁻; lane 4) were grown in selective media to $OD_{600}$=0.8. The cells were harvested, lysed, and immunoprecipitated in the presence of 25 μg/ml FK506 with anti-HA monoclonal antibody (obtained from M. Kirschner, Harvard University, Boston, Mass.; Wilson, et al.), following protocols described in Harlow, et al. The cell extracts (lanes 3-5) and the immune complex (lanes 1, 2) were resolved by sodium dodecyl sulfate polyacrylamide gel electrophoresis (SDS-PAGE; Laemmli) followed by western blot with a rabbit anti-CNA2 polyclonal antibody generated using standard methods (Harlow, et al.). Bound anti-CNA2 antibody was visualized with the "ECL" kit (Amersham, Arlington Heights, Ill.) using goat anti-rabbit antibody. Molecular weight markers are indicated on the right in kD.

The results demonstrate that CNIc was capable of binding to CNA2 tightly enough for the complex to be co-immunoprecipitated. This independent, biochemical assay confirmed the results described above obtained using the two hybrid protein interaction assay—that is, that CNIc physically interacted with and bound CNA subunits.

Cell extracts of BJ2407 harboring AS-CNIc, and GAD-A2 or A1/Yep351, and Y153b1 harboring AS-CNIc and GAD-A1 were subjected to SDS-PAGE followed by western blot with anti HA antibody. The results showed that CNIc was present at very low levels in vivo.

The results are consistent with the observations that a limited amount of CNA2 was precipitated by anti-HA antibody recognizing the CNIc fusions, and that CNI contains PEST-like motifs, a feature of proteins with a short half-life in vivo (Rogers, et al.).

EXAMPLE 6

Northern Blot of CNIc

Norther blots (e.g., Sambrook, et al.) of yeast total RNA were hybridized with a CNIc probe. Exemplary data are shown in FIG. 11. 20 μg yeast RNA from YPH499 (lane 1) and MCY300-1 (lane 2) was resolved in a formaldehyde-agarose gel, transferred onto "HYBOND N⁺" membrane (Amersham, Arlington Heights, Ill.), and hybridized with $5\times10^6$ cpm/ml probe of the CNIc insert (1.22 kb). A single message of approximately 2.9 kb was detected in both strains at about the same level following an 18-hour exposure on XAR5 film (Eastman Kodak, Rochester, N.Y.).

The data indicate that CNI was a physiologically expressed gene encoding a 2.9 kb message in yeast.

EXAMPLE 7

Chromosome Mapping of CNIc

A yeast chromosome blot obtained from the ATCC was hybridized with probe of the CNIc insert following the Southern hybridization procedure described in Sambrook, et al. A positive hybridization signal was obtained with two ATCC yeast genomic λ clones derived from chromosome 11. Clone 70500 had a relatively strong signal, while clone 70590 had a somewhat weaker one. A phage lysates of clone 70500 was ordered from the ATCC, amplified, purified, restriction-mapped, and used as a DNA source for cloning full length CNI (Example 1).

EXAMPLE 8

CNI null Mutants

1. Construction of cni Null Mutation

A 5', 1.8 kb BglII-HindIII and a 3', 0.9 kb XbaI-BglII fragment of CNI were ligated into pRS305(LEU2) (Sikorski, et al.). The resultant plasmid had a deletion of a 2 kb HindIII- XbaI fragment from the coding sequence of CNI. This cni::LEU2 mutant was introduced into the genomes of yeast haploid strains YPH499 (Sikorski, et al.), MCY300-1 (cna1⁻ cna2⁻) and DD12 (cnb1⁻) (Cyert, et al., 1991, Cyert, et al., 1992) as well as two diploid strains.

Leucine prototrophs were isolated at high frequency from all strains, and hybridization analysis confirmed that the cni::LEU2 allele had replaced the CNI gene. The experiments indicate that CNI is not essential for viability, since CNI deletion mutant strains (even cni⁻ cn⁻ double mutants) can survive.

CNI was deleted from three yeast strains: YPH499 (WT), MCY300-1 (cna1⁻cna2⁻), and DD12 (cnb1⁻), resulting in cni⁻ strains LHy499, LHy300 and LHy12, respectively. Cells representing four colonies of each cni knockout strain and two colonies of each parent strain were grown in liquid YPD (Sherman, et al.) to saturation. Same numbers of cells from each culture were then plated onto YPD+Hygromycin B (40 μg/ml) and growth was monitored at 30° C.

CNI deletions in each strain rendered that strain more resistant to hygromycin B. The effect was particularly pronounced in both MCY300-1 and DD12, suggesting that CNI functions as a suppressor of CN mutant's sensitivity to hygromycin B. The data indicate that deletion of CNI results in higher resistance to hygromycin B.

EXAMPLE 9

Isolation of CNI/β-Galactosidase Fusion Protein

A CNI coding sequence is cloned into the λ gt11 vector (Stratagene, La Jolla, Calif.). The coding frame is cloned in-frame to the β-galactosidase coding sequences present in λ gt11. Bacterial lysogens infected either with lambda phage gt11 or with gt11/CNI are incubated in 32° C. until the culture reaches to an O.D. of 0.4. Then the culture is incubated in a 43° C. water bath for 15 minutes to induce gt11 peptide synthesis, and further incubated at 37° C. for 1 hour. Bacterial cells are pelleted and lysed in lysis buffer (10 mM Tris, pH 7.4, 2% "TRITON X-100" and 1% aprotinin). Bacterial lysates are clarified by centrifugation (10K, for 10 minutes, Sorvall JA20 rotor) and the clarified lysates are incubated with Sepharose 4B beads conjugated with anti-β-galactosidase (Promega).

Binding and elution of β-galactosidase fusion proteins are performed according to the manufacturer's instruction. Typically binding of the proteins and washing of the column are done with lysis buffer. Bound proteins are eluted with 0.1M carbonate/bicarbonate buffer, pH 10.

While the invention has been described with reference to specific methods and embodiments, it will be appreciated that various modifications and changes may be made without departing from the invention.

It is claimed:

1. A composition containing a polypeptide that is between 15 and 306 amino acids in length that is identical to a corresponding region in the sequence represented by SEQ ID NO:2.

2. The composition of claim 1, wherein the composition contains a polypeptide having the amino acid sequence represented by SEQ ID NO:2.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
    ( A ) LENGTH: 1222 base pairs
    ( B ) TYPE: nucleic acid
    ( C ) STRANDEDNESS: double
    ( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
    ( C ) INDIVIDUAL ISOLATE: Sau3AI fragment containing CNIc
      coding sequence ( i x ) FEATURE:
    ( A ) NAME/KEY: CDS
    ( B ) LOCATION: 1..918

( x i ) SEQUENCE DESCRIPTION: SEQ ID NO:1:

| GAT | CAA | AGT | AGC | AAT | GTC | TTC | GCA | TCC | AAA | CAG | CTG | GTC | GCA | AAC | ATT | 48 |
| Asp | Gln | Ser | Ser | Asn | Val | Phe | Ala | Ser | Lys | Gln | Leu | Val | Ala | Asn | Ile | |
| 1 | | | | 5 | | | | | 10 | | | | | 15 | | |

| TAT | AAG | CCC | AAT | CAG | ATT | CCA | AGA | GAA | TTA | ACT | TCT | CCT | CAG | GCG | TTA | 96 |
| Tyr | Lys | Pro | Asn | Gln | Ile | Pro | Arg | Glu | Leu | Thr | Ser | Pro | Gln | Ala | Leu | |
| | | | 20 | | | | | 25 | | | | | 30 | | | |

| CCA | TTA | TCG | CCC | ATC | ACC | TCA | CCA | ATT | CTC | AAT | TAC | CAA | CCA | TTA | TCA | 144 |
| Pro | Leu | Ser | Pro | Ile | Thr | Ser | Pro | Ile | Leu | Asn | Tyr | Gln | Pro | Leu | Ser | |
| | | 35 | | | | | 40 | | | | | 45 | | | | |

| AAC | TCC | CCG | CCT | CCA | GAT | TTT | GAT | TTT | GAT | CTA | GCT | AAG | CGC | GGC | GCA | 192 |
| Asn | Ser | Pro | Pro | Pro | Asp | Phe | Asp | Phe | Asp | Leu | Ala | Lys | Arg | Gly | Ala | |
| | 50 | | | | | 55 | | | | | 60 | | | | | |

| GCC | GAT | TCT | CAT | GCT | ATT | CCT | GTG | GAT | CCT | CCA | TCA | TAT | TTT | GAT | GTA | 240 |
| Ala | Asp | Ser | His | Ala | Ile | Pro | Val | Asp | Pro | Pro | Ser | Tyr | Phe | Asp | Val | |
| 65 | | | | | 70 | | | | | 75 | | | | | 80 | |

| TTA | AAG | GCC | GAT | GGG | ATT | GAA | TTG | CCA | TAC | TAC | GAT | ACA | AGT | TCA | TCT | 288 |
| Leu | Lys | Ala | Asp | Gly | Ile | Glu | Leu | Pro | Tyr | Tyr | Asp | Thr | Ser | Ser | Ser | |
| | | | | 85 | | | | | 90 | | | | | 95 | | |

| AAA | ATT | CCT | GAA | CTA | AAA | CTA | AAC | AAA | TCT | AGA | GAG | ACA | TTG | GCC | AGC | 336 |
| Lys | Ile | Pro | Glu | Leu | Lys | Leu | Asn | Lys | Ser | Arg | Glu | Thr | Leu | Ala | Ser | |
| | | | 100 | | | | | 105 | | | | | 110 | | | |

| ATT | GAG | GAG | GAC | TCA | TTC | AAT | GGT | TGG | TCT | CAA | ATT | GAT | GAC | TTA | TCC | 384 |
| Ile | Glu | Glu | Asp | Ser | Phe | Asn | Gly | Trp | Ser | Gln | Ile | Asp | Asp | Leu | Ser | |
| | | 115 | | | | | 120 | | | | | 125 | | | | |

| GAC | GAA | GAT | GAC | AAT | GAT | GGC | GAT | ATA | GCA | TCT | GGT | TTC | AAC | TTC | AAG | 432 |
| Asp | Glu | Asp | Asp | Asn | Asp | Gly | Asp | Ile | Ala | Ser | Gly | Phe | Asn | Phe | Lys | |
| | 130 | | | | | 135 | | | | | 140 | | | | | |

| CTG | TCA | ACC | AGT | GCT | CCG | AGT | GAG | AAC | GTT | AAT | TCA | CAC | ACT | CCT | ATT | 480 |
| Leu | Ser | Thr | Ser | Ala | Pro | Ser | Glu | Asn | Val | Asn | Ser | His | Thr | Pro | Ile | |
| 145 | | | | | 150 | | | | | 155 | | | | | 160 | |

| TTG | CAG | TCT | TTA | AAC | ATG | AGT | CTT | GAT | GGG | AGA | AAA | AAA | AAT | CGT | GCC | 528 |
| Leu | Gln | Ser | Leu | Asn | Met | Ser | Leu | Asp | Gly | Arg | Lys | Lys | Asn | Arg | Ala | |
| | | | | 165 | | | | | 170 | | | | | 175 | | |

| AGT | CTA | CAC | GCA | ACA | TCA | GTG | TTA | CCT | AGT | ACA | ATA | AGA | CAG | AAC | AAT | 576 |
| Ser | Leu | His | Ala | Thr | Ser | Val | Leu | Pro | Ser | Thr | Ile | Arg | Gln | Asn | Asn | |
| | | | 180 | | | | | 185 | | | | | 190 | | | |

| | | | | | | | | | | | | | | | | |
|---|---|---|---|---|---|---|---|---|---|---|---|---|---|---|---|---|
| CAG | CAT | TTC | AAT | GAC | ATA | AAC | CAG | ATG | CTA | GGC | AGT | AGT | GAC | GAA | GAT | 624 |
| Gln | His | Phe | Asn | Asp | Ile | Asn | Gln | Met | Leu | Gly | Ser | Ser | Asp | Glu | Asp | |
| | | 195 | | | | | 200 | | | | | 205 | | | | |
| GCC | TTT | CCC | AAA | AGC | CAA | TCA | TTA | AAT | TTC | AAT | AAG | AAA | CTA | CCA | ATA | 672 |
| Ala | Phe | Pro | Lys | Ser | Gln | Ser | Leu | Asn | Phe | Asn | Lys | Lys | Leu | Pro | Ile | |
| | | 210 | | | | 215 | | | | | 220 | | | | | |
| CTT | AAA | ATT | AAT | GAT | AAC | GTC | ATA | CAA | TCA | AAC | AGC | AAT | AGT | AAT | AAC | 720 |
| Leu | Lys | Ile | Asn | Asp | Asn | Val | Ile | Gln | Ser | Asn | Ser | Asn | Ser | Asn | Asn | |
| 225 | | | | | 230 | | | | | 235 | | | | | 240 | |
| AGA | GTT | GAT | AAT | CCA | GAA | GAT | ACA | GTG | GAT | TCT | TCA | GTC | GAT | ATT | ACA | 768 |
| Arg | Val | Asp | Asn | Pro | Glu | Asp | Thr | Val | Asp | Ser | Ser | Val | Asp | Ile | Thr | |
| | | | | 245 | | | | | 250 | | | | | 255 | | |
| GCA | TTT | TAT | GAT | CCA | AGA | ATG | TCA | TCA | GAT | TCC | AAA | TTT | GAT | TGG | GAG | 816 |
| Ala | Phe | Tyr | Asp | Pro | Arg | Met | Ser | Ser | Asp | Ser | Lys | Phe | Asp | Trp | Glu | |
| | | | 260 | | | | | 265 | | | | | 270 | | | |
| GTA | AGC | AAG | AAC | CAT | GTT | GAC | CCA | GCA | GCC | TAC | TCG | GTT | AAC | GTT | GCT | 864 |
| Val | Ser | Lys | Asn | His | Val | Asp | Pro | Ala | Ala | Tyr | Ser | Val | Asn | Val | Ala | |
| | | 275 | | | | | 280 | | | | | 285 | | | | |
| AGT | GAA | AAC | CGT | GTA | CTG | GAC | GAC | TTT | AAG | AAA | GCA | TTT | CGC | GAA | AAG | 912 |
| Ser | Glu | Asn | Arg | Val | Leu | Asp | Asp | Phe | Lys | Lys | Ala | Phe | Arg | Glu | Lys | |
| | 290 | | | | | 295 | | | | | 300 | | | | | |
| AGA | AAA | TAAGTACATT | ATTTTCATTC | TCCGACAGAA | TTGCTACCAT | TTTACTTTGT | | | | | | | | | | 968 |
| Arg | Lys | | | | | | | | | | | | | | | |
| 305 | | | | | | | | | | | | | | | | |

```
GTCCTGTGAT TCAATAGTGT ACAATATATT GGACATTTTA TAGTATACAA ATATACACCA      1028

TCAATCTATA CATCCATATC ACTTGTCGTA AAGATATCCC TTTTAATAG TACAGCGATT       1088

AAAAAAATAA CATGATTAAC GTTCAGTTAC CAATGAGCTT ATTATTAGG CTTGCTTTAG       1148

ATTTTTCCAA GTCAATTTTT GTTTTTTCTA ACGCTTGCAA CCTCATCTCA ACCTTCTTCC     1208

TTTGCAAGCA GATC                                                        1222
```

( 2 ) INFORMATION FOR SEQ ID NO:2:

( i ) SEQUENCE CHARACTERISTICS:
        ( A ) LENGTH: 306 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Asp  Gln  Ser  Ser  Asn  Val  Phe  Ala  Ser  Lys  Gln  Leu  Val  Ala  Asn  Ile
 1                 5                       10                      15

Tyr  Lys  Pro  Asn  Gln  Ile  Pro  Arg  Glu  Leu  Thr  Ser  Pro  Gln  Ala  Leu
               20                      25                      30

Pro  Leu  Ser  Pro  Ile  Thr  Ser  Pro  Ile  Leu  Asn  Tyr  Gln  Pro  Leu  Ser
          35                      40                      45

Asn  Ser  Pro  Pro  Pro  Asp  Phe  Asp  Phe  Asp  Leu  Ala  Lys  Arg  Gly  Ala
     50                      55                      60

Ala  Asp  Ser  His  Ala  Ile  Pro  Val  Asp  Pro  Pro  Ser  Tyr  Phe  Asp  Val
 65                      70                      75                      80

Leu  Lys  Ala  Asp  Gly  Ile  Glu  Leu  Pro  Tyr  Tyr  Asp  Thr  Ser  Ser  Ser
                    85                      90                      95

Lys  Ile  Pro  Glu  Leu  Lys  Leu  Asn  Lys  Ser  Arg  Glu  Thr  Leu  Ala  Ser
               100                     105                     110

Ile  Glu  Glu  Asp  Ser  Phe  Asn  Gly  Trp  Ser  Gln  Ile  Asp  Asp  Leu  Ser
          115                     120                     125

Asp  Glu  Asp  Asp  Asn  Asp  Gly  Asp  Ile  Ala  Ser  Gly  Phe  Asn  Phe  Lys
     130                     135                     140
```

| Leu | Ser | Thr | Ser | Ala | Pro | Ser | Glu | Asn | Val | Asn | Ser | His | Thr | Pro | Ile |
| 145 | | | | | 150 | | | | 155 | | | | | | 160 |

| Leu | Gln | Ser | Leu | Asn | Met | Ser | Leu | Asp | Gly | Arg | Lys | Lys | Asn | Arg | Ala |
| | | | | 165 | | | | | 170 | | | | | 175 | |

| Ser | Leu | His | Ala | Thr | Ser | Val | Leu | Pro | Ser | Thr | Ile | Arg | Gln | Asn | Asn |
| | | | 180 | | | | | 185 | | | | | 190 | | |

| Gln | His | Phe | Asn | Asp | Ile | Asn | Gln | Met | Leu | Gly | Ser | Ser | Asp | Glu | Asp |
| | | 195 | | | | | 200 | | | | | 205 | | | |

| Ala | Phe | Pro | Lys | Ser | Gln | Ser | Leu | Asn | Phe | Asn | Lys | Lys | Leu | Pro | Ile |
| | 210 | | | | | 215 | | | | | 220 | | | | |

| Leu | Lys | Ile | Asn | Asp | Asn | Val | Ile | Gln | Ser | Asn | Ser | Asn | Ser | Asn | Asn |
| 225 | | | | | 230 | | | | 235 | | | | | | 240 |

| Arg | Val | Asp | Asn | Pro | Glu | Asp | Thr | Val | Asp | Ser | Ser | Val | Asp | Ile | Thr |
| | | | | 245 | | | | | 250 | | | | | 255 | |

| Ala | Phe | Tyr | Asp | Pro | Arg | Met | Ser | Ser | Asp | Ser | Lys | Phe | Asp | Trp | Glu |
| | | | 260 | | | | | 265 | | | | | 270 | | |

| Val | Ser | Lys | Asn | His | Val | Asp | Pro | Ala | Ala | Tyr | Ser | Val | Asn | Val | Ala |
| | | 275 | | | | | 280 | | | | | 285 | | | |

| Ser | Glu | Asn | Arg | Val | Leu | Asp | Asp | Phe | Lys | Lys | Ala | Phe | Arg | Glu | Lys |
| | 290 | | | | | 295 | | | | | 300 | | | | |

| Arg | Lys |
| 305 | |

( 2 ) INFORMATION FOR SEQ ID NO:3:

( i ) SEQUENCE CHARACTERISTICS:
        ( A ) LENGTH: 918 base pairs
        ( B ) TYPE: nucleic acid
        ( C ) STRANDEDNESS: double
        ( D ) TOPOLOGY: unknown ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: CINc coding sequence ( x i ) SEQUENCE DESCRIPTION: SEQ ID NO:3:

| GATCAAAGTA | GCAATGTCTT | CGCATCCAAA | CAGCTGGTCG | CAAACATTTA | TAAGCCCAAT | 60 |
| CAGATTCCAA | GAGAATTAAC | TTCTCCTCAG | GCGTTACCAT | TATCGCCCAT | CACCTCACCA | 120 |
| ATTCTCAATT | ACCAACCATT | ATCAAACTCC | CCGCCTCCAG | ATTTTGATTT | TGATCTAGCT | 180 |
| AAGCGCGGCG | CAGCCGATTC | TCATGCTATT | CCTGTGGATC | CTCCATCATA | TTTTGATGTA | 240 |
| TTAAAGGCCG | ATGGGATTGA | ATTGCCATAC | TACGATACAA | GTTCATCTAA | AATTCCTGAA | 300 |
| CTAAAACTAA | ACAAATCTAG | AGAGACATTG | GCCAGCATTG | AGGAGGACTC | ATTCAATGGT | 360 |
| TGGTCTCAAA | TTGATGACTT | ATCCGACGAA | GATGACAATG | ATGGCGATAT | AGCATCTGGT | 420 |
| TTCAACTTCA | AGCTGTCAAC | CAGTGCTCCG | AGTGAGAACG | TTAATTCACA | CACTCCTATT | 480 |
| TTGCAGTCTT | TAAACATGAG | TCTTGATGGG | AGAAAAAAAA | ATCGTGCCAG | TCTACACGCA | 540 |
| ACATCAGTGT | TACCTAGTAC | AATAAGACAG | AACAATCAGC | ATTTCAATGA | CATAAACCAG | 600 |
| ATGCTAGGCA | GTAGTGACGA | AGATGCCTTT | CCCAAAAGCC | AATCATTAAA | TTTCAATAAG | 660 |
| AAACTACCAA | TACTTAAAAT | TAATGATAAC | GTCATACAAT | CAAACAGCAA | TAGTAATAAC | 720 |
| AGAGTTGATA | ATCCAGAAGA | TACAGTGGAT | TCTTCAGTCG | ATATTACAGC | ATTTTATGAT | 780 |

```
CCAAGAATGT CATCAGATTC CAAATTTGAT TGGGAGGTAA GCAAGAACCA TGTTGACCCA      840

GCAGCCTACT CGGTTAACGT TGCTAGTGAA AACCGTGTAC TGGACGACTT TAAGAAAGCA      900

TTTCGCGAAA AGAGAAAA                                                    918
```

( 2 ) INFORMATION FOR SEQ ID NO:4:

( i ) SEQUENCE CHARACTERISTICS:
        ( A ) LENGTH: 3500 base pairs
        ( B ) TYPE: nucleic acid
        ( C ) STRANDEDNESS: double
        ( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: genomic DNA fragment containing full
              CNI coding sequence ( i x ) FEATURE:
        ( A ) NAME/KEY: CDS
        ( B ) LOCATION: 376..3120

( x i ) SEQUENCE DESCRIPTION: SEQ ID NO:4:

```
CCGAACACTT CCTTCGAGAG AGTGCATTTT ACTATGTGAA CCAATTTTTC CTCTTTTTCG       60

GTTTGCAAGT TCACCTGAAA AACTGCTTAA CACTACTAGC AATTGCCCTA TTGTCGTACG      120

AGGACTTTGC CAAATGTATT CCCGGCTGTT TGTAGTATAT ATACGCAGAT ATATAATAGC      180

GCCGTCTTTT TACCTCTTTG AGCGAATTGC CAAATATTGA CTCTTTTGTC TTATTTCGCT      240

ATCCCCATCT TATCAAAAAT GGGAACAACT CGTTGAAATA AGAGACAAGC AACAAGAAAG      300

ACAACCAACA GAAAGTTCCA TTCCGCACAA ATACGCTGGA ATCCCATAGA ATATTGCTTG      360

TTCCTCTATG ACTAC ATG CTC CAA TTC AAT ACA GAA AAT GAT ACT GTA GCT      411
              Met Leu Gln Phe Asn Thr Glu Asn Asp Thr Val Ala
                1               5                  10

CCA GTG TTT CCC ATG GAG CAA GAT ATA AAT GCA GCA CCT GAT GCC GTC      459
Pro Val Phe Pro Met Glu Gln Asp Ile Asn Ala Ala Pro Asp Ala Val
         15                  20                  25

CCA CTG GTG CAG ACA ACA ACA CTA CAA GTC TTT GTA AAG CTT GCC GAA      507
Pro Leu Val Gln Thr Thr Thr Leu Gln Val Phe Val Lys Leu Ala Glu
 30                  35                  40

CCC ATA GTG TTT TTA AAA GGA TTT GAA ACT AAC GGA CTG TCT GAA ATA      555
Pro Ile Val Phe Leu Lys Gly Phe Glu Thr Asn Gly Leu Ser Glu Ile
 45                  50                  55                  60

GCC CCC AGT ATC TTA CGA GGA TCT CTT ATC GTC AGG GTG TTG AAA CCG      603
Ala Pro Ser Ile Leu Arg Gly Ser Leu Ile Val Arg Val Leu Lys Pro
             65                  70                  75

AAT AAA TTA AAA AGT ATA TCG ATA ACC TTC AAA GGA ATA TCC AGA ACA      651
Asn Lys Leu Lys Ser Ile Ser Ile Thr Phe Lys Gly Ile Ser Arg Thr
                 80                  85                  90

GAG TGG CCG GAA GGT ATA CCA CCG AAG AGA GAA GAA TTT TCA GAT GTT      699
Glu Trp Pro Glu Gly Ile Pro Pro Lys Arg Glu Glu Phe Ser Asp Val
         95                 100                 105

GAA ACT GTT GTC AAT CAC ACA TGG CCA TTT TAT CAG GCG GAT GAC GGC      747
Glu Thr Val Val Asn His Thr Trp Pro Phe Tyr Gln Ala Asp Asp Gly
110                 115                 120

ATG AAT TCT TTC ACC TTA GAA CAT CAC AGC TCA AAT AAT TCG TCC AAT      795
Met Asn Ser Phe Thr Leu Glu His His Ser Ser Asn Asn Ser Ser Asn
125                 130                 135                 140

CGC CCA TCT ATG AGC GAT GAA GAT TAT CTA CTT GAA AAA AGC GGT GCT      843
```

```
Arg Pro Ser Met Ser Asp Glu Asp Tyr Leu Leu Glu Lys Ser Gly Ala
            145             150                 155

TCA GTA TAT ATC CCA CCA ACC GCT GAA CCC CCT AAA GAT AAT AGC AAT      891
Ser Val Tyr Ile Pro Pro Thr Ala Glu Pro Pro Lys Asp Asn Ser Asn
            160             165                 170

CTA AGT CTG GAT GCC TAT GAG CGC AAC TCA TTG TCA TCC GAT AAT TTG      939
Leu Ser Leu Asp Ala Tyr Glu Arg Asn Ser Leu Ser Ser Asp Asn Leu
        175             180                 185

AGT AAC AAG CCA GTA TCA AGT GAT GTT TCC CAT GAC GAC AGT AAA CTG      987
Ser Asn Lys Pro Val Ser Ser Asp Val Ser His Asp Asp Ser Lys Leu
        190             195                 200

TTG GCT ATT CAA AAG ACA CCA TTA CCA TCA TCT AGT CGA AGA GGA TCG     1035
Leu Ala Ile Gln Lys Thr Pro Leu Pro Ser Ser Ser Arg Arg Gly Ser
205             210             215                 220

GTA CCG GCA AAT TTT CAC GGT AAC TCT TTG TCA CCT CAT ACC TTC ATA     1083
Val Pro Ala Asn Phe His Gly Asn Ser Leu Ser Pro His Thr Phe Ile
                    225             230                 235

TCT GAT TTG TTC ACA AAA ACA TTC AGT AAT AGT GGC GCT ACT CCA AGT     1131
Ser Asp Leu Phe Thr Lys Thr Phe Ser Asn Ser Gly Ala Thr Pro Ser
                240             245                 250

CCT GAG CAA GAG GAT AAC TAT CTT ACA CCA TCC AAA GAT TCT AAA GAA     1179
Pro Glu Gln Glu Asp Asn Tyr Leu Thr Pro Ser Lys Asp Ser Lys Glu
            255             260                 265

GTT TTT ATT TTT CGA CCG GGC GAT TAT ATT TAC ACT TTT GAA CAG CCA     1227
Val Phe Ile Phe Arg Pro Gly Asp Tyr Ile Tyr Thr Phe Glu Gln Pro
        270             275                 280

ATA TCG CAA TCT TAT CCA GAA AGT ATA AAA GCC AAT TTT GGT TCC GTG     1275
Ile Ser Gln Ser Tyr Pro Glu Ser Ile Lys Ala Asn Phe Gly Ser Val
285             290             295                 300

GAG TAT AAA CTG TCA ATA GAC ATA GAG AGG TTT GGC GCA TTC AAA TCA     1323
Glu Tyr Lys Leu Ser Ile Asp Ile Glu Arg Phe Gly Ala Phe Lys Ser
                305             310                 315

ACT ATA CAT ACT CAA TTA CCC ATC AAA GTC GTA AGG CTT CCT TCT GAT     1371
Thr Ile His Thr Gln Leu Pro Ile Lys Val Val Arg Leu Pro Ser Asp
            320             325                 330

GGA TCC GTA GAA GAG ACT GAA GCT ATT GCA ATT TCC AAG GAC TGG AAA     1419
Gly Ser Val Glu Glu Thr Glu Ala Ile Ala Ile Ser Lys Asp Trp Lys
        335             340                 345

GAT CTT CTT CAT TAT GAC GTG GTA ATT TTC TCG AAA GAG ATC GTT TTG     1467
Asp Leu Leu His Tyr Asp Val Val Ile Phe Ser Lys Glu Ile Val Leu
350             355                 360

AAT GCA TTT TTA CCC ATC GAT TTC CAT TTC GCT CCT CTA GAT AAA GTT     1515
Asn Ala Phe Leu Pro Ile Asp Phe His Phe Ala Pro Leu Asp Lys Val
365                 370             375                 380

ACT CTG CAT CGT ATT AGA ATT TAT CTA ACA GAG TCT ATG GAA TAC ACT     1563
Thr Leu His Arg Ile Arg Ile Tyr Leu Thr Glu Ser Met Glu Tyr Thr
                385             390                 395

TGT AAT AGT AAT GGA AAT CAC GAG AAG GCT CGT AGA TTA GAG CCA ACT     1611
Cys Asn Ser Asn Gly Asn His Glu Lys Ala Arg Arg Leu Glu Pro Thr
                400             405                 410

AAA AAG TTT CTG TTG GCT GAA CAT AAC GGT CCT AAA CTG CCT CAT ATA     1659
Lys Lys Phe Leu Leu Ala Glu His Asn Gly Pro Lys Leu Pro His Ile
        415             420                 425

CCA GCT GGT TCG AAT CCT TTG AAG GCT AAA AAT AGA GGG AAC ATC CTC     1707
Pro Ala Gly Ser Asn Pro Leu Lys Ala Lys Asn Arg Gly Asn Ile Leu
        430             435                 440

TTG GAT GAA AAA TCC GGC GAT CTA GTT AAC AAA GAT TTT CAG TTC GAG     1755
Leu Asp Glu Lys Ser Gly Asp Leu Val Asn Lys Asp Phe Gln Phe Glu
445             450                 455                 460

GTG TTT GTC CCA AGC AAG TTT ACA AAC AGT ATA CGG TTA CAC CCT GAT     1803
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Val | Phe | Val | Pro | Ser<br>465 | Lys | Phe | Thr | Asn | Ser<br>470 | Ile | Arg | Leu | His | Pro<br>475 | Asp |      |
| ACA<br>Thr | AAT<br>Asn | TAT<br>Tyr | GAT<br>Asp<br>480 | AAA<br>Lys | ATC<br>Ile | AAA<br>Lys | GCC<br>Ala | CAC<br>His<br>485 | CAT<br>His | TGG<br>Trp | ATA<br>Ile | AAA<br>Lys | ATT<br>Ile<br>490 | TGC<br>Cys | CTT<br>Leu | 1851 |
| CGT<br>Arg | CTT<br>Leu | TCC<br>Ser<br>495 | AAG<br>Lys | AAG<br>Lys | TAC<br>Tyr | GGG<br>Gly | GAC<br>Asp<br>500 | AAT<br>Asn | AGA<br>Arg | AAA<br>Lys | CAT<br>His | TTC<br>Phe<br>505 | GAA<br>Glu | ATA<br>Ile | AGT<br>Ser | 1899 |
| ATT<br>Ile | GAT<br>Asp | TCT<br>Ser<br>510 | CCA<br>Pro | ATC<br>Ile | CAT<br>His | ATT<br>Ile<br>515 | TTA<br>Leu | AAT<br>Asn | CAA<br>Gln | CTA<br>Leu | TGC<br>Cys<br>520 | TCA<br>Ser | CAC<br>His | GCG<br>Ala | AAT<br>Asn | 1947 |
| ACT<br>Thr<br>525 | TTG<br>Leu | CTA<br>Leu | CCG<br>Pro | AGC<br>Ser | TAC<br>Tyr<br>530 | GAG<br>Glu | AGT<br>Ser | CAT<br>His | TTC<br>Phe | CAG<br>Gln<br>535 | TAT<br>Tyr | TGT<br>Cys | GAT<br>Asp | GAA<br>Glu | GAT<br>Asp<br>540 | 1995 |
| GGT<br>Gly | AAT<br>Asn | TTC<br>Phe | GCA<br>Ala | CCA<br>Pro<br>545 | GCA<br>Ala | GCA<br>Ala | GAT<br>Asp | CAA<br>Gln | CAA<br>Gln<br>550 | AAT<br>Asn | TAC<br>Tyr | GCA<br>Ala | AGT<br>Ser | CAT<br>His<br>555 | CAT<br>His | 2043 |
| GAT<br>Asp | TCC<br>Ser | AAT<br>Asn | ATT<br>Ile<br>560 | TTC<br>Phe | TTC<br>Phe | CCA<br>Pro | AAA<br>Lys | GAA<br>Glu<br>565 | GTT<br>Val | CTT<br>Leu | TCG<br>Ser | TCT<br>Ser | CCC<br>Pro<br>570 | GTT<br>Val | CTT<br>Leu | 2091 |
| TCA<br>Ser | CCT<br>Pro | AAC<br>Asn<br>575 | GTG<br>Val | CAG<br>Gln | AAG<br>Lys | ATG<br>Met | AAC<br>Asn<br>580 | ATT<br>Ile | AGA<br>Arg | ATA<br>Ile | CCG<br>Pro | TCT<br>Ser<br>585 | GAT<br>Asp | CTT<br>Leu | CCA<br>Pro | 2139 |
| GTA<br>Val | GTG<br>Val<br>590 | CGT<br>Arg | AAT<br>Asn | AGA<br>Arg | GCT<br>Ala | GAA<br>Glu<br>595 | AGC<br>Ser | GTA<br>Val | AAG<br>Lys | AAA<br>Lys | AGC<br>Ser<br>600 | AAG<br>Lys | TCA<br>Ser | GAT<br>Asp | AAT<br>Asn | 2187 |
| ACC<br>Thr<br>605 | TCC<br>Ser | AAG<br>Lys | AAG<br>Lys | AAT<br>Asn | GAT<br>Asp<br>610 | CAA<br>Gln | AGT<br>Ser | AGC<br>Ser | AAT<br>Asn | GTC<br>Val<br>615 | TTC<br>Phe | GCA<br>Ala | TCC<br>Ser | AAA<br>Lys | CAG<br>Gln<br>620 | 2235 |
| CTG<br>Leu | GTC<br>Val | GCA<br>Ala | AAC<br>Asn | ATT<br>Ile<br>625 | TAT<br>Tyr | AAG<br>Lys | CCC<br>Pro | AAT<br>Asn | CAG<br>Gln<br>630 | ATT<br>Ile | CCA<br>Pro | AGA<br>Arg | GAA<br>Glu | TTA<br>Leu<br>635 | ACT<br>Thr | 2283 |
| TCT<br>Ser | CCT<br>Pro | CAG<br>Gln | GCG<br>Ala<br>640 | TTA<br>Leu | CCA<br>Pro | TTA<br>Leu | TCG<br>Ser | CCC<br>Pro<br>645 | ATC<br>Ile | ACC<br>Thr | TCA<br>Ser | CCA<br>Pro | ATT<br>Ile<br>650 | CTC<br>Leu | AAT<br>Asn | 2331 |
| TAC<br>Tyr | CAA<br>Gln | CCA<br>Pro<br>655 | TTA<br>Leu | TCA<br>Ser | AAC<br>Asn | TCC<br>Ser | CCG<br>Pro<br>660 | CCT<br>Pro | CCA<br>Pro | GAT<br>Asp | TTT<br>Phe | GAT<br>Asp<br>665 | TTT<br>Phe | GAT<br>Asp | CTA<br>Leu | 2379 |
| GCT<br>Ala | AAG<br>Lys<br>670 | CGC<br>Arg | GGC<br>Gly | GCA<br>Ala | GCC<br>Ala | GAT<br>Asp<br>675 | TCT<br>Ser | CAT<br>His | GCT<br>Ala | ATT<br>Ile | CCT<br>Pro<br>680 | GTG<br>Val | GAT<br>Asp | CCT<br>Pro | CCA<br>Pro | 2427 |
| TCA<br>Ser<br>685 | TAT<br>Tyr | TTT<br>Phe | GAT<br>Asp | GTA<br>Val | TTA<br>Leu<br>690 | AAG<br>Lys | GCC<br>Ala | GAT<br>Asp | GGG<br>Gly | ATT<br>Ile<br>695 | GAA<br>Glu | TTG<br>Leu | CCA<br>Pro | TAC<br>Tyr | TAC<br>Tyr<br>700 | 2475 |
| GAT<br>Asp | ACA<br>Thr | AGT<br>Ser | TCA<br>Ser | TCT<br>Ser<br>705 | AAA<br>Lys | ATT<br>Ile | CCT<br>Pro | GAA<br>Glu | CTA<br>Leu<br>710 | AAA<br>Lys | CTA<br>Leu | AAC<br>Asn | AAA<br>Lys | TCT<br>Ser<br>715 | AGA<br>Arg | 2523 |
| GAG<br>Glu | ACA<br>Thr | TTG<br>Leu | GCC<br>Ala<br>720 | AGC<br>Ser | ATT<br>Ile | GAG<br>Glu | GAG<br>Glu | GAC<br>Asp<br>725 | TCA<br>Ser | TTC<br>Phe | AAT<br>Asn | GGT<br>Gly | TGG<br>Trp<br>730 | TCT<br>Ser | CAA<br>Gln | 2571 |
| ATT<br>Ile | GAT<br>Asp | GAC<br>Asp<br>735 | TTA<br>Leu | TCC<br>Ser | GAC<br>Asp | GAA<br>Glu | GAT<br>Asp<br>740 | GAC<br>Asp | AAT<br>Asn | GAT<br>Asp | GGC<br>Gly | GAT<br>Asp<br>745 | ATA<br>Ile | GCA<br>Ala | TCT<br>Ser | 2619 |
| GGT<br>Gly | TTC<br>Phe<br>750 | AAC<br>Asn | TTC<br>Phe | AAG<br>Lys | CTG<br>Leu | TCA<br>Ser<br>755 | ACC<br>Thr | AGT<br>Ser | GCT<br>Ala | CCG<br>Pro | AGT<br>Ser<br>760 | GAG<br>Glu | AAC<br>Asn | GTT<br>Val | AAT<br>Asn | 2667 |
| TCA<br>Ser<br>765 | CAC<br>His | ACT<br>Thr | CCT<br>Pro | ATT<br>Ile | TTG<br>Leu<br>770 | CAG<br>Gln | TCT<br>Ser | TTA<br>Leu | AAC<br>Asn | ATG<br>Met<br>775 | AGT<br>Ser | CTT<br>Leu | GAT<br>Asp | GGG<br>Gly | AGA<br>Arg<br>780 | 2715 |
| AAA<br> | AAA<br> | AAT<br> | CGT<br> | GCC<br> | AGT<br> | CTA<br> | CAC<br> | GCA<br> | ACA<) | TCA<) | GTG<) | TTA<) | CCT<) | AGT<) | ACA<) | 2763 |

| | | | | Lys | Lys | Asn | Arg | Ala | Ser | Leu | His | Ala | Thr | Ser | Val | Leu | Pro | Ser | Thr | |
|---|---|---|---|---|---|---|---|---|---|---|---|---|---|---|---|---|---|---|---|---|
| | | | | | | | | 785 | | | | 790 | | | | | | 795 | | |

| ATA | AGA | CAG | AAC | AAT | CAG | CAT | TTC | AAT | GAC | ATA | AAC | CAG | ATG | CTA | GGC | 2811 |
|---|---|---|---|---|---|---|---|---|---|---|---|---|---|---|---|---|
| Ile | Arg | Gln | Asn | Asn | Gln | His | Phe | Asn | Asp | Ile | Asn | Gln | Met | Leu | Gly | |
| | | | 800 | | | | | 805 | | | | | 810 | | | |

| AGT | AGT | GAC | GAA | GAT | GCC | TTT | CCC | AAA | AGC | CAA | TCA | TTA | AAT | TTC | AAT | 2859 |
|---|---|---|---|---|---|---|---|---|---|---|---|---|---|---|---|---|
| Ser | Ser | Asp | Glu | Asp | Ala | Phe | Pro | Lys | Ser | Gln | Ser | Leu | Asn | Phe | Asn | |
| | | 815 | | | | | 820 | | | | | 825 | | | | |

| AAG | AAA | CTA | CCA | ATA | CTT | AAA | ATT | AAT | GAT | AAC | GTC | ATA | CAA | TCA | AAC | 2907 |
|---|---|---|---|---|---|---|---|---|---|---|---|---|---|---|---|---|
| Lys | Lys | Leu | Pro | Ile | Leu | Lys | Ile | Asn | Asp | Asn | Val | Ile | Gln | Ser | Asn | |
| | 830 | | | | | 835 | | | | | 840 | | | | | |

| AGC | AAT | AGT | AAT | AAC | AGA | GTT | GAT | AAT | CCA | GAA | GAT | ACA | GTG | GAT | TCT | 2955 |
|---|---|---|---|---|---|---|---|---|---|---|---|---|---|---|---|---|
| Ser | Asn | Ser | Asn | Asn | Arg | Val | Asp | Asn | Pro | Glu | Asp | Thr | Val | Asp | Ser | |
| 845 | | | | | 850 | | | | | 855 | | | | | 860 | |

| TCA | GTC | GAT | ATT | ACA | GCA | TTT | TAT | GAT | CCA | AGA | ATG | TCA | TCA | GAT | TCC | 3003 |
|---|---|---|---|---|---|---|---|---|---|---|---|---|---|---|---|---|
| Ser | Val | Asp | Ile | Thr | Ala | Phe | Tyr | Asp | Pro | Arg | Met | Ser | Ser | Asp | Ser | |
| | | | | 865 | | | | | 870 | | | | | 875 | | |

| AAA | TTT | GAT | TGG | GAG | GTA | AGC | AAG | AAC | CAT | GTT | GAC | CCA | GCA | GCC | TAC | 3051 |
|---|---|---|---|---|---|---|---|---|---|---|---|---|---|---|---|---|
| Lys | Phe | Asp | Trp | Glu | Val | Ser | Lys | Asn | His | Val | Asp | Pro | Ala | Ala | Tyr | |
| | | | 880 | | | | | 885 | | | | | 890 | | | |

| TCG | GTT | AAC | GTT | GCT | AGT | GAA | AAC | CGT | GTA | CTG | GAC | GAC | TTT | AAG | AAA | 3099 |
|---|---|---|---|---|---|---|---|---|---|---|---|---|---|---|---|---|
| Ser | Val | Asn | Val | Ala | Ser | Glu | Asn | Arg | Val | Leu | Asp | Asp | Phe | Lys | Lys | |
| | | 895 | | | | | 900 | | | | | 905 | | | | |

| GCA | TTT | CGC | GAA | AAG | AGA | AAA | TAAGTACATT | ATTTTCATTC | TCCGACAGAA | 3150 |
|---|---|---|---|---|---|---|---|---|---|---|
| Ala | Phe | Arg | Glu | Lys | Arg | Lys | | | | |
| | 910 | | | | | 915 | | | | |

```
TTGCTACCAT TTTACTTTGT GTCCTGTGAT TCAATAGTGT ACAATATATT GGACATTTTA     3210

TAGTATACAA ATATACACCA TCAATCTATA CATCCATATC ACTTGTCGTA AAGATATCCC     3270

TTTTTAATAG TACAGCGATT AAAAAAATAA CATGATTAAC GTTCAGTTAC CAATGAGCTT     3330

ATTTATTAGG CTTGCTTTAG ATTTTTCCAA GTCAATTTTT GTTTTTCTA ACGCTTGCAA      3390

CCTCATCTCA ACCTTCTTCC TTTGCAAGCA GATCTTCGAA ACCATCTCGT TTATTCTCTC     3450

AATGCTGTTC CCACTTTCAT CATCGTCTGG GAAAAGTACC GGTAAGGGCG                3500
```

(2) INFORMATION FOR SEQ ID NO:5:

(i) SEQUENCE CHARACTERISTICS:
        (A) LENGTH: 915 amino acids
        (B) TYPE: amino acid
        (D) TOPOLOGY: linear (ii) MOLECULE TYPE: protein (xi) SEQUENCE DESCRIPTION: SEQ ID NO:5:

| Met | Leu | Gln | Phe | Asn | Thr | Glu | Asn | Asp | Thr | Val | Ala | Pro | Val | Phe | Pro |
|---|---|---|---|---|---|---|---|---|---|---|---|---|---|---|---|
| 1 | | | | 5 | | | | | 10 | | | | | 15 | |

| Met | Glu | Gln | Asp | Ile | Asn | Ala | Ala | Pro | Asp | Ala | Val | Pro | Leu | Val | Gln |
|---|---|---|---|---|---|---|---|---|---|---|---|---|---|---|---|
| | | | 20 | | | | | 25 | | | | | 30 | | |

| Thr | Thr | Thr | Leu | Gln | Val | Phe | Val | Lys | Leu | Ala | Glu | Pro | Ile | Val | Phe |
|---|---|---|---|---|---|---|---|---|---|---|---|---|---|---|---|
| | | 35 | | | | | 40 | | | | | 45 | | | |

| Leu | Lys | Gly | Phe | Glu | Thr | Asn | Gly | Leu | Ser | Glu | Ile | Ala | Pro | Ser | Ile |
|---|---|---|---|---|---|---|---|---|---|---|---|---|---|---|---|
| | 50 | | | | | 55 | | | | | 60 | | | | |

| Leu | Arg | Gly | Ser | Leu | Ile | Val | Arg | Val | Leu | Lys | Pro | Asn | Lys | Leu | Lys |
|---|---|---|---|---|---|---|---|---|---|---|---|---|---|---|---|
| 65 | | | | | 70 | | | | | 75 | | | | | 80 |

| Ser | Ile | Ser | Ile | Thr | Phe | Lys | Gly | Ile | Ser | Arg | Thr | Glu | Trp | Pro | Glu |
|---|---|---|---|---|---|---|---|---|---|---|---|---|---|---|---|
| | | | | 85 | | | | | 90 | | | | | 95 | |

| Gly | Ile | Pro | Pro | Lys | Arg | Glu | Glu | Phe | Ser | Asp | Val | Glu | Thr | Val | Val |
|---|---|---|---|---|---|---|---|---|---|---|---|---|---|---|---|
| | | | 100 | | | | | 105 | | | | | 110 | | |

-continued

| | | | | | | | | | | | | | | |
|---|---|---|---|---|---|---|---|---|---|---|---|---|---|---|
|Asn|His|Thr 115|Trp|Pro|Phe|Tyr 120|Gln|Ala|Asp|Asp|Gly 125|Met|Asn|Ser|Phe|
|Thr|Leu 130|Glu|His|His|Ser 135|Ser|Asn|Asn|Ser|Ser 140|Asn|Arg|Pro|Ser|Met|
|Ser 145|Asp|Glu|Asp|Tyr 150|Leu|Leu|Glu|Lys|Ser 155|Gly|Ala|Ser|Val|Tyr|Ile 160|
|Pro|Pro|Thr|Ala|Glu 165|Pro|Pro|Lys|Asp|Asn 170|Ser|Asn|Leu|Ser|Leu 175|Asp|
|Ala|Tyr|Glu|Arg 180|Asn|Ser|Leu|Ser|Ser 185|Asp|Asn|Leu|Ser|Asn 190|Lys|Pro|
|Val|Ser|Ser 195|Asp|Val|Ser|His|Asp 200|Asp|Ser|Lys|Leu|Leu 205|Ala|Ile|Gln|
|Lys|Thr 210|Pro|Leu|Pro|Ser|Ser 215|Ser|Arg|Arg|Gly|Ser 220|Val|Pro|Ala|Asn|
|Phe 225|His|Gly|Asn|Ser|Leu 230|Ser|Pro|His|Thr|Phe 235|Ile|Ser|Asp|Leu|Phe 240|
|Thr|Lys|Thr|Phe|Ser 245|Asn|Ser|Gly|Ala|Thr 250|Pro|Ser|Pro|Glu|Gln 255|Glu|
|Asp|Asn|Tyr|Leu 260|Thr|Pro|Ser|Lys|Asp 265|Ser|Lys|Glu|Val|Phe 270|Ile|Phe|
|Arg|Pro|Gly 275|Asp|Tyr|Ile|Tyr|Thr 280|Phe|Glu|Gln|Pro|Ile 285|Ser|Gln|Ser|
|Tyr|Pro 290|Glu|Ser|Ile|Lys|Ala 295|Asn|Phe|Gly|Ser|Val 300|Glu|Tyr|Lys|Leu|
|Ser 305|Ile|Asp|Ile|Glu|Arg 310|Phe|Gly|Ala|Phe|Lys 315|Ser|Thr|Ile|His|Thr 320|
|Gln|Leu|Pro|Ile|Lys 325|Val|Val|Arg|Leu|Pro 330|Ser|Asp|Gly|Ser|Val 335|Glu|
|Glu|Thr|Glu|Ala 340|Ile|Ala|Ile|Ser|Lys 345|Asp|Trp|Lys|Asp|Leu 350|Leu|His|
|Tyr|Asp|Val 355|Val|Ile|Phe|Ser|Lys 360|Glu|Ile|Val|Leu|Asn 365|Ala|Phe|Leu|
|Pro|Ile 370|Asp|Phe|His|Phe|Ala 375|Pro|Leu|Asp|Lys|Val 380|Thr|Leu|His|Arg|
|Ile 385|Arg|Ile|Tyr|Leu|Thr 390|Glu|Ser|Met|Glu|Tyr 395|Thr|Cys|Asn|Ser|Asn 400|
|Gly|Asn|His|Glu|Lys 405|Ala|Arg|Arg|Leu|Glu 410|Pro|Thr|Lys|Lys|Phe 415|Leu|
|Leu|Ala|Glu|His 420|Asn|Gly|Pro|Lys|Leu 425|Pro|His|Ile|Pro|Ala 430|Gly|Ser|
|Asn|Pro|Leu 435|Lys|Ala|Lys|Asn|Arg 440|Gly|Asn|Ile|Leu|Leu 445|Asp|Glu|Lys|
|Ser|Gly 450|Asp|Leu|Val|Asn|Lys 455|Asp|Phe|Gln|Phe|Glu 460|Val|Phe|Val|Pro|
|Ser|Lys 465|Phe|Thr|Asn|Ser 470|Ile|Arg|Leu|His|Pro 475|Asp|Thr|Asn|Tyr|Asp 480|
|Lys|Ile|Lys|Ala|His 485|His|Trp|Ile|Lys|Ile 490|Cys|Leu|Arg|Leu|Ser 495|Lys|
|Lys|Tyr|Gly|Asp 500|Asn|Arg|Lys|His|Phe 505|Glu|Ile|Ser|Ile|Asp 510|Ser|Pro|
|Ile|His|Ile 515|Leu|Asn|Gln|Leu|Cys 520|Ser|His|Ala|Asn|Thr 525|Leu|Leu|Pro|
|Ser|Tyr 530|Glu|Ser|His|Phe|Gln 535|Tyr|Cys|Asp|Glu|Asp 540|Gly|Asn|Phe|Ala|

```
Pro  Ala  Ala  Asp  Gln  Gln  Asn  Tyr  Ala  Ser  His  His  Asp  Ser  Asn  Ile
545                      550                 555                           560

Phe  Phe  Pro  Lys  Glu  Val  Leu  Ser  Ser  Pro  Val  Leu  Ser  Pro  Asn  Val
                    565                      570                      575

Gln  Lys  Met  Asn  Ile  Arg  Ile  Pro  Ser  Asp  Leu  Pro  Val  Val  Arg  Asn
               580                      585                      590

Arg  Ala  Glu  Ser  Val  Lys  Lys  Ser  Lys  Ser  Asp  Asn  Thr  Ser  Lys  Lys
          595                      600                 605

Asn  Asp  Gln  Ser  Ser  Asn  Val  Phe  Ala  Ser  Lys  Gln  Leu  Val  Ala  Asn
          610                 615                      620

Ile  Tyr  Lys  Pro  Asn  Gln  Ile  Pro  Arg  Glu  Leu  Thr  Ser  Pro  Gln  Ala
625                      630                      635                      640

Leu  Pro  Leu  Ser  Pro  Ile  Thr  Ser  Pro  Ile  Leu  Asn  Tyr  Gln  Pro  Leu
                    645                      650                      655

Ser  Asn  Ser  Pro  Pro  Pro  Asp  Phe  Asp  Phe  Asp  Leu  Ala  Lys  Arg  Gly
               660                 665                      670

Ala  Ala  Asp  Ser  His  Ala  Ile  Pro  Val  Asp  Pro  Pro  Ser  Tyr  Phe  Asp
               675                 680                      685

Val  Leu  Lys  Ala  Asp  Gly  Ile  Glu  Leu  Pro  Tyr  Tyr  Asp  Thr  Ser  Ser
     690                      695                      700

Ser  Lys  Ile  Pro  Glu  Leu  Lys  Leu  Asn  Lys  Ser  Arg  Glu  Thr  Leu  Ala
705                      710                      715                      720

Ser  Ile  Glu  Glu  Asp  Ser  Phe  Asn  Gly  Trp  Ser  Gln  Ile  Asp  Asp  Leu
                    725                      730                      735

Ser  Asp  Glu  Asp  Asp  Asn  Asp  Gly  Asp  Ile  Ala  Ser  Gly  Phe  Asn  Phe
               740                      745                      750

Lys  Leu  Ser  Thr  Ser  Ala  Pro  Ser  Glu  Asn  Val  Asn  Ser  His  Thr  Pro
          755                      760                      765

Ile  Leu  Gln  Ser  Leu  Asn  Met  Ser  Leu  Asp  Gly  Arg  Lys  Lys  Asn  Arg
     770                      775                      780

Ala  Ser  Leu  His  Ala  Thr  Ser  Val  Leu  Pro  Ser  Thr  Ile  Arg  Gln  Asn
785                      790                      795                      800

Asn  Gln  His  Phe  Asn  Asp  Ile  Asn  Gln  Met  Leu  Gly  Ser  Ser  Asp  Glu
               805                      810                      815

Asp  Ala  Phe  Pro  Lys  Ser  Gln  Ser  Leu  Asn  Phe  Asn  Lys  Lys  Leu  Pro
               820                      825                      830

Ile  Leu  Lys  Ile  Asn  Asp  Asn  Val  Ile  Gln  Ser  Asn  Ser  Asn  Ser  Asn
          835                      840                      845

Asn  Arg  Val  Asp  Asn  Pro  Glu  Asp  Thr  Val  Asp  Ser  Ser  Val  Asp  Ile
     850                      855                      860

Thr  Ala  Phe  Tyr  Asp  Pro  Arg  Met  Ser  Ser  Asp  Ser  Lys  Phe  Asp  Trp
865                      870                      875                      880

Glu  Val  Ser  Lys  Asn  His  Val  Asp  Pro  Ala  Ala  Tyr  Ser  Val  Asn  Val
               885                      890                      895

Ala  Ser  Glu  Asn  Arg  Val  Leu  Asp  Asp  Phe  Lys  Lys  Ala  Phe  Arg  Glu
               900                      905                      910

Lys  Arg  Lys
          915
```

( 2 ) INFORMATION FOR SEQ ID NO:6:

( i ) SEQUENCE CHARACTERISTICS:
        ( A ) LENGTH: 2745 base pairs
        ( B ) TYPE: nucleic acid
        ( C ) STRANDEDNESS: double (D) TOPOLOGY: unknown (ii) MOLECULE TYPE: cDNA to mRNA (iii) HYPOTHETICAL: NO (iv) ANTI-SENSE: NO (vi) ORIGINAL SOURCE:
(C) INDIVIDUAL ISOLATE: coding sequence of CNI (xi) SEQUENCE DESCRIPTION: SEQ ID NO:6:

| | | | | | | |
|---|---|---|---|---|---|---|
| ATGCTCCAAT | TCAATACAGA | AAATGATACT | GTAGCTCCAG | TGTTTCCCAT | GGAGCAAGAT | 60 |
| ATAAATGCAG | CACCTGATGC | CGTCCCACTG | GTGCAGACAA | CAACACTACA | AGTCTTTGTA | 120 |
| AAGCTTGCCG | AACCCATAGT | GTTTTTAAAA | GGATTTGAAA | CTAACGGACT | GTCTGAAATA | 180 |
| GCCCCCAGTA | TCTTACGAGG | ATCTCTTATC | GTCAGGGTGT | TGAAACCGAA | TAAATTAAAA | 240 |
| AGTATATCGA | TAACCTTCAA | AGGAATATCC | AGAACAGAGT | GGCCGGAAGG | TATACCACCG | 300 |
| AAGAGAGAAG | AATTTTCAGA | TGTTGAAACT | GTTGTCAATC | ACACATGGCC | ATTTTATCAG | 360 |
| GCGGATGACG | GCATGAATTC | TTTCACCTTA | GAACATCACA | GCTCAAATAA | TTCGTCCAAT | 420 |
| CGCCCATCTA | TGAGCGATGA | AGATTATCTA | CTTGAAAAAA | GCGGTGCTTC | AGTATATATC | 480 |
| CCACCAACCG | CTGAACCCCC | TAAAGATAAT | AGCAATCTAA | GTCTGGATGC | CTATGAGCGC | 540 |
| AACTCATTGT | CATCCGATAA | TTTGAGTAAC | AAGCCAGTAT | CAAGTGATGT | TCCCATGAC | 600 |
| GACAGTAAAC | TGTTGGCTAT | TCAAAAGACA | CCATTACCAT | CATCTAGTCG | AAGAGGATCG | 660 |
| GTACCGGCAA | ATTTTCACGG | TAACTCTTTG | TCACCTCATA | CCTTCATATC | TGATTTGTTC | 720 |
| ACAAAAACAT | TCAGTAATAG | TGGCGCTACT | CCAAGTCCTG | AGCAAGAGGA | TAACTATCTT | 780 |
| ACACCATCCA | AAGATTCTAA | AGAAGTTTTT | ATTTTCGAC | GGGCGATTA | TATTTACACT | 840 |
| TTGAACAGC | CAATATCGCA | ATCTTATCCA | GAAAGTATAA | AAGCCAATTT | TGGTTCCGTG | 900 |
| GAGTATAAAC | TGTCAATAGA | CATAGAGAGG | TTTGGCGCAT | TCAAATCAAC | TATACATACT | 960 |
| CAATTACCCA | TCAAAGTCGT | AAGGCTTCCT | TCTGATGGAT | CCGTAGAAGA | GACTGAAGCT | 1020 |
| ATTGCAATTT | CCAAGGACTG | GAAAGATCTT | CTTCATTATG | ACGTGGTAAT | TTTCTCGAAA | 1080 |
| GAGATCGTTT | TGAATGCATT | TTTACCCATC | GATTTCCATT | TCGCTCCTCT | AGATAAAGTT | 1140 |
| ACTCTGCATC | GTATTAGAAT | TTATCTAACA | GAGTCTATGG | AATACACTTG | TAATAGTAAT | 1200 |
| GGAAATCACG | AGAAGGCTCG | TAGATTAGAG | CCAACTAAAA | AGTTTCTGTT | GGCTGAACAT | 1260 |
| AACGGTCCTA | AACTGCCTCA | TATACCAGCT | GGTTCGAATC | CTTTGAAGGC | TAAAAATAGA | 1320 |
| GGGAACATCC | TCTTGGATGA | AAAATCCGGC | GATCTAGTTA | ACAAAGATTT | TCAGTTCGAG | 1380 |
| GTGTTTGTCC | CAAGCAAGTT | TACAAACAGT | ATACGGTTAC | ACCCTGATAC | AAATTATGAT | 1440 |
| AAAATCAAAG | CCCACCATTG | GATAAAAATT | TGCCTTCGTC | TTTCCAAGAA | GTACGGGGAC | 1500 |
| AATAGAAAAC | ATTTCGAAAT | AAGTATTGAT | TCTCCAATCC | ATATTTAAA | TCAACTATGC | 1560 |
| TCACACGCGA | ATACTTTGCT | ACCGAGCTAC | GAGAGTCATT | TCCAGTATTG | TGATGAAGAT | 1620 |
| GGTAATTTCG | CACCAGCAGC | AGATCAACAA | AATTACGCAA | GTCATCATGA | TTCCAATATT | 1680 |
| TTCTTCCCAA | AAGAAGTTCT | TTCGTCTCCC | GTTCTTTCAC | CTAACGTGCA | GAAGATGAAC | 1740 |
| ATTAGAATAC | CGTCTGATCT | TCCAGTAGTG | CGTAATAGAG | CTGAAAGCGT | AAAGAAAAGC | 1800 |
| AAGTCAGATA | ATACCTCCAA | GAAGAATGAT | CAAAGTAGCA | ATGTCTTCGC | ATCCAAACAG | 1860 |
| CTGGTCGCAA | ACATTTATAA | GCCCAATCAG | ATTCCAAGAG | AATTAACTTC | TCCTCAGGCG | 1920 |
| TTACCATTAT | CGCCCATCAC | CTCACCAATT | CTCAATTACC | AACCATTATC | AAACTCCCCG | 1980 |
| CCTCCAGATT | TTGATTTTGA | TCTAGCTAAG | CGCGGCGCAG | CCGATTCTCA | TGCTATTCCT | 2040 |

-continued

```
GTGGATCCTC  CATCATATTT  TGATGTATTA  AAGGCCGATG  GGATTGAATT  GCCATACTAC    2100
GATACAAGTT  CATCTAAAAT  TCCTGAACTA  AAACTAAACA  AATCTAGAGA  GACATTGGCC    2160
AGCATTGAGG  AGGACTCATT  CAATGGTTGG  TCTCAAATTG  ATGACTTATC  CGACGAAGAT    2220
GACAATGATG  GCGATATAGC  ATCTGGTTTC  AACTTCAAGC  TGTCAACCAG  TGCTCCGAGT    2280
GAGAACGTTA  ATTCACACAC  TCCTATTTTG  CAGTCTTTAA  ACATGAGTCT  TGATGGGAGA    2340
AAAAAAAATC  GTGCCAGTCT  ACACGCAACA  TCAGTGTTAC  CTAGTACAAT  AAGACAGAAC    2400
AATCAGCATT  TCAATGACAT  AAACCAGATG  CTAGGCAGTA  GTGACGAAGA  TGCCTTTCCC    2460
AAAAGCCAAT  CATTAAATTT  CAATAAGAAA  CTACCAATAC  TTAAAATTAA  TGATAACGTC    2520
ATACAATCAA  ACAGCAATAG  TAATAACAGA  GTTGATAATC  CAGAAGATAC  AGTGGATTCT    2580
TCAGTCGATA  TTACAGCATT  TTATGATCCA  AGAATGTCAT  CAGATTCCAA  ATTTGATTGG    2640
GAGGTAAGCA  AGAACCATGT  TGACCCAGCA  GCCTACTCGG  TTAACGTTGC  TAGTGAAAAC    2700
CGTGTACTGG  ACGACTTTAA  GAAAGCATTT  CGCGAAAAGA  GAAAA                     2745
```

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: CNI-PRC-A (xi) SEQUENCE DESCRIPTION: SEQ ID NO:7:

```
CCAAAAAAAG  AGATCTCGGA  TCAAAGTAGC                                          30
```

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: CNI-PCR-B (xi) SEQUENCE DESCRIPTION: SEQ ID NO:8:

```
GGGTTTTTCA  GTGTCGACGA  TTCATAGATC                                          30
```

(2) INFORMATION FOR SEQ ID NO:9:

(i) SEQUENCE CHARACTERISTICS:
        (A) LENGTH: 1964 base pairs
        (B) TYPE: nucleic acid
        (C) STRANDEDNESS: double
        (D) TOPOLOGY: unknown (ii) MOLECULE TYPE: DNA (genomic)

( i i i ) HYPOTHETICAL: NO ( i v ) ANTI-SENSE: NO ( v i ) ORIGINAL SOURCE:
    ( C ) INDIVIDUAL ISOLATE: genomic DNA fragment containing full CNA1 coding sequence ( i x ) FEATURE:
    ( A ) NAME/KEY: CDS
    ( B ) LOCATION: 286..1944

( x i ) SEQUENCE DESCRIPTION: SEQ ID NO:9:

```
GTTTGTTGCA TTTTGATATT CATCTATATC TATTTCAAAA TTTTTCATGT CATCGCCTCT      60

TGAAACATGA ATTTTCCAAT TCTGAAAAAG AACGTACTAC TGGGAAACAA AAGGGAAAAA     120

TGTATAAATC CTTTAATGTT TTTGAATCAA GAGGCATTAT TATAAAAGAA CGAAGCAAAG     180

CCTTTAATAT TTGCTTTATT AAAGGTATTA TTCAAAGAAA AGTTTTTTA GATTCTTTTT      240

TTTTTGACGT ATTAGCTCAG CTGCCATAAA ACACTCTCAA CGCCA ATG TCG AAA         294
                                                 Met Ser Lys
                                                  1

GAC TTG AAT TCT TCA CGC ATC AAA ATC ATT AAA CCT AAT GAC TCT TAC      342
Asp Leu Asn Ser Ser Arg Ile Lys Ile Ile Lys Pro Asn Asp Ser Tyr
      5              10                  15

ATA AAG GTT GAC CGG AAA AAA GAT TTA ACA AAA TAC GAA TTA GAA AAC      390
Ile Lys Val Asp Arg Lys Lys Asp Leu Thr Lys Tyr Glu Leu Glu Asn
 20              25                  30                  35

GGT AAA GTA ATT TCT ACT AAG GAC CGA TCC TAC GCT TCT GTA CCT GCC      438
Gly Lys Val Ile Ser Thr Lys Asp Arg Ser Tyr Ala Ser Val Pro Ala
                 40                  45                  50

ATA ACA GGA AAG ATA CCA AGT GAT GAG GAA GTA TTC GAC TCC AAG ACG      486
Ile Thr Gly Lys Ile Pro Ser Asp Glu Glu Val Phe Asp Ser Lys Thr
             55                  60                  65

GGA TTA CCT AAT CAT TCC TTT TTA AGA GAG CAT TTC TTT CAT GAG GGT      534
Gly Leu Pro Asn His Ser Phe Leu Arg Glu His Phe Phe His Glu Gly
         70                  75                  80

CGA CTT TCT AAG GAA CAG GCC ATA AAA ATC TTA AAT ATG TCA ACT GTA      582
Arg Leu Ser Lys Glu Gln Ala Ile Lys Ile Leu Asn Met Ser Thr Val
     85                  90                  95

GCA TTG AGT AAA GAA CCC AAT CTA CTA AAA CTC AAA GCG CCA ATT ACT      630
Ala Leu Ser Lys Glu Pro Asn Leu Leu Lys Leu Lys Ala Pro Ile Thr
100                 105                 110                 115

ATA TGT GGT GAT ATT CAC GGG CAG TAT TAT GAT TTA TTG AAA CTG TTT      678
Ile Cys Gly Asp Ile His Gly Gln Tyr Tyr Asp Leu Leu Lys Leu Phe
                120                 125                 130

GAA GTT GGC GGT GAC CCC GCC GAA ATC GAC TAT TTA TTC TTG GGG GAT      726
Glu Val Gly Gly Asp Pro Ala Glu Ile Asp Tyr Leu Phe Leu Gly Asp
            135                 140                 145

TAT GTT GAT AGA GGT GCA TTC TCT TTT GAG TGT CTG ATT TAT TTG TAC      774
Tyr Val Asp Arg Gly Ala Phe Ser Phe Glu Cys Leu Ile Tyr Leu Tyr
        150                 155                 160

TCC TTG AAG TTG AAT AAT TTA GGG AGA TTT TGG ATG CTA AGA GGT AAC      822
Ser Leu Lys Leu Asn Asn Leu Gly Arg Phe Trp Met Leu Arg Gly Asn
    165                 170                 175

CAT GAG TGT AAG CAC TTG ACC TCT TAT TTT ACT TTT AAG AAT GAG ATG      870
His Glu Cys Lys His Leu Thr Ser Tyr Phe Thr Phe Lys Asn Glu Met
180                 185                 190                 195

TTG CAC AAA TAC GAT ATG GAA GTT TAC GAT GCT TGC TGC AGA TCA TTC      918
Leu His Lys Tyr Asp Met Glu Val Tyr Asp Ala Cys Cys Arg Ser Phe
                200                 205                 210

AAT GTC TTA CCA TTA GCA GCT TTA ATG AAC GGA CAA TAT TTT TGT GTG      966
Asn Val Leu Pro Leu Ala Ala Leu Met Asn Gly Gln Tyr Phe Cys Val
```

|  |  |  |  |  |  |  |  |  |  |  |  |  |  |  |  |
|---|---|---|---|---|---|---|---|---|---|---|---|---|---|---|---|
|  |  |  | 215 |  |  |  |  | 220 |  |  |  |  | 225 |  |  |
| CAT | GGT | GGT | ATC | TCT | CCA | GAG | TTA | AAA | TCA | GTA | GAG | GAT | GTT | AAT | AAA |
| His | Gly | Gly | Ile | Ser | Pro | Glu | Leu | Lys | Ser | Val | Glu | Asp | Val | Asn | Lys |
|  |  | 230 |  |  |  |  | 235 |  |  |  |  | 240 |  |  |  |

1014

| ATT | AAT | AGA | TTT | CGA | GAA | ATC | CCA | TCT | CGT | GGT | CTC | ATG | TGT | GAC | CTA |
|---|---|---|---|---|---|---|---|---|---|---|---|---|---|---|---|
| Ile | Asn | Arg | Phe | Arg | Glu | Ile | Pro | Ser | Arg | Gly | Leu | Met | Cys | Asp | Leu |
|  |  | 245 |  |  |  |  | 250 |  |  |  |  | 255 |  |  |  |

1062

| CTA | TGG | GCC | GAT | CCT | GTC | GAA | AAT | TAT | GAT | GAT | GCA | AGA | GAT | GGT | AGC |
|---|---|---|---|---|---|---|---|---|---|---|---|---|---|---|---|
| Leu | Trp | Ala | Asp | Pro | Val | Glu | Asn | Tyr | Asp | Asp | Ala | Arg | Asp | Gly | Ser |
| 260 |  |  |  |  | 265 |  |  |  |  | 270 |  |  |  |  | 275 |

1110

| GAA | TTT | GAT | CAG | AGC | GAG | GAT | GAA | TTC | GTA | CCT | AAC | AGT | TTG | AGG | GGT |
|---|---|---|---|---|---|---|---|---|---|---|---|---|---|---|---|
| Glu | Phe | Asp | Gln | Ser | Glu | Asp | Glu | Phe | Val | Pro | Asn | Ser | Leu | Arg | Gly |
|  |  |  |  | 280 |  |  |  |  | 285 |  |  |  |  | 290 |  |

1158

| TGC | TCT | TTC | GCC | TTC | ACT | TTT | AAA | GCA | TCA | TGC | AAG | TTT | TTG | AAG | GCA |
|---|---|---|---|---|---|---|---|---|---|---|---|---|---|---|---|
| Cys | Ser | Phe | Ala | Phe | Thr | Phe | Lys | Ala | Ser | Cys | Lys | Phe | Leu | Lys | Ala |
|  |  |  |  | 295 |  |  |  |  | 300 |  |  |  |  | 305 |  |

1206

| AAT | GGT | TTG | TTA | TCT | ATT | ATT | AGA | GCA | CAC | GAA | GCA | CAG | GAT | GCT | GGG |
|---|---|---|---|---|---|---|---|---|---|---|---|---|---|---|---|
| Asn | Gly | Leu | Leu | Ser | Ile | Ile | Arg | Ala | His | Glu | Ala | Gln | Asp | Ala | Gly |
|  |  | 310 |  |  |  |  | 315 |  |  |  |  | 320 |  |  |  |

1254

| TAC | AGA | ATG | TAT | AAA | AAC | AAT | AAA | GTA | ACA | GGC | TTC | CCG | AGC | TTA | ATA |
|---|---|---|---|---|---|---|---|---|---|---|---|---|---|---|---|
| Tyr | Arg | Met | Tyr | Lys | Asn | Asn | Lys | Val | Thr | Gly | Phe | Pro | Ser | Leu | Ile |
|  | 325 |  |  |  |  | 330 |  |  |  |  | 335 |  |  |  |  |

1302

| ACC | ATG | TTC | AGT | GCG | CCA | AAC | TAC | CTG | GAC | ACA | TAT | CAT | AAT | AAA | GCT |
|---|---|---|---|---|---|---|---|---|---|---|---|---|---|---|---|
| Thr | Met | Phe | Ser | Ala | Pro | Asn | Tyr | Leu | Asp | Thr | Tyr | His | Asn | Lys | Ala |
| 340 |  |  |  |  | 345 |  |  |  |  | 350 |  |  |  |  | 355 |

1350

| GCT | GTG | TTA | AAA | TAT | GAA | GAA | AAC | GTC | ATG | AAC | ATC | AGG | CAG | TTT | CAC |
|---|---|---|---|---|---|---|---|---|---|---|---|---|---|---|---|
| Ala | Val | Leu | Lys | Tyr | Glu | Glu | Asn | Val | Met | Asn | Ile | Arg | Gln | Phe | His |
|  |  |  |  | 360 |  |  |  |  | 365 |  |  |  |  | 370 |  |

1398

| ATG | TCT | CCG | CAC | CCT | TAC | TGG | TTG | CCT | GAT | TTT | ATG | GAT | GTT | TTC | ACC |
|---|---|---|---|---|---|---|---|---|---|---|---|---|---|---|---|
| Met | Ser | Pro | His | Pro | Tyr | Trp | Leu | Pro | Asp | Phe | Met | Asp | Val | Phe | Thr |
|  |  |  | 375 |  |  |  |  | 380 |  |  |  |  | 385 |  |  |

1446

| TGG | TCA | CTA | CCT | TTT | GTT | GGC | GAA | AAA | GTT | ACT | AGC | ATG | TTA | GTG | TCT |
|---|---|---|---|---|---|---|---|---|---|---|---|---|---|---|---|
| Trp | Ser | Leu | Pro | Phe | Val | Gly | Glu | Lys | Val | Thr | Ser | Met | Leu | Val | Ser |
|  |  | 390 |  |  |  |  | 395 |  |  |  |  | 400 |  |  |  |

1494

| ATA | TTA | AAC | ATA | TGT | AGT | GAG | CAG | GAA | CTT | GAC | CCA | GAA | TCG | GAA | CCC |
|---|---|---|---|---|---|---|---|---|---|---|---|---|---|---|---|
| Ile | Leu | Asn | Ile | Cys | Ser | Glu | Gln | Glu | Leu | Asp | Pro | Glu | Ser | Glu | Pro |
| 405 |  |  |  |  | 410 |  |  |  |  | 415 |  |  |  |  |  |

1542

| AAA | GCT | GCG | GAG | GAG | ACT | GTA | AAG | GCA | AGA | GCA | AAC | GCA | ACT | AAG | GAG |
|---|---|---|---|---|---|---|---|---|---|---|---|---|---|---|---|
| Lys | Ala | Ala | Glu | Glu | Thr | Val | Lys | Ala | Arg | Ala | Asn | Ala | Thr | Lys | Glu |
| 420 |  |  |  |  | 425 |  |  |  |  | 430 |  |  |  |  | 435 |

1590

| ACC | GGC | ACC | CCA | TCT | GAT | GAA | AAG | GCG | TCA | TCA | GCG | ATA | TTA | GAA | GAT |
|---|---|---|---|---|---|---|---|---|---|---|---|---|---|---|---|
| Thr | Gly | Thr | Pro | Ser | Asp | Glu | Lys | Ala | Ser | Ser | Ala | Ile | Leu | Glu | Asp |
|  |  |  |  | 440 |  |  |  |  | 445 |  |  |  |  | 450 |  |

1638

| GAA | ACC | CGA | AGA | AAG | GCT | TTG | AGA | AAT | AAG | ATA | TTA | GCT | ATT | GCT | AAA |
|---|---|---|---|---|---|---|---|---|---|---|---|---|---|---|---|
| Glu | Thr | Arg | Arg | Lys | Ala | Leu | Arg | Asn | Lys | Ile | Leu | Ala | Ile | Ala | Lys |
|  |  | 455 |  |  |  |  | 460 |  |  |  |  | 465 |  |  |  |

1686

| GTT | TCA | AGA | ATG | TTT | TCG | GTG | CTA | AGA | GAA | GAG | AGC | GAA | AAA | GTG | GAA |
|---|---|---|---|---|---|---|---|---|---|---|---|---|---|---|---|
| Val | Ser | Arg | Met | Phe | Ser | Val | Leu | Arg | Glu | Glu | Ser | Glu | Lys | Val | Glu |
|  |  | 470 |  |  |  |  | 475 |  |  |  |  | 480 |  |  |  |

1734

| TAT | TTG | AAA | ACT | ATG | AAT | GCC | GGT | GTC | TTA | CCT | CGT | GGT | GCT | CTA | GCT |
|---|---|---|---|---|---|---|---|---|---|---|---|---|---|---|---|
| Tyr | Leu | Lys | Thr | Met | Asn | Ala | Gly | Val | Leu | Pro | Arg | Gly | Ala | Leu | Ala |
| 485 |  |  |  |  | 490 |  |  |  |  | 495 |  |  |  |  |  |

1782

| CGT | GGG | ACT | GAA | GGT | TTG | AAT | GAA | ACG | CTA | AGC | ACT | TTT | GAA | AAG | GCT |
|---|---|---|---|---|---|---|---|---|---|---|---|---|---|---|---|
| Arg | Gly | Thr | Glu | Gly | Leu | Asn | Glu | Thr | Leu | Ser | Thr | Phe | Glu | Lys | Ala |
| 500 |  |  |  |  | 505 |  |  |  |  | 510 |  |  |  |  | 515 |

1830

| AGA | AAG | GAA | GAC | CTT | ATT | AAT | GAA | AAA | TTA | CCA | CCA | TCT | TTA | TCG | GAG |
|---|---|---|---|---|---|---|---|---|---|---|---|---|---|---|---|
| Arg | Lys | Glu | Asp | Leu | Ile | Asn | Glu | Lys | Leu | Pro | Pro | Ser | Leu | Ser | Glu |
|  |  |  |  | 520 |  |  |  |  | 525 |  |  |  |  | 530 |  |

1878

| GTT | GAA | CAA | GAG | AAG | ATT | AAA | TAC | TAC | GAA | AAA | ATA | TTA | AAG | GGA | GCG |
|---|---|---|---|---|---|---|---|---|---|---|---|---|---|---|---|
| Val | Glu | Gln | Glu | Lys | Ile | Lys | Tyr | Tyr | Glu | Lys | Ile | Leu | Lys | Gly | Ala |

1926

-continued

```
                  535                           540                           545
GAG AAA AAG CCA CAA CTG TGATAAATCT TCATTTTATT                                                                    1964
Glu Lys Lys Pro Gln Leu
            550
```

( 2 ) INFORMATION FOR SEQ ID NO:10:

( i ) SEQUENCE CHARACTERISTICS:
        ( A ) LENGTH: 553 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Ser Lys Asp Leu Asn Ser Ser Arg Ile Lys Ile Ile Lys Pro Asn
 1               5                  10                      15

Asp Ser Tyr Ile Lys Val Asp Arg Lys Lys Asp Leu Thr Lys Tyr Glu
            20                  25                  30

Leu Glu Asn Gly Lys Val Ile Ser Thr Lys Asp Arg Ser Tyr Ala Ser
        35                  40                  45

Val Pro Ala Ile Thr Gly Lys Ile Pro Ser Asp Glu Val Phe Asp
    50                  55                  60

Ser Lys Thr Gly Leu Pro Asn His Ser Phe Leu Arg Glu His Phe Phe
65                  70                  75                  80

His Glu Gly Arg Leu Ser Lys Glu Gln Ala Ile Lys Ile Leu Asn Met
                85                  90                  95

Ser Thr Val Ala Leu Ser Lys Glu Pro Asn Leu Leu Lys Leu Lys Ala
                100                 105                 110

Pro Ile Thr Ile Cys Gly Asp Ile His Gly Gln Tyr Tyr Asp Leu Leu
            115                 120                 125

Lys Leu Phe Glu Val Gly Gly Asp Pro Ala Glu Ile Asp Tyr Leu Phe
130                 135                 140

Leu Gly Asp Tyr Val Asp Arg Gly Ala Phe Ser Phe Glu Cys Leu Ile
145                 150                 155                 160

Tyr Leu Tyr Ser Leu Lys Leu Asn Asn Leu Gly Arg Phe Trp Met Leu
                165                 170                 175

Arg Gly Asn His Glu Cys Lys His Leu Thr Ser Tyr Phe Thr Phe Lys
            180                 185                 190

Asn Glu Met Leu His Lys Tyr Asp Met Glu Val Tyr Asp Ala Cys Cys
            195                 200                 205

Arg Ser Phe Asn Val Leu Pro Leu Ala Ala Leu Met Asn Gly Gln Tyr
    210                 215                 220

Phe Cys Val His Gly Gly Ile Ser Pro Glu Leu Lys Ser Val Glu Asp
225                 230                 235                 240

Val Asn Lys Ile Asn Arg Phe Arg Glu Ile Pro Ser Arg Gly Leu Met
                245                 250                 255

Cys Asp Leu Leu Trp Ala Asp Pro Val Glu Asn Tyr Asp Asp Ala Arg
            260                 265                 270

Asp Gly Ser Glu Phe Asp Gln Ser Glu Asp Glu Phe Val Pro Asn Ser
        275                 280                 285

Leu Arg Gly Cys Ser Phe Ala Phe Thr Phe Lys Ala Ser Cys Lys Phe
    290                 295                 300

Leu Lys Ala Asn Gly Leu Leu Ser Ile Ile Arg Ala His Glu Ala Gln
305                 310                 315                 320

Asp Ala Gly Tyr Arg Met Tyr Lys Asn Asn Lys Val Thr Gly Phe Pro
                325                 330                 335
```

| Ser | Leu | Ile | Thr | Met | Phe | Ser | Ala | Pro | Asn | Tyr | Leu | Asp | Thr | Tyr | His |
|-----|-----|-----|-----|-----|-----|-----|-----|-----|-----|-----|-----|-----|-----|-----|-----|
|     |     |     | 340 |     |     |     |     | 345 |     |     |     |     | 350 |     |     |

| Asn | Lys | Ala | Ala | Val | Leu | Lys | Tyr | Glu | Glu | Asn | Val | Met | Asn | Ile | Arg |
|-----|-----|-----|-----|-----|-----|-----|-----|-----|-----|-----|-----|-----|-----|-----|-----|
|     |     | 355 |     |     |     |     | 360 |     |     |     |     | 365 |     |     |     |

| Gln | Phe | His | Met | Ser | Pro | His | Pro | Tyr | Trp | Leu | Pro | Asp | Phe | Met | Asp |
|-----|-----|-----|-----|-----|-----|-----|-----|-----|-----|-----|-----|-----|-----|-----|-----|
|     | 370 |     |     |     |     | 375 |     |     |     |     | 380 |     |     |     |     |

| Val | Phe | Thr | Trp | Ser | Leu | Pro | Phe | Val | Gly | Glu | Lys | Val | Thr | Ser | Met |
|-----|-----|-----|-----|-----|-----|-----|-----|-----|-----|-----|-----|-----|-----|-----|-----|
| 385 |     |     |     |     | 390 |     |     |     |     | 395 |     |     |     |     | 400 |

| Leu | Val | Ser | Ile | Leu | Asn | Ile | Cys | Ser | Glu | Gln | Glu | Leu | Asp | Pro | Glu |
|-----|-----|-----|-----|-----|-----|-----|-----|-----|-----|-----|-----|-----|-----|-----|-----|
|     |     |     |     | 405 |     |     |     |     | 410 |     |     |     |     | 415 |     |

| Ser | Glu | Pro | Lys | Ala | Ala | Glu | Glu | Thr | Val | Lys | Ala | Arg | Ala | Asn | Ala |
|-----|-----|-----|-----|-----|-----|-----|-----|-----|-----|-----|-----|-----|-----|-----|-----|
|     |     |     | 420 |     |     |     |     | 425 |     |     |     |     | 430 |     |     |

| Thr | Lys | Glu | Thr | Gly | Thr | Pro | Ser | Asp | Glu | Lys | Ala | Ser | Ser | Ala | Ile |
|-----|-----|-----|-----|-----|-----|-----|-----|-----|-----|-----|-----|-----|-----|-----|-----|
|     |     | 435 |     |     |     |     | 440 |     |     |     |     | 445 |     |     |     |

| Leu | Glu | Asp | Glu | Thr | Arg | Arg | Lys | Ala | Leu | Arg | Asn | Lys | Ile | Leu | Ala |
|-----|-----|-----|-----|-----|-----|-----|-----|-----|-----|-----|-----|-----|-----|-----|-----|
|     | 450 |     |     |     |     | 455 |     |     |     |     | 460 |     |     |     |     |

| Ile | Ala | Lys | Val | Ser | Arg | Met | Phe | Ser | Val | Leu | Arg | Glu | Glu | Ser | Glu |
|-----|-----|-----|-----|-----|-----|-----|-----|-----|-----|-----|-----|-----|-----|-----|-----|
| 465 |     |     |     |     | 470 |     |     |     |     | 475 |     |     |     |     | 480 |

| Lys | Val | Glu | Tyr | Leu | Lys | Thr | Met | Asn | Ala | Gly | Val | Leu | Pro | Arg | Gly |
|-----|-----|-----|-----|-----|-----|-----|-----|-----|-----|-----|-----|-----|-----|-----|-----|
|     |     |     |     | 485 |     |     |     |     | 490 |     |     |     |     | 495 |     |

| Ala | Leu | Ala | Arg | Gly | Thr | Glu | Gly | Leu | Asn | Glu | Thr | Leu | Ser | Thr | Phe |
|-----|-----|-----|-----|-----|-----|-----|-----|-----|-----|-----|-----|-----|-----|-----|-----|
|     |     |     |     | 500 |     |     |     |     | 505 |     |     |     |     | 510 |     |

| Glu | Lys | Ala | Arg | Lys | Glu | Asp | Leu | Ile | Asn | Glu | Lys | Leu | Pro | Pro | Ser |
|-----|-----|-----|-----|-----|-----|-----|-----|-----|-----|-----|-----|-----|-----|-----|-----|
|     |     | 515 |     |     |     |     | 520 |     |     |     |     | 525 |     |     |     |

| Leu | Ser | Glu | Val | Glu | Gln | Glu | Lys | Ile | Lys | Tyr | Tyr | Glu | Lys | Ile | Leu |
|-----|-----|-----|-----|-----|-----|-----|-----|-----|-----|-----|-----|-----|-----|-----|-----|
|     | 530 |     |     |     |     | 535 |     |     |     |     | 540 |     |     |     |     |

| Lys | Gly | Ala | Glu | Lys | Lys | Pro | Gln | Leu |
|-----|-----|-----|-----|-----|-----|-----|-----|-----|
| 545 |     |     |     |     | 550 |     |     |     |

( 2 ) INFORMATION FOR SEQ ID NO:11:

( i ) SEQUENCE CHARACTERISTICS:
        ( A ) LENGTH: 2353 base pairs
        ( B ) TYPE: nucleic acid
        ( C ) STRANDEDNESS: double
        ( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: genomic DNA fragment containing full
            CNA2 coding sequence ( i x ) FEATURE:
        ( A ) NAME/KEY: CDS
        ( B ) LOCATION: 262..2073

( x i ) SEQUENCE DESCRIPTION: SEQ ID NO:11:

| ATAGTCTATA | ATACGTTTGA | TACAGCTAGA | TATCGCTAGC | GCCAACATTG | TCCCCCTCTC | 60 |
|---|---|---|---|---|---|---|
| TTGATCAATG | CTTTTTTTCG | GCCCGAGACA | AATGAGAAAA | TGTCCTAAAA | ATACCTTTCA | 120 |
| TCAAGACTCC | TATTTTTCCT | TAGAAAAAAC | ATATATCCAA | CTGGAACAGT | ATTAAGCCAA | 180 |
| TTGCTACGAT | ACAAACAAAA | GGAGATATTC | CTTCCCTCCC | ATAGAGTCAC | ACAGGAGCCA | 240 |
| GTACTTCTTC | TTGAACCCGC A | ATG TCT | TCA GAC GCT | ATA AGA | AAT ACT GAG | 291 |

Met Ser  Ser Asp Ala  Ile Arg  Asn Thr Glu
                                          1                      5                    10

| | | | | | | | | | | | | | | | | |
|---|---|---|---|---|---|---|---|---|---|---|---|---|---|---|---|---|
| CAG | ATA | AAC | GCC | GCT | ATT | AAA | ATT | ATA | GAA | AAC | AAA | ACA | GAG | CGT | CCG | 339 |
| Gln | Ile | Asn | Ala | Ala | Ile | Lys | Ile | Ile | Glu | Asn | Lys | Thr | Glu | Arg | Pro | |
| | | | | 15 | | | | | 20 | | | | | 25 | | |
| CAA | TCG | TCC | ACA | ACC | CCT | ATA | GAT | TCG | AAG | GCT | AGT | ACA | GTT | GCT | GCT | 387 |
| Gln | Ser | Ser | Thr | Thr | Pro | Ile | Asp | Ser | Lys | Ala | Ser | Thr | Val | Ala | Ala | |
| | | | 30 | | | | | 35 | | | | | 40 | | | |
| GCT | AAT | TCC | ACG | GCC | ACA | GAA | ACT | TCC | AGA | GAC | CTT | ACA | CAA | TAT | ACC | 435 |
| Ala | Asn | Ser | Thr | Ala | Thr | Glu | Thr | Ser | Arg | Asp | Leu | Thr | Gln | Tyr | Thr | |
| | | 45 | | | | | 50 | | | | | 55 | | | | |
| CTA | GAT | GAC | GGA | AGA | GTC | GTA | TCG | ACA | AAC | CGC | AGA | ATA | ATG | AAT | AAA | 483 |
| Leu | Asp | Asp | Gly | Arg | Val | Val | Ser | Thr | Asn | Arg | Arg | Ile | Met | Asn | Lys | |
| | | 60 | | | | 65 | | | | | 70 | | | | | |
| GTG | CCC | GCC | ATC | ACG | TCA | CAT | GTT | CCT | ACA | GAT | GAA | GAG | CTG | TTC | CAG | 531 |
| Val | Pro | Ala | Ile | Thr | Ser | His | Val | Pro | Thr | Asp | Glu | Glu | Leu | Phe | Gln | |
| 75 | | | | | 80 | | | | | 85 | | | | | 90 | |
| CCC | AAT | GGG | ATA | CCT | CGT | CAC | GAA | TTC | CTA | AGA | GAT | CAT | TTC | AAG | CGC | 579 |
| Pro | Asn | Gly | Ile | Pro | Arg | His | Glu | Phe | Leu | Arg | Asp | His | Phe | Lys | Arg | |
| | | | | 95 | | | | | 100 | | | | | 105 | | |
| GAG | GGC | AAA | TTG | TCG | GCT | GCG | CAG | GCG | GCC | AGG | ATC | GTT | ACA | CTT | GCA | 627 |
| Glu | Gly | Lys | Leu | Ser | Ala | Ala | Gln | Ala | Ala | Arg | Ile | Val | Thr | Leu | Ala | |
| | | | 110 | | | | | 115 | | | | | 120 | | | |
| ACG | GAA | CTC | TTC | AGC | AAA | GAA | CCC | AAC | CTT | ATA | TCT | GTT | CCC | GCC | CCA | 675 |
| Thr | Glu | Leu | Phe | Ser | Lys | Glu | Pro | Asn | Leu | Ile | Ser | Val | Pro | Ala | Pro | |
| | | 125 | | | | | 130 | | | | | 135 | | | | |
| ATC | ACA | GTT | TGC | GGT | GAT | ATC | CAT | GGC | CAG | TAC | TTT | GAC | CTT | TTG | AAG | 723 |
| Ile | Thr | Val | Cys | Gly | Asp | Ile | His | Gly | Gln | Tyr | Phe | Asp | Leu | Leu | Lys | |
| | 140 | | | | | 145 | | | | | 150 | | | | | |
| CTA | TTC | GAA | GTT | GGC | GGA | GAT | CCG | GCC | ACT | ACA | TCG | TAT | TTG | TTC | TTG | 771 |
| Leu | Phe | Glu | Val | Gly | Gly | Asp | Pro | Ala | Thr | Thr | Ser | Tyr | Leu | Phe | Leu | |
| 155 | | | | | 160 | | | | | 165 | | | | | 170 | |
| GGA | GAC | TAT | GTC | GAC | AGA | GGG | TCC | TTT | TCG | TTT | GAG | TGT | CTT | ATT | TAT | 819 |
| Gly | Asp | Tyr | Val | Asp | Arg | Gly | Ser | Phe | Ser | Phe | Glu | Cys | Leu | Ile | Tyr | |
| | | | | 175 | | | | | 180 | | | | | 185 | | |
| TTA | TAT | TCT | TTG | AAG | CTG | AAT | TTT | AAC | GAC | CAT | TTC | TGG | CTA | CTG | AGG | 867 |
| Leu | Tyr | Ser | Leu | Lys | Leu | Asn | Phe | Asn | Asp | His | Phe | Trp | Leu | Leu | Arg | |
| | | | 190 | | | | | 195 | | | | | 200 | | | |
| GGT | AAC | CAC | GAA | TGT | AAG | CAT | CTA | ACG | TCA | TAT | TTC | ACT | TTC | AAA | AAT | 915 |
| Gly | Asn | His | Glu | Cys | Lys | His | Leu | Thr | Ser | Tyr | Phe | Thr | Phe | Lys | Asn | |
| | | 205 | | | | | 210 | | | | | 215 | | | | |
| GAA | ATG | CTG | CAC | AAG | TAC | AAT | CTA | GAT | ATT | TAC | GAG | AAA | TGC | TGC | GAA | 963 |
| Glu | Met | Leu | His | Lys | Tyr | Asn | Leu | Asp | Ile | Tyr | Glu | Lys | Cys | Cys | Glu | |
| | 220 | | | | | 225 | | | | | 230 | | | | | |
| TCG | TTT | AAC | AAC | TTG | CCC | CTG | GCT | GCG | TTA | ATG | AAC | GGA | CAG | TAT | CTT | 1011 |
| Ser | Phe | Asn | Asn | Leu | Pro | Leu | Ala | Ala | Leu | Met | Asn | Gly | Gln | Tyr | Leu | |
| 235 | | | | | 240 | | | | | 245 | | | | | 250 | |
| TGT | GTT | CAT | GGT | GGT | ATA | TCT | CCC | GAG | TTA | AAC | TCT | TTA | CAG | GAC | ATT | 1059 |
| Cys | Val | His | Gly | Gly | Ile | Ser | Pro | Glu | Leu | Asn | Ser | Leu | Gln | Asp | Ile | |
| | | | | 255 | | | | | 260 | | | | | 265 | | |
| AAC | AAC | CTA | AAT | AGA | TTC | AGG | GAG | ATT | CCC | TCT | CAT | GGC | CTG | ATG | TGT | 1107 |
| Asn | Asn | Leu | Asn | Arg | Phe | Arg | Glu | Ile | Pro | Ser | His | Gly | Leu | Met | Cys | |
| | | | 270 | | | | | 275 | | | | | 280 | | | |
| GAT | CTG | TTG | TGG | GCT | GAC | CCG | ATT | GAA | GAG | TAC | GAC | GAA | GTC | TTG | GAT | 1155 |
| Asp | Leu | Leu | Trp | Ala | Asp | Pro | Ile | Glu | Glu | Tyr | Asp | Glu | Val | Leu | Asp | |
| | | 285 | | | | | 290 | | | | | 295 | | | | |
| AAA | GAC | TTG | ACT | GAG | GAA | GAC | ATA | GTG | AAC | TCC | AAA | ACC | ATG | GTT | CCT | 1203 |
| Lys | Asp | Leu | Thr | Glu | Glu | Asp | Ile | Val | Asn | Ser | Lys | Thr | Met | Val | Pro | |
| | 300 | | | | | 305 | | | | | 310 | | | | | |
| CAT | CAT | GGC | AAG | ATG | GCA | CCT | TCA | AGG | GAT | ATG | TTT | GTC | CCA | AAC | TCA | 1251 |
| His | His | Gly | Lys | Met | Ala | Pro | Ser | Arg | Asp | Met | Phe | Val | Pro | Asn | Ser | |
| 315 | | | | | 320 | | | | | 325 | | | | | 330 | |

| | | | | | | | | | | | | | | | | |
|---|---|---|---|---|---|---|---|---|---|---|---|---|---|---|---|---|
| GTA | AGG | GGC | TGT | TCA | TAT | GCC | TTC | ACG | TAT | CGT | GCT | GCG | TGC | CAT | TTT | 1299 |
| Val | Arg | Gly | Cys | Ser 335 | Tyr | Ala | Phe | Thr 340 | Tyr | Arg | Ala | Ala | Cys 345 | His | Phe | |
| CTG | CAA | GAG | ACT | GGC | CTG | TTG | TCC | ATC | ATC | AGG | GCA | CAC | GAG | GCT | CAA | 1347 |
| Leu | Gln | Glu | Thr 350 | Gly | Leu | Leu | Ser | Ile 355 | Ile | Arg | Ala | His | Glu 360 | Ala | Gln | |
| GAC | GCT | GGT | TAT | AGA | ATG | TAC | AAA | AAT | ACC | AAG | ACT | TTG | GGC | TTT | CCC | 1395 |
| Asp | Ala | Gly 365 | Tyr | Arg | Met | Tyr | Lys 370 | Asn | Thr | Lys | Thr | Leu 375 | Gly | Phe | Pro | |
| TCT | CTT | TTG | ACC | CTT | TTC | AGT | GCG | CCT | AAC | TAC | TTG | GAC | ACC | TAC | AAT | 1443 |
| Ser | Leu | Leu 380 | Thr | Leu | Phe | Ser | Ala 385 | Pro | Asn | Tyr | Leu | Asp 390 | Thr | Tyr | Asn | |
| AAT | AAG | GCT | GCC | ATA | TTG | AAA | TAC | GAA | AAT | AAT | GTT | ATG | AAT | ATC | AGA | 1491 |
| Asn 395 | Lys | Ala | Ala | Ile | Leu 400 | Lys | Tyr | Glu | Asn | Asn 405 | Val | Met | Asn | Ile | Arg 410 | |
| CAA | TTC | AAC | ATG | ACT | CCA | CAC | CCC | TAT | TGG | TTA | CCA | GAT | TTC | ATG | GAC | 1539 |
| Gln | Phe | Asn | Met | Thr 415 | Pro | His | Pro | Tyr | Trp 420 | Leu | Pro | Asp | Phe | Met 425 | Asp | |
| GTT | TTC | ACG | TGG | TCC | TTG | CCA | TTT | GTT | GGT | GAA | AAA | GTT | ACA | GAG | ATG | 1587 |
| Val | Phe | Thr | Trp 430 | Ser | Leu | Pro | Phe | Val 435 | Gly | Glu | Lys | Val | Thr 440 | Glu | Met | |
| CTT | GTC | GCA | ATT | CTA | AAC | ATC | TGT | ACT | GAA | GAT | GAG | CTG | GAA | AAC | GAC | 1635 |
| Leu | Val | Ala 445 | Ile | Leu | Asn | Ile | Cys 450 | Thr | Glu | Asp | Glu | Leu 455 | Glu | Asn | Asp | |
| ACC | CCC | GTC | ATT | GAA | GAA | TTA | GTT | GGT | ACC | GAT | AAA | AAA | TTG | CCA | CAA | 1683 |
| Thr | Pro 460 | Val | Ile | Glu | Glu | Leu 465 | Val | Gly | Thr | Asp | Lys 470 | Lys | Leu | Pro | Gln | |
| GCT | GGT | AAG | TCG | GAA | GCA | ACT | CCA | CAA | CCA | GCC | ACT | TCG | GCG | TCG | CCT | 1731 |
| Ala 475 | Gly | Lys | Ser | Glu | Ala 480 | Thr | Pro | Gln | Pro | Ala 485 | Thr | Ser | Ala | Ser | Pro 490 | |
| AAA | CAT | GCT | TCC | ATT | TTA | GAT | GAC | GAA | CAT | CGA | AGG | AAA | GCC | TTA | CGA | 1779 |
| Lys | His | Ala | Ser | Ile 495 | Leu | Asp | Asp | Glu | His 500 | Arg | Arg | Lys | Ala | Leu 505 | Arg | |
| AAT | AAG | ATT | CTG | GCC | GTC | GCC | AAA | GTT | TCC | AGA | ATG | TAT | TCT | GTT | CTC | 1827 |
| Asn | Lys | Ile | Leu 510 | Ala | Val | Ala | Lys | Val 515 | Ser | Arg | Met | Tyr | Ser 520 | Val | Leu | |
| AGA | GAA | GAA | ACC | AAT | AAA | GTT | CAG | TTT | TTA | AAA | GAT | CAC | AAT | TCA | GGC | 1875 |
| Arg | Glu | Glu 525 | Thr | Asn | Lys | Val | Gln 530 | Phe | Leu | Lys | Asp | His 535 | Asn | Ser | Gly | |
| GTG | TTG | CCA | CGT | GGC | GCT | TTA | TCT | AAT | GGT | GTA | AAG | GGT | TTA | GAT | GAA | 1923 |
| Val | Leu 540 | Pro | Arg | Gly | Ala | Leu 545 | Ser | Asn | Gly | Val | Lys 550 | Gly | Leu | Asp | Glu | |
| GCC | CTG | TCT | ACC | TTT | GAA | AGG | GCA | AGA | AAG | CAC | GAT | TTA | ATT | AAT | GAA | 1971 |
| Ala | Leu 555 | Ser | Thr | Phe | Glu | Arg 560 | Ala | Arg | Lys | His | Asp 565 | Leu | Ile | Asn | Glu 570 | |
| AAA | TTA | CCG | CCT | TCA | CTA | GAC | GAA | CTG | AAA | AAC | GAA | AAT | AAG | AAG | TAC | 2019 |
| Lys | Leu | Pro | Pro | Ser 575 | Leu | Asp | Glu | Leu | Lys 580 | Asn | Glu | Asn | Lys | Lys 585 | Tyr | |
| TAC | GAA | AAA | GTT | TGG | CAG | AAA | GTA | CAT | GAA | CAT | GAT | GCA | AAG | AAT | GAT | 2067 |
| Tyr | Glu | Lys | Val 590 | Trp | Gln | Lys | Val | His 595 | Glu | His | Asp | Ala | Lys 600 | Asn | Asp | |

| | | | | |
|---|---|---|---|---|
| AGC | AAA | TAGAGAAAGC | TCCTATTTCC | ACTGTACATA CTTCAATAAG TAAGTAAGTT | 2123 |
| Ser | Lys | | | | |
| GCATTAATTA | TCTATTTAGA | AGCTAGATGC | TCCTCAAATG | CACAGAATCA TATAGCGTTT | 2183 |
| TATTAGGTCT | GTTCTTTATT | TTAGTTTTGT | TGATCTCTAT | GAAGGTATAT TTATATGCAA | 2243 |
| AAATAAACTT | TTAAATATCT | ATGGATGCTT | ACTCAATTGT | ATAGACGTTT TTCATAGGAG | 2303 |
| TGCAAATTAT | GGACACCACC | TTCTAATTGA | GCAGAAGCGG | TTCTGAATTC | 2353 |

( 2 ) INFORMATION FOR SEQ ID NO:12:

(i) SEQUENCE CHARACTERISTICS:
   (A) LENGTH: 604 amino acids
   (B) TYPE: amino acid
   (D) TOPOLOGY: linear (ii) MOLECULE TYPE: protein (xi) SEQUENCE DESCRIPTION: SEQ ID NO:12:

```
Met Ser Ser Asp Ala Ile Arg Asn Thr Glu Gln Ile Asn Ala Ala Ile
 1               5                  10                  15

Lys Ile Ile Glu Asn Lys Thr Glu Arg Pro Gln Ser Ser Thr Thr Pro
            20                  25                  30

Ile Asp Ser Lys Ala Ser Thr Val Ala Ala Ala Asn Ser Thr Ala Thr
        35                  40                  45

Glu Thr Ser Arg Asp Leu Thr Gln Tyr Thr Leu Asp Asp Gly Arg Val
     50                  55                  60

Val Ser Thr Asn Arg Arg Ile Met Asn Lys Val Pro Ala Ile Thr Ser
 65                  70                  75                  80

His Val Pro Thr Asp Glu Glu Leu Phe Gln Pro Asn Gly Ile Pro Arg
                 85                  90                  95

His Glu Phe Leu Arg Asp His Phe Lys Arg Glu Gly Lys Leu Ser Ala
            100                 105                 110

Ala Gln Ala Ala Arg Ile Val Thr Leu Ala Thr Glu Leu Phe Ser Lys
        115                 120                 125

Glu Pro Asn Leu Ile Ser Val Pro Ala Pro Ile Thr Val Cys Gly Asp
    130                 135                 140

Ile His Gly Gln Tyr Phe Asp Leu Leu Lys Leu Phe Glu Val Gly Gly
145                 150                 155                 160

Asp Pro Ala Thr Thr Ser Tyr Leu Phe Leu Gly Asp Tyr Val Asp Arg
                165                 170                 175

Gly Ser Phe Ser Phe Glu Cys Leu Ile Tyr Leu Tyr Ser Leu Lys Leu
            180                 185                 190

Asn Phe Asn Asp His Phe Trp Leu Leu Arg Gly Asn His Glu Cys Lys
        195                 200                 205

His Leu Thr Ser Tyr Phe Thr Phe Lys Asn Glu Met Leu His Lys Tyr
    210                 215                 220

Asn Leu Asp Ile Tyr Glu Lys Cys Cys Glu Ser Phe Asn Asn Leu Pro
225                 230                 235                 240

Leu Ala Ala Leu Met Asn Gly Gln Tyr Leu Cys Val His Gly Gly Ile
                245                 250                 255

Ser Pro Glu Leu Asn Ser Leu Gln Asp Ile Asn Asn Leu Asn Arg Phe
            260                 265                 270

Arg Glu Ile Pro Ser His Gly Leu Met Cys Asp Leu Leu Trp Ala Asp
        275                 280                 285

Pro Ile Glu Glu Tyr Asp Glu Val Leu Asp Lys Leu Thr Glu Glu
    290                 295                 300

Asp Ile Val Asn Ser Lys Thr Met Val Pro His His Gly Lys Met Ala
305                 310                 315                 320

Pro Ser Arg Asp Met Phe Val Pro Asn Ser Val Arg Gly Cys Ser Tyr
                325                 330                 335

Ala Phe Thr Tyr Arg Ala Ala Cys His Phe Leu Gln Glu Thr Gly Leu
            340                 345                 350

Leu Ser Ile Ile Arg Ala His Glu Ala Gln Asp Ala Gly Tyr Arg Met
        355                 360                 365

Tyr Lys Asn Thr Lys Thr Leu Gly Phe Pro Ser Leu Leu Thr Leu Phe
```

-continued

|  |  |  | 370 |  |  |  | 375 |  |  |  | 380 |  |  |  |
|---|---|---|---|---|---|---|---|---|---|---|---|---|---|---|
| Ser | Ala | Pro | Asn | Tyr | Leu | Asp | Thr | Tyr | Asn | Asn | Lys | Ala | Ala | Ile | Leu |
| 385 |  |  |  |  | 390 |  |  |  | 395 |  |  |  |  |  | 400 |
| Lys | Tyr | Glu | Asn | Asn | Val | Met | Asn | Ile | Arg | Gln | Phe | Asn | Met | Thr | Pro |
|  |  |  |  | 405 |  |  |  |  | 410 |  |  |  |  | 415 |  |
| His | Pro | Tyr | Trp | Leu | Pro | Asp | Phe | Met | Asp | Val | Phe | Thr | Trp | Ser | Leu |
|  |  |  | 420 |  |  |  |  | 425 |  |  |  |  | 430 |  |  |
| Pro | Phe | Val | Gly | Glu | Lys | Val | Thr | Glu | Met | Leu | Val | Ala | Ile | Leu | Asn |
|  |  | 435 |  |  |  |  | 440 |  |  |  |  | 445 |  |  |  |
| Ile | Cys | Thr | Glu | Asp | Glu | Leu | Glu | Asn | Asp | Thr | Pro | Val | Ile | Glu | Glu |
|  | 450 |  |  |  |  | 455 |  |  |  |  | 460 |  |  |  |  |
| Leu | Val | Gly | Thr | Asp | Lys | Lys | Leu | Pro | Gln | Ala | Gly | Lys | Ser | Glu | Ala |
| 465 |  |  |  |  | 470 |  |  |  | 475 |  |  |  |  |  | 480 |
| Thr | Pro | Gln | Pro | Ala | Thr | Ser | Ala | Ser | Pro | Lys | His | Ala | Ser | Ile | Leu |
|  |  |  |  | 485 |  |  |  |  | 490 |  |  |  |  | 495 |  |
| Asp | Asp | Glu | His | Arg | Arg | Lys | Ala | Leu | Arg | Asn | Lys | Ile | Leu | Ala | Val |
|  |  |  | 500 |  |  |  |  | 505 |  |  |  |  | 510 |  |  |
| Ala | Lys | Val | Ser | Arg | Met | Tyr | Ser | Val | Leu | Arg | Glu | Glu | Thr | Asn | Lys |
|  |  | 515 |  |  |  |  | 520 |  |  |  |  | 525 |  |  |  |
| Val | Gln | Phe | Leu | Lys | Asp | His | Asn | Ser | Gly | Val | Leu | Pro | Arg | Gly | Ala |
|  | 530 |  |  |  |  | 535 |  |  |  |  | 540 |  |  |  |  |
| Leu | Ser | Asn | Gly | Val | Lys | Gly | Leu | Asp | Glu | Ala | Leu | Ser | Thr | Phe | Glu |
| 545 |  |  |  |  | 550 |  |  |  | 555 |  |  |  |  |  | 560 |
| Arg | Ala | Arg | Lys | His | Asp | Leu | Ile | Asn | Glu | Lys | Leu | Pro | Pro | Ser | Leu |
|  |  |  |  | 565 |  |  |  |  | 570 |  |  |  |  | 575 |  |
| Asp | Glu | Leu | Lys | Asn | Glu | Asn | Lys | Lys | Tyr | Tyr | Glu | Lys | Val | Trp | Gln |
|  |  |  | 580 |  |  |  |  | 585 |  |  |  |  | 590 |  |  |
| Lys | Val | His | Glu | His | Asp | Ala | Lys | Asn | Asp | Ser | Lys |  |  |  |  |
|  |  | 595 |  |  |  |  | 600 |  |  |  |  |  |  |  |  |

( 2 ) INFORMATION FOR SEQ ID NO:13:

( i ) SEQUENCE CHARACTERISTICS:
        ( A ) LENGTH: 812 base pairs
        ( B ) TYPE: nucleic acid
        ( C ) STRANDEDNESS: double
        ( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: genomic DNA fragment containing full
            CNB1 coding sequence ( i x ) FEATURE:
        ( A ) NAME/KEY: CDS
        ( B ) LOCATION: 54..104

( i x ) FEATURE:
        ( A ) NAME/KEY: CDS
        ( B ) LOCATION: 181..652

( x i ) SEQUENCE DESCRIPTION: SEQ ID NO:13:

```
ACTTGGTAAC TCAATGGTGA TCAGAATCCA TAGAAGCATT TTTATTTCTT AAA ATG        56
                                                           Met
                                                           1

GGT GCT GCT CCT TCC AAA ATT GTG GAT GGT CTT TTA GAA GAT ACA AAT      104
Gly Ala Ala Pro Ser Lys Ile Val Asp Gly Leu Leu Glu Asp Thr Asn
        5               10                  15
```

```
TGTATGTACA CTTCGGAGTG AGGAAAAGAA AGAAAGGGGA AATTAACCGA TTTTACTAAC        164

ACTGACACTT TGAACA GTT GAT AGA GAT GAA ATT GAA AGG TTA AGG AAG            213
               Val Asp Arg Asp Glu Ile Glu Arg Leu Arg Lys
                 1           5                      10

AGA TTC ATG AAA TTA GAT AGA GAT AGC TCA GGG TCT ATT GAT AAA AAT          261
Arg Phe Met Lys Leu Asp Arg Asp Ser Ser Gly Ser Ile Asp Lys Asn
             15              20                  25

GAA TTT ATG AGC ATT CCT GGC GTT TCG TCA AAC CCT CTT GCT GGA CGT          309
Glu Phe Met Ser Ile Pro Gly Val Ser Ser Asn Pro Leu Ala Gly Arg
         30              35                  40

ATA ATG GAG GTT TTC GAT GCT GAT AAT AGT GGG GAC GTG GAT TTT CAA          357
Ile Met Glu Val Phe Asp Ala Asp Asn Ser Gly Asp Val Asp Phe Gln
     45              50                  55

GAG TTC ATC ACA GGA TTA TCC ATT TTC AGT GGG CGT GGG TCC AAG GAC          405
Glu Phe Ile Thr Gly Leu Ser Ile Phe Ser Gly Arg Gly Ser Lys Asp
 60              65                  70                  75

GAA AAG TTA AGA TTC GCC TTC AAA ATC TAC GAC ATT GAC AAG GAC GGT          453
Glu Lys Leu Arg Phe Ala Phe Lys Ile Tyr Asp Ile Asp Lys Asp Gly
             80              85                  90

TTC ATA TCC AAT GGT GAG TTG TTC ATC GTG TTG AAG ATT ATG GTA GGT          501
Phe Ile Ser Asn Gly Glu Leu Phe Ile Val Leu Lys Ile Met Val Gly
         95              100                 105

TCT AAT CTG GAC GAT GAA CAG CTG CAA CAG ATA GTA GAT AGG ACG ATA          549
Ser Asn Leu Asp Asp Glu Gln Leu Gln Gln Ile Val Asp Arg Thr Ile
     110             115                 120

GTG GAA AAC GAT AGC GAC GGC GAC GGA CGT TTA AGT TTC GAG GAG TTT          597
Val Glu Asn Asp Ser Asp Gly Asp Gly Arg Leu Ser Phe Glu Glu Phe
 125             130                 135

AAG AAT GCT ATC GAA ACC ACA GAA GTG GCC AAG AGT CTG ACA TTG CAA          645
Lys Asn Ala Ile Glu Thr Thr Glu Val Ala Lys Ser Leu Thr Leu Gln
 140             145                 150                 155

TAC GATGTGTAAG ACTAGGGGAC ACTTCATTCA TTTATGGTAT GCCAATATTT               698
Tyr Asp
TTAAGAAAAG AAGAATAATA CGCGATATTG TTTTTAAGG AAGGAACGCA CACTCGCCCA         758

GTTAGAGTGC TGATGATATA TACATATATA TATGTATATG TAACAAACAA TAAG              812
```

( 2 ) INFORMATION FOR SEQ ID NO:14:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met Gly Ala Ala Pro Ser Lys Ile Val Asp Gly Leu Leu Glu Asp Thr
 1               5                   10                  15
Asn
```

( 2 ) INFORMATION FOR SEQ ID NO:15:

( i ) SEQUENCE CHARACTERISTICS:
        ( A ) LENGTH: 157 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Val Asp Arg Asp Glu Ile Glu Arg Leu Arg Lys Arg Phe Met Lys Leu
 1               5                   10                  15
```

| | | | | | | | | | | | | | | |
|---|---|---|---|---|---|---|---|---|---|---|---|---|---|---|
| Asp | Arg | Asp | Ser | Ser | Gly | Ser | Ile | Asp | Lys | Asn | Glu | Phe | Met | Ser | Ile |
| | | | 20 | | | | | 25 | | | | | 30 | | |
| Pro | Gly | Val | Ser | Ser | Asn | Pro | Leu | Ala | Gly | Arg | Ile | Met | Glu | Val | Phe |
| | | 35 | | | | | 40 | | | | | 45 | | | |
| Asp | Ala | Asp | Asn | Ser | Gly | Asp | Val | Asp | Phe | Gln | Glu | Phe | Ile | Thr | Gly |
| | 50 | | | | | 55 | | | | | 60 | | | | |
| Leu | Ser | Ile | Phe | Ser | Gly | Arg | Gly | Ser | Lys | Asp | Glu | Lys | Leu | Arg | Phe |
| 65 | | | | | 70 | | | | | 75 | | | | | 80 |
| Ala | Phe | Lys | Ile | Tyr | Asp | Ile | Asp | Lys | Asp | Gly | Phe | Ile | Ser | Asn | Gly |
| | | | | 85 | | | | | 90 | | | | | 95 | |
| Glu | Leu | Phe | Ile | Val | Leu | Lys | Ile | Met | Val | Gly | Ser | Asn | Leu | Asp | Asp |
| | | | 100 | | | | | 105 | | | | | 110 | | |
| Glu | Gln | Leu | Gln | Gln | Ile | Val | Asp | Arg | Thr | Ile | Val | Glu | Asn | Asp | Ser |
| | | | 115 | | | | | 120 | | | | | 125 | | |
| Asp | Gly | Asp | Gly | Arg | Leu | Ser | Phe | Glu | Glu | Phe | Lys | Asn | Ala | Ile | Glu |
| | | 130 | | | | | 135 | | | | | 140 | | | |
| Thr | Thr | Glu | Val | Ala | Lys | Ser | Leu | Thr | Leu | Gln | Tyr | Asp | | | |
| 145 | | | | | 150 | | | | | 155 | | | | | |

( 2 ) INFORMATION FOR SEQ ID NO:16:

( i ) SEQUENCE CHARACTERISTICS:
        ( A ) LENGTH: 524 base pairs
        ( B ) TYPE: nucleic acid
        ( C ) STRANDEDNESS: double
        ( D ) TOPOLOGY: unknown ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: coding sequence of CNB1

( i x ) FEATURE:
        ( A ) NAME/KEY: CDS
        ( B ) LOCATION: 1..524

( x i ) SEQUENCE DESCRIPTION: SEQ ID NO:16:

| | | | | | | | | | | | | | | | | |
|---|---|---|---|---|---|---|---|---|---|---|---|---|---|---|---|---|
| ATG | GGT | GCT | GCT | CCT | TCC | AAA | ATT | GTG | GAT | GGT | CTT | TTA | GAA | GAT | ACA | 48 |
| Met | Gly | Ala | Ala | Pro | Ser | Lys | Ile | Val | Asp | Gly | Leu | Leu | Glu | Asp | Thr | |
| 1 | | | | 5 | | | | | 10 | | | | | 15 | | |
| AAT | TTT | GAT | AGA | GAT | GAA | ATT | GAA | AGG | TTA | AGG | AAG | AGA | TTC | ATG | AAA | 96 |
| Asn | Phe | Asp | Arg | Asp | Glu | Ile | Glu | Arg | Leu | Arg | Lys | Arg | Phe | Met | Lys | |
| | | | 20 | | | | | 25 | | | | | 30 | | | |
| TTA | GAT | AGA | GAT | AGC | TCA | GGG | TCT | ATT | GAT | AAA | AAT | GAA | TTT | ATG | AGC | 144 |
| Leu | Asp | Arg | Asp | Ser | Ser | Gly | Ser | Ile | Asp | Lys | Asn | Glu | Phe | Met | Ser | |
| | | 35 | | | | | 40 | | | | | 45 | | | | |
| ATT | CCT | GGC | GTT | TCG | TCA | AAC | CCT | CTT | GCT | GGA | CGT | ATA | ATG | GAG | GTT | 192 |
| Ile | Pro | Gly | Val | Ser | Ser | Asn | Pro | Leu | Ala | Gly | Arg | Ile | Met | Glu | Val | |
| | 50 | | | | | 55 | | | | | 60 | | | | | |
| TTC | GAT | GCT | GAT | AAT | AGT | GGG | GAC | GTG | GAT | TTT | CAA | GAG | TTC | ATC | ACA | 240 |
| Phe | Asp | Ala | Asp | Asn | Ser | Gly | Asp | Val | Asp | Phe | Gln | Glu | Phe | Ile | Thr | |
| 65 | | | | | 70 | | | | | 75 | | | | | 80 | |
| GGA | TTA | TCC | ATT | TTC | AGT | GGG | CGT | GGG | TCC | AAG | GAC | GAA | AAG | TTA | AGA | 288 |
| Gly | Leu | Ser | Ile | Phe | Ser | Gly | Arg | Gly | Ser | Lys | Asp | Glu | Lys | Leu | Arg | |
| | | | | 85 | | | | | 90 | | | | | 95 | | |
| TTC | GCC | TTC | AAA | ATC | TAC | GAC | ATT | GAC | AAG | GAC | GGT | TTC | ATA | TCC | AAT | 336 |
| Phe | Ala | Phe | Lys | Ile | Tyr | Asp | Ile | Asp | Lys | Asp | Gly | Phe | Ile | Ser | Asn | |
| | | | 100 | | | | | 105 | | | | | 110 | | | |

```
GGT GAG TTG TTC ATC GTG TTG AAG ATT ATG GTA GGT TCT AAT CTG GAC        384
Gly Glu Leu Phe Ile Val Leu Lys Ile Met Val Gly Ser Asn Leu Asp
        115                     120                 125

GAT GAA CAG CTG CAA CAG ATA GTA GAT AGG ACG ATA GTG GAA AAC GAT        432
Asp Glu Gln Leu Gln Gln Ile Val Asp Arg Thr Ile Val Glu Asn Asp
    130                     135                 140

AGC GAC GGC GAC GGA CGT TTA AGT TTC GAG GAG TTT AAG AAT GCT ATC        480
Ser Asp Gly Asp Gly Arg Leu Ser Phe Glu Glu Phe Lys Asn Ala Ile
145                     150                 155                 160

GAA ACC ACA GAA GTG GCC AAG AGT CTG ACA TTG CAA TAC GAT GT             524
Glu Thr Thr Glu Val Ala Lys Ser Leu Thr Leu Gln Tyr Asp
                165                 170
```

( 2 ) INFORMATION FOR SEQ ID NO:17:

( i ) SEQUENCE CHARACTERISTICS:
        ( A ) LENGTH: 174 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Met Gly Ala Ala Pro Ser Lys Ile Val Asp Gly Leu Leu Glu Asp Thr
 1               5                  10                  15

Asn Phe Asp Arg Asp Glu Ile Glu Arg Leu Arg Lys Arg Phe Met Lys
            20                  25                  30

Leu Asp Arg Asp Ser Ser Gly Ser Ile Asp Lys Asn Glu Phe Met Ser
         35                  40                  45

Ile Pro Gly Val Ser Ser Asn Pro Leu Ala Gly Arg Ile Met Glu Val
     50                  55                  60

Phe Asp Ala Asp Asn Ser Gly Asp Val Asp Phe Gln Glu Phe Ile Thr
 65                  70                  75                  80

Gly Leu Ser Ile Phe Ser Gly Arg Gly Ser Lys Asp Glu Lys Leu Arg
                 85                  90                  95

Phe Ala Phe Lys Ile Tyr Asp Ile Asp Lys Asp Gly Phe Ile Ser Asn
             100                 105                 110

Gly Glu Leu Phe Ile Val Leu Lys Ile Met Val Gly Ser Asn Leu Asp
         115                 120                 125

Asp Glu Gln Leu Gln Gln Ile Val Asp Arg Thr Ile Val Glu Asn Asp
     130                 135                 140

Ser Asp Gly Asp Gly Arg Leu Ser Phe Glu Glu Phe Lys Asn Ala Ile
145                 150                 155                 160

Glu Thr Thr Glu Val Ala Lys Ser Leu Thr Leu Gln Tyr Asp
                165                 170
```

( 2 ) INFORMATION FOR SEQ ID NO:18:

( i ) SEQUENCE CHARACTERISTICS:
        ( A ) LENGTH: 1812 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: DNA fragment containing
        CNA1deltaC coding sequence ( i x ) FEATURE:
    ( A ) NAME/KEY: CDS
    ( B ) LOCATION: 286..1812

( x i ) SEQUENCE DESCRIPTION: SEQ ID NO:18:

```
GTTTGTTGCA TTTTGATATT CATCTATATC TATTTCAAAA TTTTTCATGT CATCGCCTCT        60

TGAAACATGA ATTTTCCAAT TCTGAAAAAG AACGTACTAC TGGGAAACAA AAGGGAAAAA       120

TGTATAAATC CTTTAATGTT TTTGAATCAA GAGGCATTAT TATAAAAGAA CGAAGCAAAG       180

CCTTTAATAT TTGCTTTATT AAAGGTATTA TTCAAAGAAA AGTTTTTTA GATTCTTTTT        240

TTTTTGACGT ATTAGCTCAG CTGCCATAAA ACACTCTCAA CGCCA ATG TCG AAA           294
                                                 Met Ser Lys
                                                   1

GAC TTG AAT TCT TCA CGC ATC AAA ATC ATT AAA CCT AAT GAC TCT TAC         342
Asp Leu Asn Ser Ser Arg Ile Lys Ile Ile Lys Pro Asn Asp Ser Tyr
      5               10                  15

ATA AAG GTT GAC CGG AAA AAA GAT TTA ACA AAA TAC GAA TTA GAA AAC         390
Ile Lys Val Asp Arg Lys Lys Asp Leu Thr Lys Tyr Glu Leu Glu Asn
 20              25                  30                      35

GGT AAA GTA ATT TCT ACT AAG GAC CGA TCC TAC GCT TCT GTA CCT GCC         438
Gly Lys Val Ile Ser Thr Lys Asp Arg Ser Tyr Ala Ser Val Pro Ala
                 40                  45                  50

ATA ACA GGA AAG ATA CCA AGT GAT GAG GAA GTA TTC GAC TCC AAG ACG         486
Ile Thr Gly Lys Ile Pro Ser Asp Glu Glu Val Phe Asp Ser Lys Thr
                     55                  60              65

GGA TTA CCT AAT CAT TCC TTT TTA AGA GAG CAT TTC TTT CAT GAG GGT         534
Gly Leu Pro Asn His Ser Phe Leu Arg Glu His Phe Phe His Glu Gly
             70                  75                  80

CGA CTT TCT AAG GAA CAG GCC ATA AAA ATC TTA AAT ATG TCA ACT GTA         582
Arg Leu Ser Lys Glu Gln Ala Ile Lys Ile Leu Asn Met Ser Thr Val
         85                  90                  95

GCA TTG AGT AAA GAA CCC AAT CTA CTA AAA CTC AAA GCG CCA ATT ACT         630
Ala Leu Ser Lys Glu Pro Asn Leu Leu Lys Leu Lys Ala Pro Ile Thr
100                 105                 110                 115

ATA TGT GGT GAT ATT CAC GGG CAG TAT TAT GAT TTA TTG AAA CTG TTT         678
Ile Cys Gly Asp Ile His Gly Gln Tyr Tyr Asp Leu Leu Lys Leu Phe
                120                 125                 130

GAA GTT GGC GGT GAC CCC GCC GAA ATC GAC TAT TTA TTC TTG GGG GAT         726
Glu Val Gly Gly Asp Pro Ala Glu Ile Asp Tyr Leu Phe Leu Gly Asp
            135                 140                 145

TAT GTT GAT AGA GGT GCA TTC TCT TTT GAG TGT CTG ATT TAT TTG TAC         774
Tyr Val Asp Arg Gly Ala Phe Ser Phe Glu Cys Leu Ile Tyr Leu Tyr
        150                 155                 160

TCC TTG AAG TTG AAT AAT TTA GGG AGA TTT TGG ATG CTA AGA GGT AAC         822
Ser Leu Lys Leu Asn Asn Leu Gly Arg Phe Trp Met Leu Arg Gly Asn
165                 170                 175

CAT GAG TGT AAG CAC TTG ACC TCT TAT TTT ACT TTT AAG AAT GAG ATG         870
His Glu Cys Lys His Leu Thr Ser Tyr Phe Thr Phe Lys Asn Glu Met
180                 185                 190                 195

TTG CAC AAA TAC GAT ATG GAA GTT TAC GAT GCT TGC TGC AGA TCA TTC         918
Leu His Lys Tyr Asp Met Glu Val Tyr Asp Ala Cys Cys Arg Ser Phe
                200                 205                 210

AAT GTC TTA CCA TTA GCA GCT TTA ATG AAC GGA CAA TAT TTT TGT GTG         966
Asn Val Leu Pro Leu Ala Ala Leu Met Asn Gly Gln Tyr Phe Cys Val
            215                 220                 225

CAT GGT GGT ATC TCT CCA GAG TTA AAA TCA GTA GAG GAT GTT AAT AAA        1014
His Gly Gly Ile Ser Pro Glu Leu Lys Ser Val Glu Asp Val Asn Lys
        230                 235                 240

ATT AAT AGA TTT CGA GAA ATC CCA TCT CGT GGT CTC ATG TGT GAC CTA        1062
Ile Asn Arg Phe Arg Glu Ile Pro Ser Arg Gly Leu Met Cys Asp Leu
```

|     |     |     |     |     |     |     |     |     |     |     |     |     |     |     |     |
| --- | --- | --- | --- | --- | --- | --- | --- | --- | --- | --- | --- | --- | --- | --- | --- |
| 245 | | | | | 250 | | | | | 255 | | | | | |
| CTA | TGG | GCC | GAT | CCT | GTC | GAA | AAT | TAT | GAT | GAT | GCA | AGA | GAT | GGT | AGC | 1110 |
| Leu | Trp | Ala | Asp | Pro | Val | Glu | Asn | Tyr | Asp | Asp | Ala | Arg | Asp | Gly | Ser |
| 260 | | | | | 265 | | | | | 270 | | | | | 275 |
| GAA | TTT | GAT | CAG | AGC | GAG | GAT | GAA | TTC | GTA | CCT | AAC | AGT | TTG | AGG | GGT | 1158 |
| Glu | Phe | Asp | Gln | Ser | Glu | Asp | Glu | Phe | Val | Pro | Asn | Ser | Leu | Arg | Gly |
| | | | | 280 | | | | | 285 | | | | | 290 | |
| TGC | TCT | TTC | GCC | TTC | ACT | TTT | AAA | GCA | TCA | TGC | AAG | TTT | TTG | AAG | GCA | 1206 |
| Cys | Ser | Phe | Ala | Phe | Thr | Phe | Lys | Ala | Ser | Cys | Lys | Phe | Leu | Lys | Ala |
| | | | 295 | | | | | 300 | | | | | 305 | | |
| AAT | GGT | TTG | TTA | TCT | ATT | ATT | AGA | GCA | CAC | GAA | GCA | CAG | GAT | GCT | GGG | 1254 |
| Asn | Gly | Leu | Leu | Ser | Ile | Ile | Arg | Ala | His | Glu | Ala | Gln | Asp | Ala | Gly |
| | | 310 | | | | | 315 | | | | | 320 | | | |
| TAC | AGA | ATG | TAT | AAA | AAC | AAT | AAA | GTA | ACA | GGC | TTC | CCG | AGC | TTA | ATA | 1302 |
| Tyr | Arg | Met | Tyr | Lys | Asn | Asn | Lys | Val | Thr | Gly | Phe | Pro | Ser | Leu | Ile |
| | 325 | | | | | 330 | | | | | 335 | | | | |
| ACC | ATG | TTC | AGT | GCG | CCA | AAC | TAC | CTG | GAC | ACA | TAT | CAT | AAT | AAA | GCT | 1350 |
| Thr | Met | Phe | Ser | Ala | Pro | Asn | Tyr | Leu | Asp | Thr | Tyr | His | Asn | Lys | Ala |
| 340 | | | | | 345 | | | | | 350 | | | | | 355 |
| GCT | GTG | TTA | AAA | TAT | GAA | GAA | AAC | GTC | ATG | AAC | ATC | AGG | CAG | TTT | CAC | 1398 |
| Ala | Val | Leu | Lys | Tyr | Glu | Glu | Asn | Val | Met | Asn | Ile | Arg | Gln | Phe | His |
| | | | | 360 | | | | | 365 | | | | | 370 | |
| ATG | TCT | CCG | CAC | CCT | TAC | TGG | TTG | CCT | GAT | TTT | ATG | GAT | GTT | TTC | ACC | 1446 |
| Met | Ser | Pro | His | Pro | Tyr | Trp | Leu | Pro | Asp | Phe | Met | Asp | Val | Phe | Thr |
| | | | 375 | | | | | 380 | | | | | 385 | | |
| TGG | TCA | CTA | CCT | TTT | GTT | GGC | GAA | AAA | GTT | ACT | AGC | ATG | TTA | GTG | TCT | 1494 |
| Trp | Ser | Leu | Pro | Phe | Val | Gly | Glu | Lys | Val | Thr | Ser | Met | Leu | Val | Ser |
| | | 390 | | | | | 395 | | | | | 400 | | | |
| ATA | TTA | AAC | ATA | TGT | AGT | GAG | CAG | GAA | CTT | GAC | CCA | GAA | TCG | GAA | CCC | 1542 |
| Ile | Leu | Asn | Ile | Cys | Ser | Glu | Gln | Glu | Leu | Asp | Pro | Glu | Ser | Glu | Pro |
| | 405 | | | | | 410 | | | | | 415 | | | | |
| AAA | GCT | GCG | GAG | GAG | ACT | GTA | AAG | GCA | AGA | GCA | AAC | GCA | ACT | AAG | GAG | 1590 |
| Lys | Ala | Ala | Glu | Glu | Thr | Val | Lys | Ala | Arg | Ala | Asn | Ala | Thr | Lys | Glu |
| 420 | | | | | 425 | | | | | 430 | | | | | 435 |
| ACC | GGC | ACC | CCA | TCT | GAT | GAA | AAG | GCG | TCA | TCA | GCG | ATA | TTA | GAA | GAT | 1638 |
| Thr | Gly | Thr | Pro | Ser | Asp | Glu | Lys | Ala | Ser | Ser | Ala | Ile | Leu | Glu | Asp |
| | | | | 440 | | | | | 445 | | | | | 450 | |
| GAA | ACC | CGA | AGA | AAG | GCT | TTG | AGA | AAT | AAG | ATA | TTA | GCT | ATT | GCT | AAA | 1686 |
| Glu | Thr | Arg | Arg | Lys | Ala | Leu | Arg | Asn | Lys | Ile | Leu | Ala | Ile | Ala | Lys |
| | | 455 | | | | | 460 | | | | | 465 | | | |
| GTT | TCA | AGA | ATG | TTT | TCG | GTG | CTA | AGA | GAA | GAG | AGC | GAA | AAA | GTG | GAA | 1734 |
| Val | Ser | Arg | Met | Phe | Ser | Val | Leu | Arg | Glu | Glu | Ser | Glu | Lys | Val | Glu |
| | | 470 | | | | | 475 | | | | | 480 | | | |
| TAT | TTG | AAA | ACT | ATG | AAT | GCC | GGT | GTC | TTA | CCT | CGT | GGT | GCT | CTA | GCT | 1782 |
| Tyr | Leu | Lys | Thr | Met | Asn | Ala | Gly | Val | Leu | Pro | Arg | Gly | Ala | Leu | Ala |
| | 485 | | | | | 490 | | | | | 495 | | | | |
| CGT | GGG | ACT | GAA | GGT | TTG | AAT | GAA | ACG | CTA | | | | | | | 1812 |
| Arg | Gly | Thr | Glu | Gly | Leu | Asn | Glu | Thr | Leu |
| 500 | | | | | 505 | | | | | |

( 2 ) INFORMATION FOR SEQ ID NO:19:

( i ) SEQUENCE CHARACTERISTICS:
        ( A ) LENGTH: 509 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

| Met | Ser | Lys | Asp | Leu | Asn | Ser | Ser | Arg | Ile | Lys | Ile | Ile | Lys | Pro | Asn |
| --- | --- | --- | --- | --- | --- | --- | --- | --- | --- | --- | --- | --- | --- | --- | --- |
| 1 | | | | 5 | | | | | 10 | | | | | 15 | |

-continued

| | | | | | | | | | | | | | |
|---|---|---|---|---|---|---|---|---|---|---|---|---|---|
|Asp|Ser|Tyr|Ile 20|Lys|Val|Asp|Arg 25|Lys|Asp|Leu|Thr|Lys 30|Tyr|Glu|
|Leu|Glu|Asn 35|Gly|Lys|Val|Ile|Ser 40|Thr|Lys|Asp|Arg|Ser 45|Tyr|Ala|Ser|
|Val|Pro 50|Ala|Ile|Thr|Gly|Lys 55|Ile|Pro|Ser|Asp|Glu 60|Val|Phe|Asp|
|Ser 65|Lys|Thr|Gly|Leu|Pro 70|Asn|His|Ser|Phe|Leu 75|Arg|Glu|His|Phe 80|
|His|Glu|Gly|Arg|Leu 85|Ser|Lys|Glu|Gln|Ala 90|Ile|Lys|Ile|Leu|Asn|Met 95|
|Ser|Thr|Val|Ala 100|Leu|Ser|Lys|Glu|Pro 105|Asn|Leu|Leu|Lys|Leu 110|Lys|Ala|
|Pro|Ile|Thr 115|Ile|Cys|Gly|Asp|Ile 120|His|Gly|Gln|Tyr|Tyr 125|Asp|Leu|Leu|
|Lys|Leu 130|Phe|Glu|Val|Gly|Gly 135|Asp|Pro|Ala|Glu|Ile 140|Asp|Tyr|Leu|Phe|
|Leu 145|Gly|Asp|Tyr|Val|Asp 150|Arg|Gly|Ala|Phe|Ser 155|Phe|Glu|Cys|Leu|Ile 160|
|Tyr|Leu|Tyr|Ser|Leu 165|Lys|Leu|Asn|Asn|Leu 170|Gly|Arg|Phe|Trp|Met 175|Leu|
|Arg|Gly|Asn|His 180|Glu|Cys|Lys|His|Leu 185|Thr|Ser|Tyr|Phe|Thr 190|Phe|Lys|
|Asn|Glu|Met 195|Leu|His|Lys|Tyr|Asp 200|Met|Glu|Val|Tyr|Asp 205|Ala|Cys|Cys|
|Arg|Ser 210|Phe|Asn|Val|Leu|Pro 215|Leu|Ala|Ala|Leu|Met 220|Asn|Gly|Gln|Tyr|
|Phe 225|Cys|Val|His|Gly|Gly 230|Ile|Ser|Pro|Glu|Leu 235|Lys|Ser|Val|Glu|Asp 240|
|Val|Asn|Lys|Ile|Asn 245|Arg|Phe|Arg|Glu|Ile 250|Pro|Ser|Arg|Gly|Leu 255|Met|
|Cys|Asp|Leu|Leu 260|Trp|Ala|Asp|Pro|Val 265|Glu|Asn|Tyr|Asp|Asp 270|Ala|Arg|
|Asp|Gly|Ser 275|Glu|Phe|Asp|Gln|Ser 280|Glu|Asp|Glu|Phe|Val 285|Pro|Asn|Ser|
|Leu|Arg 290|Gly|Cys|Ser|Phe|Ala 295|Phe|Thr|Phe|Lys|Ala 300|Ser|Cys|Lys|Phe|
|Leu 305|Lys|Ala|Asn|Gly|Leu 310|Leu|Ser|Ile|Ile|Arg 315|Ala|His|Glu|Ala|Gln 320|
|Asp|Ala|Gly|Tyr|Arg 325|Met|Tyr|Lys|Asn|Asn 330|Lys|Val|Thr|Gly|Phe 335|Pro|
|Ser|Leu|Ile|Thr 340|Met|Phe|Ser|Ala|Pro 345|Asn|Tyr|Leu|Asp|Thr 350|Tyr|His|
|Asn|Lys|Ala 355|Ala|Val|Leu|Lys|Tyr 360|Glu|Glu|Asn|Val|Met 365|Asn|Ile|Arg|
|Gln|Phe 370|His|Met|Ser|Pro|His 375|Pro|Tyr|Trp|Leu|Pro 380|Asp|Phe|Met|Asp|
|Val 385|Phe|Thr|Trp|Ser|Leu 390|Pro|Phe|Val|Gly|Glu 395|Lys|Val|Thr|Ser|Met 400|
|Leu|Val|Ser|Ile|Leu 405|Asn|Ile|Cys|Ser|Glu 410|Gln|Glu|Leu|Asp|Pro 415|Glu|
|Ser|Glu|Pro|Lys 420|Ala|Ala|Glu|Glu|Thr 425|Val|Lys|Ala|Arg|Ala 430|Asn|Ala|
|Thr|Lys|Glu|Thr|Gly|Thr|Pro|Ser|Asp|Glu|Lys|Ala|Ser|Ser|Ala|Ile|

```
                            435                          440                         445
Leu  Glu  Asp  Glu  Thr  Arg  Arg  Lys  Ala  Leu  Arg  Asn  Lys  Ile  Leu  Ala
               450                        455                      460

Ile  Ala  Lys  Val  Ser  Arg  Met  Phe  Ser  Val  Leu  Arg  Glu  Glu  Ser  Glu
465                        470                      475                         480

Lys  Val  Glu  Tyr  Leu  Lys  Thr  Met  Asn  Ala  Gly  Val  Leu  Pro  Arg  Gly
                    485                        490                      495

Ala  Leu  Ala  Arg  Gly  Thr  Glu  Gly  Leu  Asn  Glu  Thr  Leu
               500                        505
```

( 2 ) INFORMATION FOR SEQ ID NO:20:

( i ) SEQUENCE CHARACTERISTICS:
        ( A ) LENGTH: 1767 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: DNA fragment containing
        CNA2deltaC coding sequence ( i x ) FEATURE:
        ( A ) NAME/KEY: CDS
        ( B ) LOCATION: 262..1767

( x i ) SEQUENCE DESCRIPTION: SEQ ID NO:20:

```
ATAGTCTATA  ATACGTTTGA  TACAGCTAGA  TATCGCTAGC  GCCAACATTG  TCCCCCTCTC      60

TTGATCAATG  CTTTTTTTCG  GCCCGAGACA  AATGAGAAAA  TGTCCTAAAA  ATACCTTTCA     120

TCAAGACTCC  TATTTTTCCT  TAGAAAAAAC  ATATATCCAA  CTGGAACAGT  ATTAAGCCAA     180

TTGCTACGAT  ACAAACAAAA  GGAGATATTC  CTTCCCTCCC  ATAGAGTCAC  ACAGGAGCCA     240

GTACTTCTTC  TTGAACCCGC  A  ATG  TCT  TCA  GAC  GCT  ATA  AGA  AAT  ACT  GAG     291
              Met  Ser  Ser  Asp  Ala  Ile  Arg  Asn  Thr  Glu
               1                    5                         10

CAG  ATA  AAC  GCC  GCT  ATT  AAA  ATT  ATA  GAA  AAC  AAA  ACA  GAG  CGT  CCG    339
Gln  Ile  Asn  Ala  Ala  Ile  Lys  Ile  Ile  Glu  Asn  Lys  Thr  Glu  Arg  Pro
               15                         20                        25

CAA  TCG  TCC  ACA  ACC  CCT  ATA  GAT  TCG  AAG  GCT  AGT  ACA  GTT  GCT  GCT    387
Gln  Ser  Ser  Thr  Thr  Pro  Ile  Asp  Ser  Lys  Ala  Ser  Thr  Val  Ala  Ala
               30                         35                        40

GCT  AAT  TCC  ACG  GCC  ACA  GAA  ACT  TCC  AGA  GAC  CTT  ACA  CAA  TAT  ACC    435
Ala  Asn  Ser  Thr  Ala  Thr  Glu  Thr  Ser  Arg  Asp  Leu  Thr  Gln  Tyr  Thr
               45                         50                        55

CTA  GAT  GAC  GGA  AGA  GTC  GTA  TCG  ACA  AAC  CGC  AGA  ATA  ATG  AAT  AAA    483
Leu  Asp  Asp  Gly  Arg  Val  Val  Ser  Thr  Asn  Arg  Arg  Ile  Met  Asn  Lys
     60                         65                        70

GTG  CCC  GCC  ATC  ACG  TCA  CAT  GTT  CCT  ACA  GAT  GAA  GAG  CTG  TTC  CAG    531
Val  Pro  Ala  Ile  Thr  Ser  His  Val  Pro  Thr  Asp  Glu  Glu  Leu  Phe  Gln
75                         80                        85                        90

CCC  AAT  GGG  ATA  CCT  CGT  CAC  GAA  TTC  CTA  AGA  GAT  CAT  TTC  AAG  CGC    579
Pro  Asn  Gly  Ile  Pro  Arg  His  Glu  Phe  Leu  Arg  Asp  His  Phe  Lys  Arg
                    95                        100                      105

GAG  GGC  AAA  TTG  TCG  GCT  GCG  CAG  GCG  GCC  AGG  ATC  GTT  ACA  CTT  GCA    627
Glu  Gly  Lys  Leu  Ser  Ala  Ala  Gln  Ala  Ala  Arg  Ile  Val  Thr  Leu  Ala
               110                       115                      120

ACG  GAA  CTC  TTC  AGC  AAA  GAA  CCC  AAC  CTT  ATA  TCT  GTT  CCC  GCC  CCA    675
```

```
                Thr Glu Leu Phe Ser Lys Glu Pro Asn Leu Ile Ser Val Pro Ala Pro
                    125                 130                 135

ATC ACA GTT TGC GGT GAT ATC CAT GGC CAG TAC TTT GAC CTT TTG AAG              723
Ile Thr Val Cys Gly Asp Ile His Gly Gln Tyr Phe Asp Leu Leu Lys
    140                 145                 150

CTA TTC GAA GTT GGC GGA GAT CCG GCC ACT ACA TCG TAT TTG TTC TTG              771
Leu Phe Glu Val Gly Gly Asp Pro Ala Thr Thr Ser Tyr Leu Phe Leu
155                 160                 165                 170

GGA GAC TAT GTC GAC AGA GGG TCC TTT TCG TTT GAG TGT CTT ATT TAT              819
Gly Asp Tyr Val Asp Arg Gly Ser Phe Ser Phe Glu Cys Leu Ile Tyr
                175                 180                 185

TTA TAT TCT TTG AAG CTG AAT TTT AAC GAC CAT TTC TGG CTA CTG AGG              867
Leu Tyr Ser Leu Lys Leu Asn Phe Asn Asp His Phe Trp Leu Leu Arg
            190                 195                 200

GGT AAC CAC GAA TGT AAG CAT CTA ACG TCA TAT TTC ACT TTC AAA AAT              915
Gly Asn His Glu Cys Lys His Leu Thr Ser Tyr Phe Thr Phe Lys Asn
        205                 210                 215

GAA ATG CTG CAC AAG TAC AAT CTA GAT ATT TAC GAG AAA TGC TGC GAA              963
Glu Met Leu His Lys Tyr Asn Leu Asp Ile Tyr Glu Lys Cys Cys Glu
    220                 225                 230

TCG TTT AAC AAC TTG CCC CTG GCT GCG TTA ATG AAC GGA CAG TAT CTT             1011
Ser Phe Asn Asn Leu Pro Leu Ala Ala Leu Met Asn Gly Gln Tyr Leu
235                 240                 245                 250

TGT GTT CAT GGT GGT ATA TCT CCC GAG TTA AAC TCT TTA CAG GAC ATT             1059
Cys Val His Gly Gly Ile Ser Pro Glu Leu Asn Ser Leu Gln Asp Ile
                255                 260                 265

AAC AAC CTA AAT AGA TTC AGG GAG ATT CCC TCT CAT GGC CTG ATG TGT             1107
Asn Asn Leu Asn Arg Phe Arg Glu Ile Pro Ser His Gly Leu Met Cys
            270                 275                 280

GAT CTG TTG TGG GCT GAC CCG ATT GAA GAG TAC GAC GAA GTC TTG GAT             1155
Asp Leu Leu Trp Ala Asp Pro Ile Glu Glu Tyr Asp Glu Val Leu Asp
        285                 290                 295

AAA GAC TTG ACT GAG GAA GAC ATA GTG AAC TCC AAA ACC ATG GTT CCT             1203
Lys Asp Leu Thr Glu Glu Asp Ile Val Asn Ser Lys Thr Met Val Pro
    300                 305                 310

CAT CAT GGC AAG ATG GCA CCT TCA AGG GAT ATG TTT GTC CCA AAC TCA             1251
His His Gly Lys Met Ala Pro Ser Arg Asp Met Phe Val Pro Asn Ser
315                 320                 325                 330

GTA AGG GGC TGT TCA TAT GCC TTC ACG TAT CGT GCT GCG TGC CAT TTT             1299
Val Arg Gly Cys Ser Tyr Ala Phe Thr Tyr Arg Ala Ala Cys His Phe
                335                 340                 345

CTG CAA GAG ACT GGC CTG TTG TCC ATC ATC AGG GCA CAC GAG GCT CAA             1347
Leu Gln Glu Thr Gly Leu Leu Ser Ile Ile Arg Ala His Glu Ala Gln
            350                 355                 360

GAC GCT GGT TAT AGA ATG TAC AAA AAT ACC AAG ACT TTG GGC TTT CCC             1395
Asp Ala Gly Tyr Arg Met Tyr Lys Asn Thr Lys Thr Leu Gly Phe Pro
        365                 370                 375

TCT CTT TTG ACC CTT TTC AGT GCG CCT AAC TAC TTG GAC ACC TAC AAT             1443
Ser Leu Leu Thr Leu Phe Ser Ala Pro Asn Tyr Leu Asp Thr Tyr Asn
    380                 385                 390

AAT AAG GCT GCC ATA TTG AAA TAC GAA AAT AAT GTT ATG AAT ATC AGA             1491
Asn Lys Ala Ala Ile Leu Lys Tyr Glu Asn Asn Val Met Asn Ile Arg
395                 400                 405                 410

CAA TTC AAC ATG ACT CCA CAC CCC TAT TGG TTA CCA GAT TTC ATG GAC             1539
Gln Phe Asn Met Thr Pro His Pro Tyr Trp Leu Pro Asp Phe Met Asp
                415                 420                 425

GTT TTC ACG TGG TCC TTG CCA TTT GTT GGT GAA AAA GTT ACA GAG ATG             1587
Val Phe Thr Trp Ser Leu Pro Phe Val Gly Glu Lys Val Thr Glu Met
            430                 435                 440

CTT GTC GCA ATT CTA AAC ATC TGT ACT GAA GAT GAG CTG AAA AAC GAC             1635
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Leu | Val | Ala | Ile | Leu | Asn | Ile | Cys | Thr | Glu | Asp | Glu | Leu | Glu | Asn | Asp |      |
|     |     | 445 |     |     |     | 450 |     |     |     |     | 455 |     |     |     |     |      |
| ACC | CCC | GTC | ATT | GAA | GAA | TTA | GTT | GGT | ACC | GAT | AAA | AAA | TTG | CCA | CAA | 1683 |
| Thr | Pro | Val | Ile | Glu | Glu | Leu | Val | Gly | Thr | Asp | Lys | Lys | Leu | Pro | Gln |      |
|     | 460 |     |     |     |     | 465 |     |     |     |     | 470 |     |     |     |     |      |
| GCT | GGT | AAG | TCG | GAA | GCA | ACT | CCA | CAA | CCA | GCC | ACT | TCG | GCG | TCG | CCT | 1731 |
| Ala | Gly | Lys | Ser | Glu | Ala | Thr | Pro | Gln | Pro | Ala | Thr | Ser | Ala | Ser | Pro |      |
| 475 |     |     |     |     | 480 |     |     |     |     | 485 |     |     |     |     | 490 |      |
| AAA | CAT | GCT | TCC | ATT | TTA | GAT | GAC | GAA | CAT | CGA | AGG |     |     |     |     | 1767 |
| Lys | His | Ala | Ser | Ile | Leu | Asp | Asp | Glu | His | Arg | Arg |     |     |     |     |      |
|     |     |     |     | 495 |     |     |     |     | 500 |     |     |     |     |     |     |      |

( 2 ) INFORMATION FOR SEQ ID NO:21:

( i ) SEQUENCE CHARACTERISTICS:
        ( A ) LENGTH: 502 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Ser | Ser | Asp | Ala | Ile | Arg | Asn | Thr | Glu | Gln | Ile | Asn | Ala | Ala | Ile |
| 1   |     |     |     | 5   |     |     |     |     | 10  |     |     |     |     | 15  |     |
| Lys | Ile | Ile | Glu | Asn | Lys | Thr | Glu | Arg | Pro | Gln | Ser | Ser | Thr | Thr | Pro |
|     |     |     | 20  |     |     |     |     | 25  |     |     |     |     | 30  |     |     |
| Ile | Asp | Ser | Lys | Ala | Ser | Thr | Val | Ala | Ala | Ala | Asn | Ser | Thr | Ala | Thr |
|     |     | 35  |     |     |     |     | 40  |     |     |     |     | 45  |     |     |     |
| Glu | Thr | Ser | Arg | Asp | Leu | Thr | Gln | Tyr | Thr | Leu | Asp | Asp | Gly | Arg | Val |
|     | 50  |     |     |     |     | 55  |     |     |     |     | 60  |     |     |     |     |
| Val | Ser | Thr | Asn | Arg | Arg | Ile | Met | Asn | Lys | Val | Pro | Ala | Ile | Thr | Ser |
| 65  |     |     |     |     | 70  |     |     |     |     | 75  |     |     |     |     | 80  |
| His | Val | Pro | Thr | Asp | Glu | Glu | Leu | Phe | Gln | Pro | Asn | Gly | Ile | Pro | Arg |
|     |     |     |     | 85  |     |     |     |     | 90  |     |     |     |     | 95  |     |
| His | Glu | Phe | Leu | Arg | Asp | His | Phe | Lys | Arg | Glu | Gly | Lys | Leu | Ser | Ala |
|     |     |     | 100 |     |     |     |     | 105 |     |     |     |     | 110 |     |     |
| Ala | Gln | Ala | Ala | Arg | Ile | Val | Thr | Leu | Ala | Thr | Glu | Leu | Phe | Ser | Lys |
|     |     |     | 115 |     |     |     |     | 120 |     |     |     |     | 125 |     |     |
| Glu | Pro | Asn | Leu | Ile | Ser | Val | Pro | Ala | Pro | Ile | Thr | Val | Cys | Gly | Asp |
|     | 130 |     |     |     |     | 135 |     |     |     |     | 140 |     |     |     |     |
| Ile | His | Gly | Gln | Tyr | Phe | Asp | Leu | Leu | Lys | Leu | Phe | Glu | Val | Gly | Gly |
| 145 |     |     |     |     | 150 |     |     |     |     | 155 |     |     |     |     | 160 |
| Asp | Pro | Ala | Thr | Thr | Ser | Tyr | Leu | Phe | Leu | Gly | Asp | Tyr | Val | Asp | Arg |
|     |     |     |     | 165 |     |     |     |     | 170 |     |     |     |     | 175 |     |
| Gly | Ser | Phe | Ser | Phe | Glu | Cys | Leu | Ile | Tyr | Leu | Tyr | Ser | Leu | Lys | Leu |
|     |     |     | 180 |     |     |     |     | 185 |     |     |     |     | 190 |     |     |
| Asn | Phe | Asn | Asp | His | Phe | Trp | Leu | Leu | Arg | Gly | Asn | His | Glu | Cys | Lys |
|     |     | 195 |     |     |     |     | 200 |     |     |     |     | 205 |     |     |     |
| His | Leu | Thr | Ser | Tyr | Phe | Thr | Phe | Lys | Asn | Glu | Met | Leu | His | Lys | Tyr |
|     | 210 |     |     |     |     | 215 |     |     |     |     | 220 |     |     |     |     |
| Asn | Leu | Asp | Ile | Tyr | Glu | Lys | Cys | Cys | Glu | Ser | Phe | Asn | Asn | Leu | Pro |
| 225 |     |     |     |     | 230 |     |     |     |     | 235 |     |     |     |     | 240 |
| Leu | Ala | Ala | Leu | Met | Asn | Gly | Gln | Tyr | Leu | Cys | Val | His | Gly | Gly | Ile |
|     |     |     |     | 245 |     |     |     |     | 250 |     |     |     |     | 255 |     |
| Ser | Pro | Glu | Leu | Asn | Ser | Leu | Gln | Asp | Ile | Asn | Asn | Leu | Asn | Arg | Phe |
|     |     |     | 260 |     |     |     |     | 265 |     |     |     |     | 270 |     |     |
| Arg | Glu | Ile | Pro | Ser | His | Gly | Leu | Met | Cys | Asp | Leu | Leu | Trp | Ala | Asp |
|     |     | 275 |     |     |     |     | 280 |     |     |     |     | 285 |     |     |     |

| Pro | Ile | Glu | Glu | Tyr | Asp | Glu | Val | Leu | Asp | Lys | Asp | Leu | Thr | Glu | Glu |
|---|---|---|---|---|---|---|---|---|---|---|---|---|---|---|---|
| | 290 | | | | 295 | | | | | 300 | | | | | |
| Asp | Ile | Val | Asn | Ser | Lys | Thr | Met | Val | Pro | His | His | Gly | Lys | Met | Ala |
| 305 | | | | | 310 | | | | | 315 | | | | | 320 |
| Pro | Ser | Arg | Asp | Met | Phe | Val | Pro | Asn | Ser | Val | Arg | Gly | Cys | Ser | Tyr |
| | | | | 325 | | | | | 330 | | | | | 335 | |
| Ala | Phe | Thr | Tyr | Arg | Ala | Ala | Cys | His | Phe | Leu | Gln | Glu | Thr | Gly | Leu |
| | | | 340 | | | | | 345 | | | | | 350 | | |
| Leu | Ser | Ile | Ile | Arg | Ala | His | Glu | Ala | Gln | Asp | Ala | Gly | Tyr | Arg | Met |
| | | 355 | | | | | 360 | | | | | 365 | | | |
| Tyr | Lys | Asn | Thr | Lys | Thr | Leu | Gly | Phe | Pro | Ser | Leu | Leu | Thr | Leu | Phe |
| | 370 | | | | | 375 | | | | | 380 | | | | |
| Ser | Ala | Pro | Asn | Tyr | Leu | Asp | Thr | Tyr | Asn | Asn | Lys | Ala | Ala | Ile | Leu |
| 385 | | | | | 390 | | | | | 395 | | | | | 400 |
| Lys | Tyr | Glu | Asn | Asn | Val | Met | Asn | Ile | Arg | Gln | Phe | Asn | Met | Thr | Pro |
| | | | | 405 | | | | | 410 | | | | | 415 | |
| His | Pro | Tyr | Trp | Leu | Pro | Asp | Phe | Met | Asp | Val | Phe | Thr | Trp | Ser | Leu |
| | | | 420 | | | | | 425 | | | | | 430 | | |
| Pro | Phe | Val | Gly | Glu | Lys | Val | Thr | Glu | Met | Leu | Val | Ala | Ile | Leu | Asn |
| | | 435 | | | | | 440 | | | | | 445 | | | |
| Ile | Cys | Thr | Glu | Asp | Glu | Leu | Glu | Asn | Asp | Thr | Pro | Val | Ile | Glu | Glu |
| | 450 | | | | | 455 | | | | | 460 | | | | |
| Leu | Val | Gly | Thr | Asp | Lys | Lys | Leu | Pro | Gln | Ala | Gly | Lys | Ser | Glu | Ala |
| 465 | | | | | 470 | | | | | 475 | | | | | 480 |
| Thr | Pro | Gln | Pro | Ala | Thr | Ser | Ala | Ser | Pro | Lys | His | Ala | Ser | Ile | Leu |
| | | | | 485 | | | | | 490 | | | | | 495 | |
| Asp | Asp | Glu | His | Arg | Arg | | | | | | | | | | |
| | | | | 500 | | | | | | | | | | | |

( 2 ) INFORMATION FOR SEQ ID NO:22:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: G4-PCR- A ( x i ) SEQUENCE DESCRIPTION: SEQ ID NO:22:

```
GCCCTATCGT GCACTCACCG ACGC                                          24
```

( 2 ) INFORMATION FOR SEQ ID NO:23:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO (  v i  ) ORIGINAL SOURCE:
    ( C ) INDIVIDUAL ISOLATE: G4-PCR- B ( x i ) SEQUENCE DESCRIPTION: SEQ ID NO:23:

GTGAAGGCCC TACTGAGCCA GGAG                                                                          24